(12) United States Patent
Beutel et al.

(10) Patent No.: US 11,493,519 B2
(45) Date of Patent: Nov. 8, 2022

(54) METHODS OF CHARACTERIZING CONDENSATE-ASSOCIATED CHARACTERISTICS OF COMPOUNDS AND USES THEREOF

(71) Applicant: Dewpoint Therapeutics, Inc., Boston, MA (US)

(72) Inventors: Bruce Aaron Beutel, Needham, MA (US); Peter Jeffrey Dandliker, Newton, MA (US); Stephen Paul Hale, Belmont, MA (US); Mark Andrew Murcko, Holliston, MA (US); Edgar Erik Boczek, Dresden (DE); Matthäus Mittasch, Dresden (DE); Diana Maria Mitrea, Canton, MA (US)

(73) Assignee: DEWPOINT THERAPEUTICS, INC., Boston, MA (US)

( * ) Notice: Subject to any disclaimer, the term of this patent is extended or adjusted under 35 U.S.C. 154(b) by 433 days.

(21) Appl. No.: 16/785,448

(22) Filed: Feb. 7, 2020

(65) Prior Publication Data
US 2020/0284801 A1    Sep. 10, 2020

Related U.S. Application Data

(60) Provisional application No. 62/803,365, filed on Feb. 8, 2019, provisional application No. 62/866,526, filed on Jun. 25, 2019.

(51) Int. Cl.
*G01N 33/68* (2006.01)
*C09K 11/06* (2006.01)
(Continued)

(52) U.S. Cl.
CPC .......... *G01N 33/6848* (2013.01); *C09K 11/06* (2013.01); *G01N 21/6428* (2013.01);
(Continued)

(58) Field of Classification Search
None
See application file for complete search history.

(56) References Cited

U.S. PATENT DOCUMENTS 10,303,979 B2    5/2019   Kraus et al.
11,340,231 B2    5/2022   Szewczak et al.
(Continued)

FOREIGN PATENT DOCUMENTS

ES    2338392 A1      5/2010
KR    20150112415 A   10/2015
(Continued)

OTHER PUBLICATIONS

Cheng, X. et al. Direct measurement of oligonucleotide binding stoichiometry of gene V protein by mass spectrometry, Proc. Natl. Acad. Sci. USA, vol. 93, pp. 7022-7027 (Year: 1996).*
(Continued)

*Primary Examiner* — Xiaoyun R Xu
(74) *Attorney, Agent, or Firm* — Morrison & Foerster LLP

(57) ABSTRACT

Methods of assessing, such as characterizing or determining, condensate-associated characteristics of a compound, such as a test compound, and applications thereof are provided. For example, methods of determining a partition characteristic of a test compound in a target condensate, methods of determining a relative partition characteristic of a test compound in a target condensate, and methods of determining a condensate preference profile of a test compound are provided. Additionally, methods of designing and/or identifying and/or making a compound, or portion thereof, with a desired relative condensate partition characteristic are provided.

36 Claims, 10 Drawing Sheets

(51) Int. Cl.
*G01N 21/64* (2006.01)
*G01N 33/58* (2006.01)
*G01N 21/33* (2006.01)
*G01N 30/02* (2006.01)
*H01J 49/26* (2006.01)

(52) U.S. Cl.
CPC ........... *G01N 33/582* (2013.01); *G01N 21/33* (2013.01); *G01N 30/02* (2013.01); *G01N 2021/6439* (2013.01); *G01N 2030/027* (2013.01); *G01N 2333/916* (2013.01); *H01J 49/26* (2013.01)

(56) References Cited

U.S. PATENT DOCUMENTS

| | | |
|---|---|---|
| 2007/0054353 A1 | 3/2007 | White et al. |
| 2007/0178537 A1 | 8/2007 | Chiosis et al. |
| 2007/0214509 A1 | 9/2007 | Langston |
| 2009/0143433 A1 | 6/2009 | Hendrix |
| 2009/0298910 A1 | 12/2009 | Griffey |
| 2014/0121122 A1 | 5/2014 | Li |
| 2014/0242602 A1 | 8/2014 | Chiosis et al. |
| 2014/0287932 A1 | 9/2014 | Hnisz |
| 2016/0235731 A1 | 8/2016 | Bradner |
| 2016/0348180 A1 | 12/2016 | Al-murrani |
| 2017/0233762 A1 | 8/2017 | Zalatan |
| 2017/0355977 A1 | 12/2017 | Brangwynne |
| 2018/0009779 A1 | 1/2018 | Bradner |
| 2018/0133168 A1 | 5/2018 | Hong et al. |
| 2018/0251497 A1 | 9/2018 | Brangwynne |
| 2018/0313827 A1 | 11/2018 | Baldwin et al. |
| 2019/0127428 A1 | 5/2019 | Taylor |
| 2019/0352648 A1 | 11/2019 | Young |
| 2019/0382346 A1 | 12/2019 | Dalfo Capella |
| 2020/0150107 A1 | 5/2020 | Hyman et al. |
| 2021/0208153 A1 | 7/2021 | Szewczak et al. |
| 2022/0120736 A1 | 4/2022 | Young et al. |

FOREIGN PATENT DOCUMENTS

| | | | |
|---|---|---|---|
| WO | WO2002038734 A2 | 5/2002 | |
| WO | WO2002038734 A3 | 7/2002 | |
| WO | 2005099745 A2 | 10/2005 | |
| WO | 2007071060 A1 | 6/2007 | |
| WO | 2011093782 A1 | 8/2011 | |
| WO | WO2011100374 A2 | 8/2011 | |
| WO | WO2011100374 A3 | 12/2011 | |
| WO | WO2012006551 A2 | 1/2012 | |
| WO | WO2012006551 A3 | 4/2012 | |
| WO | 2012162249 A1 | 11/2012 | |
| WO | 2012167086 A2 | 12/2012 | |
| WO | WO2014062686 A1 | 4/2014 | |
| WO | WO2014066848 A1 | 5/2014 | |
| WO | 2014145975 A2 | 9/2014 | |
| WO | WO2017/068341 | * 4/2017 | ........... G01N 33/543 |
| WO | 2017207460 A1 | 12/2017 | |
| WO | WO2018006074 A2 | 1/2018 | |
| WO | WO2018006074 A3 | 2/2018 | |
| WO | WO2018129544 A1 | 7/2018 | |
| WO | 2018170794 A1 | 9/2018 | |
| WO | 2019032613 A1 | 2/2019 | |
| WO | WO2019084362 A2 | 5/2019 | |
| WO | WO2019084362 A3 | 5/2019 | |
| WO | WO2019109017 A1 | 6/2019 | |
| WO | WO2019171068 A1 | 9/2019 | |
| WO | WO2019183552 A2 | 9/2019 | |
| WO | WO2019183552 A3 | 10/2019 | |
| WO | WO2020037234 A1 | 2/2020 | |
| WO | WO2020078924 A1 | 4/2020 | |
| WO | 2020163795 A1 | 8/2020 | |
| WO | 2020232416 A1 | 11/2020 | |
| WO | 2021055642 A2 | 3/2021 | |
| WO | 2021055644 A1 | 3/2021 | |
| WO | 2022035989 A1 | 2/2022 | |
| WO | 2022187202 A1 | 9/2022 | |
| WO | 2022187225 A1 | 9/2022 | |

OTHER PUBLICATIONS

Adams, V.H. et al. (May 18, 2007). "Intrinsic Disorder And Autonomous Domain Function In The Multifunctional Nuclear Protein, MeCP2," Journal of Biological Chemistry 282(20):15057-15064.

Aguzzi, A. et al. (Jul. 2016). "Phase Separation: Linking Cellular Compartmentalization To Disease," Trends in Cell Biology 26(7):547-558.

Alberti, S. (2017). "The Wisdom Of Crowds: Regulating Cell Function Through Condensed States Of Living Matter," J. Cell Sci. 130(17):2789-2796.

Alberti, S. (Oct. 23, 2017). "Phase Separation in Biology," Curr Biol. 27(20):R1097-R1102.

Alberti, S. et al. (Nov. 2, 2018). "A User's Guide For Phase Separation Assays With Purified Proteins." Journal Of Molecular Biology 430(23):4806-4820.

Ali, M. et al. (May 22, 2018). "High-Throughput Discovery Of Functional Disordered Regions," Molecular Systems Biology 14(5):e8377, 2 pages.

Allshire, R.C. et al. (Apr. 2018, e-pub. Dec. 13, 2017). "Ten Principles Of Heterochromatin Formation And Function," Nature Reviews Molecular Cell Biology 19(4):229-244, 39 pages.

Amir, R.E. et al. (Oct. 1999). "Rett Syndrome Is Caused By Mutations In X-Linked MECP2, Encoding Methyl-CpG-Binding Protein 2," Nature Genetics, 23(2):185-188.

An, W.F. et al. (2009). "Introduction: Cell-Based Assays For High-Throughput Screening," Methods Mol Biol. 486:1-12.

Anderson, E.N. et al. (2018). "Traumatic Injury Induces Stress Granule Formation and Enhances Motor Dysfunctions in ALS/FTD Models," Hum. Mol. Genet. 27(8):1366-1381.

Ausio, J. et al. (Sep. 2014). "MeCP2: The Long Trip From A Chromatin Protein To Neurological Disorders," Trends In Molecular Medicine 20(9):487-498.

Babu, M.M. et al. (Oct. 15, 2016). "The Contribution Of Intrinsically Disordered Regions To Protein Function, Cellular Complexity, And Human Disease," Biochemical Society Transactions 44(5):1185-1200.

Bajar, B.T. et al. (Sep. 2016). "A Guide To Fluorescent Protein FRET Pairs," Sensors 16(9):1488, 24 pages.

Banani, S.F. et al. (Jul. 28, 2016, e-pub. Jun. 30, 2016). "Compositional Control of Phase-Separated Cellular Bodies," Cell 166(3):651-663.

Banani, S.F. et al. (2017, e-pub. Feb. 22, 2017). "Biomolecular Condensates: Organizers Of Cellular Biochemistry," Nat Rev Mol Cell Biol 18(5):285-298, 14 pages.

Bannister, A.J. et al. (Mar. 2001). "Selective Recognition Of Methylated Lysine 9 On Histone H3 By The HP1 Chromo Domain," Nature 410(6824):120-124.

Baron, D.M. et al. (Aug. 31, 2013). "Amyotrophic Lateral Sclerosis-Linked FUS/TLS Alters Stress Granule Assembly And Dynamics," Molecular Neurodegeneration 8(1):30, 18 pages.

Berry, J. et al. (Sep. 22, 2015, e-pub. Sep. 8, 2015). "RNA Transcription Modulates Phase Transition-Driven Nuclear Body Assembly," Proc Natl Acad Sci USA 112(38):E5237-E5245.

Best, R.B. (Feb. 2017, e-pub Mar. 1, 2017). "Computational And Theoretical Advances In Studies Of Intrinsically Disordered Proteins," Current Opinion in Structural Biology 42:147-154.

Boeynaems, S. et al. (Jun. 2018, e-pub. Mar. 27, 2018). "Protein Phase Separation: A New Phase In Cell Biology," Trends In Cell Biology 28(6):420-435, 26 pages.

Boija, A. et al. (Dec. 13, 2018, e-pub. Nov. 15, 2018). "Transcription Factors Activate Genes through the Phase-Separation Capacity of Their Activation Domains," Cell 175(7):1842-1855.

Bojcsuk, D. et al. (Apr. 20, 2017; e-pub. Dec. 19, 2016). "Inducible super-enhancers are organized based on canonical signal-specific transcription factor binding elements," Nucleic Acids Res. 45(7):3693-3706.

(56) References Cited

OTHER PUBLICATIONS

Borggrefe, T. et al. (2011, e-pub Aug. 4, 2011). "Interactions Between Subunits Of The Mediator Complex With Gene-Specific Transcription Factors," Semin. Cell Dev. Biol. 22(7):759-768.

Bouchard J.J. et al. (Oct. 4, 2018, e-pub Sep. 20, 2018). "Cancer Mutations of the Tumor Suppressor SPOP Disrupt the Formation of Active," Phase-Separated Compartments. Mol Cell 72(1):19-36, 43 pages.

Boulay, G. et al. (2017). "Cancer-Specific Retargeting of BAF Complexes by a Prion-like Domain," Cell 171(1):163-178, 38 pages.

Boyd, J.D. et al. (Jan. 2014). "A High-Content Screen Identifies Novel Compounds That Inhibit Stress-Induced TDP-43 Cellular Aggregation And Associated Cytotoxicity." J Biomol Screen 19(1):44-56, 18 pages.

Bradner, J.E. et al. (Feb. 2017). "Transcriptional Addiction in Cancer," Cell 168(4):629-643.

Brangwynne, C.P. et al. (2013). "Phase Transitions And Size Scaling Of Membrane-Less Organelles," J Cell Biol. 203(6):875-881.

Brangwynne, C.P. et al. (Jun. 26, 2009). "Germline P Granules Are Liquid Droplets That Localize By Controlled Dissolution/Condensation," Science 324:1729-1732.

Buckley, D.L. et al. (2012). "Targeting The Von Hippel-Lindau E3 Ubiquitin Ligase Using Small Molecules To Disrupt The VHL/HIF-1 A Interaction," J Am Chem Soc. 134(10):4465-4468.

Burke, K.A. et al. (Oct. 15, 2015). "Residue-by-Residue View of In Vitro FUS Granules that Bind the C-Terminal Domain of RNA Polymerase II," Molecular Cell 60(2):231-241.

Carmony, K.C. et al. (2012). Chapter 44 in "PROTAC-Induced Proteolytic Targeting," Methods Mol Biol. 832, 11 pages.

Carpenter, A.E. et al. (Oct. 31, 2006). "Cellprofiler: Image Analysis Software For Identifying And Quantifying Cell Phenotypes," Genome Biology 7(10):R100, 11 pages.

Carroll J.S. et al. (Nov. 2006). "Genome-Wide Analysis Of Estrogen Receptor Binding Sites," Nat Genet 38(11):1289-1297.

Che, D.L. et al. (Oct. 16, 2015). "The Dual Characteristics of Light-Induced Cryptochrome 2, Homo-oligomerization and Heterodimerization, for Optogenetic Manipulation in Mammalian Cells," ACS Synth Biol. 4(10):1124-1135, 26 pages.

Chen, Y. et al. (Apr. 2019, e-pub. Aug. 5, 2019). "Genome Organization Around Nuclear Speckles," Current Opinion in Genetics & Development 55:91-99.

Cheutin, T. et al. (Jan. 31, 2003). "Maintenance Of Stable Heterochromatin Domains By Dynamic HP1 Binding," Science 299(5607):721-725.

Chiolo, I. et al. (Mar. 4, 2011). "Double-Strand Breaks In Heterochromatin Move Outside Of A Dynamic HP1a Domain To Complete Recombinational Repair," Cell 144(5):732-744.

Cho, W.K. et al. (2018). "Mediator and RNA Polymerase II Clusters Associate In Transcription-Dependent Condensates," Science 361(6400):412-415, 13 pages.

Cho, W.K. et al. (May 3, 2016). "RNA Polymerase II Cluster Dynamics Predict Mrna mRNA Output In Living Cells, RNA Polymerase II Cluster Dynamics Predict Mrna Output In Living Cells." Elife 5. pii: e13617, 31 pages.

Chong, S. et al. (2018). "Imaging Dynamic And Selective Low-Complexity Domain Interactions That Control Gene Transcription," Science 361(6400):eaar2555, 25 pages.

Cisse, I.I. et al. (Aug. 9, 2013). "Real-Time Dynamics Of RNA Polymerase II Clustering In Live Human Cells," Science 341(6146):664-667.

Conway, E.L. (Jan. 1, 1998). "A Review Of The Randomized Controlled Trials Of Tacrine In The Treatment Of Alzheimer's Disease: Methodologic Considerations," Clinical Neuropharmacol 21(1):8-17.

Conway, J.W. et al. (Feb. 7, 2005, e-pub. Nov. 24, 2004). "The Mammalian Mediator Complex," FEBS Lett. 579(4):904-908.

Dolgin, E. (Mar. 15, 2018). "Cell Biology's New Phase," Nature 555(7696):300-302, posted Dec. 17, 2018 on bioRXIV,http://www.cbeslm.cpaneldev.princeton.edu/wp-content/uploads/2019/01/NaturePhase.pdf.

Duan, L. et al. (Sep. 2017). "Understanding CRY2 Interactions For Optical Control Of Intracellular Signaling," Nature Communications 8(1):1-10547, 10 pages.

Dubik, D. et al. (Dec. 15, 1987). "Stimulation Of C-Myc Oncogene Expression Associated With Estrogen-Induced Proliferation Of Human Breast Cancer Cells," Cancer Res 47(24):6517-6521.

Ebmeier, C.C. et al. (Aug. 1, 2017). "Human TFIIH Kinase CDK7 Regulates Transcription-Associated Chromatin Modifications," Cell Rep 20(5):1173-1186.

Fang, M.Y. et al. (Sep. 4, 2009). "Small-Molecule Modulation of TDP-43 Recruitment to Stress Granules Prevents Persistent TDP-43 Accumulation in ALS/FTD," Neuron 103(5):802-819.

Fanning, S.W. et al. (Feb. 2, 2016). "Estrogen Receptor Alpha Somatic Mutations Y537S And D538G Confer Breast Cancer Endocrine Resistance By Stabilizing The Activating Function-2 Binding Conformation," Elife 5:e12792, 25 pages.

Feric, M. et al. (Jun. 16, 2016). "Coexisting Liquid Phases Underlie Nucleolar Subcompartments," Cell 165(7):1686-1697.

Festenstein, R. et al. (Jan. 31, 2003). "Modulation of Heterochromatin Protein 1 Dynamics in Primary Mammalian Cells," Science 299(5607):719-721.

Fu, D. et al. (Jul. 2014). "Imaging The Intracellular Distribution Of Tyrosine Kinase Inhibitors In Living Cells With Quantitative Hyperspectral Stimulated Raman Scattering," Nature Chemistry 6(7):614-622, 18 pages.

Fukaya, T. et al. (Jul. 14, 2016). "Enhancer Control of Transcriptional Bursting," Cell 166(2):358-368.

Galdeano, C. (Aug. 28, 2014). "Structure-Guided Design And Optimization Of Small Molecules Targeting The Protein-Protein Interaction Between The Von Hippel-Lindau (VHL) E3 Ubiquitin Ligase And The Hypoxia Inducible Factor (HIF) Alpha Subunit With In Vitro Nanomolar Affinities," J. Med. Chem. 57(20):8657-8663.

Germain, P. et al. (Dec. 2006). "Overview Of Nomenclature Of Nuclear Receptors," Pharmacological Reviews 58(4):685-704.

Ghosh, R.P. et al. (May 25, 2010). "Unique Physical Properties And Interactions Of The Domains Of Methylated DNA Binding Protein 2 (MeCP2)," Biochemistry 49(20):4395-4410, 38 pages.

Gibson, B.A. et al. (Oct. 3, 2019). "Organization Of Chromatin By Intrinsic And Regulated Phase Separation," Cell 179(2):470-484.

Grewal, S.I.S. et al. (Jan. 2007). "Heterochromatin Revisited," Nature Reviews Genetics 8(1):35-46.

Gu, B. et al. (Mar. 2, 2018, e-pub. Jan. 25, 2018). "Transcription-Coupled Changes In Nuclear Mobility Of Mammalian Cis-Regulatory Elements," Science 359(6379):1050-1055, 15 pages.

Guo, W. et al. (Mar. 9, 2018). "Splicing Factor RBM20 Regulates Transcriptional Network of Titin Associated and Calcium Handling Genes in The Heart," Int J Biol Sci. 14(4): 369-380.

Guo, W. et al. (May 2012). "RBM20, A Gene For Hereditary Cardiomyopathy, Regulates Titin Splicing," Nat Med. 18(5):766-773, 20 pages.

Guo, Y.E. et al. (Mar. 9, 2018, e-pub. Aug. 7, 2019). "Pol II Phosphorylation Regulates A Switch Between Transcriptional And Splicing Condensates," Nature 572(7770):543-548, 41 pages.

Guy, J. et al. (2011, e-pub. Jun. 29, 2011). "The Role of MeCP2 in the Brain," Annual Review of Cell and Developmental Biology 27(1):631-652.

Hager, K. et al. (Jan. 1, 2007). "Alpha-Lipoic Acid As A New Treatment Option For Alzheimer's Disease—A 48 Months Follow-Up Analysis," Journal Of Neural Transmission Suppl 72:189-193.

Hahn, S. et al. (Nov. 2011). "Transcriptional Regulation In *Saccharomyces cerevisiae*: Transcription Factor Regulation And Function, Mechanisms Of Initiation, And Roles Of Activators And Coactivators," Genetics 189(3):705-736.

Han, T.W. et al. (May 11, 2012). "Cell-Free Formation Of RNA Granules: Bound RNAs Identify Features And Components Of Cellular Assemblies," Cell 149(4):768-779.

(56) References Cited

OTHER PUBLICATIONS

Harmon, T.S. et al. (Nov. 1, 2017). "Intrinsically Disordered Linkers Determine The Interplay Between Phase Separation And Gelation In Multivalent Proteins." Elife 6:e30294, 31 pages.

Hendrich, B. et al. (Nov. 1998). "Identification and Characterization of a Family of Mammalian Methyl-CpG Binding Proteins," Molecular and Cellular Biology 18(11):6538-6547.

Hnisz, D. et al. (Mar. 23, 2017). "A Phase Separation Model for Transcriptional Control," Cell 169(1):13-23, 23 pages.

Hnisz, D. et al. (Nov. 7, 2013, e-pub. Oct. 10, 2013). "Super-enhancers in the control of cell identity and disease," Cell 155(4):934-947.

Hu, L.D. et al. (Aug. 2017, e-pub Jul. 10, 2017) "Screening Novel Stress Granule Regulators From A Natural Compound Library," Protein & Cell 8(8):618-622.

Hyman, A.A. et al. (2014) "Liquid-Liquid Phase Separation In Biology," Annual Review Of Cell And Developmental Biology 30:39-58.

Imbeault, M. et al. (Mar. 23, 2017). "KRAB Zine-Finger Proteins Contribute To The Evolution Of Gene Regulatory Networks," Nature 543(7646):550-554.

Zamudio, A.V. et al. (Dec. 5, 2015). "Mediator Condensates Localize Signaling Factors to Key Cell Identity Gene," Mol Cell 76(5):P753-766.E6.

International Search Report and Written Opinion of the International Searching Authority dated Jan. 27, 2020, for International Patent Application No. PCT/EP2019/077818, filed Oct. 14, 2019, 12 pages.

International Search Report and Written Opinion of the International Searching Authority dated Sep. 23, 2019, for International Patent Application No. PCT/US2019/023694, filed Mar. 22, 2019, 16 pages.

Ip, J.P.K. et al. (Jun. 2018, e-pub. Mar. 6, 2019). "Rett Syndrome: Insights Into Genetic, Molecular And Circuit Mechanisms," Nature Reviews Neuroscience 19(6):368-382, 36 pages.

Janicki, S.M. et al. (Mar. 5, 2004). "From Silencing To Gene Expression: Real-Time Analysis In Single Cells," Cell 116(5):683-698.

Kang, Y.K. et al. (Mar. 5, 2002). "The TRAP/Mediator Coactivator Complex Interacts Directly With Estrogen Receptors Alpha And Beta Through The TRAP220 Subunit And Directly Enhances Estrogen Receptor Function In Vitro," Proc Natl Acad Sci U.S.A. 99(5):2642-2647.

Kato, M. et al. (May 11, 2012). "Cell-Free Formation Of RNA Granules: Low Complexity Sequence Domains Form Dynamic Fibers Within Hydrogels." Cell 149(4):753-767.

Kornberg, R.D. (May 2005). "Mediator And The Mechanism Of Transcriptional Activation," Trends in Biochemical Sciences 30(5):235-239.

Kwon, I. et al. (Nov. 21, 2013). "Phosphorylation-Regulated Binding of RNA Polymerase II to Fibrous Polymers of Low-Complexity Domains," Cell 155(5):1049-1060.

Lachner, M. et al. (Mar. 2001). "Methylation Of Histone H3 Lysine 9 Creates A Binding Site For HP1 Proteins," Nature 410(6824):116-120.

Lambert, S.A. et al. (Feb. 8, 2018). "The Human Transcription Factors," Cell 172(4):650-665.

Larson, A.G. et al. (Jul. 13, 2017). "Liquid Droplet Formation By HP1α Suggests A Role For Phase Separation In Heterochromatin," Nature 547(7662):236-240, 29 pages.

Lei, J.T. et al. (Aug. 7, 2018). "Functional Annotation of ESR1 Gene Fusions in Estrogen Receptor-Positive Breast Cancer," Cell Rep 24(6):1434-1444.

Leroi, I. et al. (Oct. 25, 2006, e-pub. Jun. 27, 2006). "Non-Dopaminergic Treatment of Cognitive Impairment and Dementia in Parkinson's Disease: A Review," Journal Of Neurological Sciences 248(1-2):104-114.

Lewis, J.D. et al. (Jun. 12, 1992). "Purification, Sequence, And Cellular Localization Of A Novel Chromosomal Protein That Binds To Methylated DNA," Cell 69(6):905-914.

Li, P. et al. (Mar. 15, 2012). "Phase Transitions In The Assembly Of Multivalent Signalling Proteins." Nature 483(7389):336-340, 13 pages.

Li, S. et al. (2013, e-pub Jan. 9, 2013). "Rbm20 Regulates Titin Alternative Splicing As A Splicing Repressor," Nucleic Acids Research 41(4):2659-2672.

Li, X-H. et al. (May 1, 2018, e-pub. Feb. 12, 2018). "Function And Regulation Of Phase-Separated Biological Condensates," Biochemistry 57(17):2452-2461.

Lin, Y et al. (Oct. 15, 2015). "Formation and Maturation of Phase-Separated Liquid Droplets by RNA-Binding Proteins," Mol. Cell 60(2):208-219.

Lin, Y. et al. (Oct. 20, 2016)."Toxic PR Poly-Dipeptides Encoded By The C9orf72 Repeat Expansion Target LC Domain Polymers," Cell 167(3):789-802.

Liss, M. et al. (Jun. 11, 2018). "Drug Discovery With An RBM20 Dependent Titin Splice Reporter Identifies Cardenolides As Lead Structures To Improve Cardiac Filling," PloS One 13(6): e0198492, 1-19.

Loven, J. et al. (Apr. 11, 2013). "Selective Inhibition Of Tumor Oncogenes By Disruption Of Super-Enhancers," Cell 153(2):320-334, 27 pages.

Lyst, M.J. et al. (May 2015). "Rett Syndrome: A Complex Disorder With Simple Roots. Nature Reviews Genetics," 16(5):261-274.

Macarron, R. et al. (2009, e-pub Jun. 5, 2009). "Design And Implementation Of High-Throughput Screening Assays," in High Throughput Screening, Janzen W., Bernasconi P. (eds) Humana Press: Totowa, NJ, vol. 565, 1-32., 12 pages (Abstract only).

Mackenzie, I.R. et al. (Aug. 16, 2017): "TIAI Mutations in Amyotrophic Lateral Sclerosis and Frontotemporal Dementia Promote Phase Separation and Alter Stress Granule Dynamics," Neuron 95(4):808-816.

Maharana, S. et al. (Mar. 25, 2018, e-pub. Apr. 12, 2018). "RNA Buffers The Phase Separation Behavior Of Prion-Like RNA-Binding Proteins," Science 360(6391):918-921.

Malik, S. et al. (Oct. 13, 2010). "The Metazoan Mediator Co-Activator Complex As An Integrative Hub For Transcriptional Regulation," Nature Reviews Genetics 11(11) 761-772, 23 pages.

Mangelsdorf, I. et al. (Jan. 1, 2017, e-pub Jun. 12, 2017). "Healing of Amyotrophic Lateral Sclerosis: A Case Report," Complementary Medicine Research 24(3):175-181.

Mansour, M.R. et al. (Dec. 12, 2014, e-pub Jan. 20, 2016). "An Oncogenic Super-Enhancer Formed Through Somatic Mutation Of A Noncoding Intergenic Element," Science 346(6215):1373-1377, 11 pages.

Meehan, R.R. et al. (1992). "Characterization of Mecp2, a Vertebrate DNA-Binding Protein With Affinity for Methylated DNA," Nucleic Acids Research 20(19):5085-5092.

Mitchell, P.J. et al. (Jul. 28, 1989). "Transcriptional Regulation In Mammalian Cells By Sequence-Specific DNA Binding Proteins," Science 245(4916):371-378.

Muiznieks, L.D. et al. (Nov. 2, 2018). "Role Of Liquid-Liquid Phase Separation In Assembly Of Elastin And Other Extracellular Matrix Proteins," Journal Of Molecular Biology 430(23):4741-4753.

Nagalingam, A. et al. (Apr. 2012, e-pub Feb. 16, 2012). "Med1 Plays A Critical Role In The Development Of Tamoxifen Resistance," Carcinogenesis 33(4):918-930.

Nakano, M. et al. (Apr. 15, 2008). "Inactivation of a Human Kinetochore by Specific Targeting of Chromatin Modifiers," Developmental Cell, 14(4):507-522.

Nan, X. et al. (1993). "Dissection Of The Methyl-Cpg Binding Domain From The Chromosomal Protein Mecp2," Nucleic Acids Research 21(21):4886-4892.

Naumann, M. et al. (Jan. 23, 2018). "Impaired DNA Damage Response Signaling By FUS-NLS Mutations Leads To Neurodegeneration And FUS Aggregate Formation," Nature Communications 9(1):1-17.

Nesbit, C.E. et al. (May 13, 1999). "MYC Oncogenes And Human Neoplastic Disease," Oncogene 18(19):3004-3016.

Nott, T.J. et al. (Mar. 5, 2015). "Phase Transition of a Disordered Nuage Protein Generates Environmentally Responsive Membraneless Organelles," Mol. Cell 57(5):936-947.

(56) References Cited

OTHER PUBLICATIONS

Oates, M.E. et al. (2013, e-pub. Nov. 29, 2012). "$D^2p^2$: Database Of Disordered Protein Predictions," Nucleic Acids Res. 41(D1):D508-D516.

Osborne, C.K. et al. (Feb. 11, 2011). "Mechanisms Of Endocrine Resistance In Breast Cancer," Annu Rev Med 62:233-247, 17 pages.

Ozers, M.S. et al. (Jan. 1, 2005). "Analysis Of Ligand-Dependent Recruitment Of Coactivator Peptides To Estrogen Receptor Using Fluorescence Polarization," Mol Endocrinol 19(1):25-34.

Patel, A. et al. (Aug. 27, 2015). "A Liquid-to-Solid Phase Transition of the ALS Protein Accelerated by Disease Mutation" Cell 162:1066-1077.

Patel, A. et al. (May 19, 2017). "ATP As A Biological Hydrotrope," Science 356(6339):753-756.

Patel, B.P. et al. (Dec. 1, 2009). "Nutritional And Exercise-Based Interventions In The Treatment Of Amyotrophic Lateral Sclerosis," Clinical Nutrition 28(6):604-617.

Pessina, F. et al. (Oct. 2019). "Functional Transcription Promoters At DNA Double-Strand Breaks Mediate RNA-Driven Phase Separation Of Damage-Response Factors," Nature Cell Biology 21(10):1286-1299, 29 pages.

Plys, A.J. et al. (Jul. 1, 2019). "Phase Separation Of Polycomb-Repressive Complex 1 Is Governed By A Charged Disordered Region Of CBX2." Genes & Development 33(13-14):799-813.

Posey, A.E. et al. (Mar. 9, 2018, e-pub. Jan. 22, 2018). "Profilin Reduces Aggregation And Phase Separation Of Huntingtin N-Terminal Fragments By Preferentially Binding To Soluble Monomers And Oligomers," Journal of Biological Chemistry 293(10):3734-3746.

Potenza, E. et al. (Oct. 31, 2014). "MobiDB 2.0: An Improved Database Of Intrinsically Disordered And Mobile Proteins," Nucleic Acids Res. 43(D1):D315-D320.

Rahman, S. et al. (Jun. 15, 2017). "Activation Of The LMO2 Oncogene Through A Somatically Acquired Neomorphic Promoter In T-Cell Acute Lymphoblastic Leukemia," Blood 129(24):3221-3226.

Robb, C.M. et al. (Jul. 4, 2017). "Chemically Induced Degradation Of CDK9 By A Proteolysis Targeting Chimera (PROTAC)," Chem Commun (Camb). 53(54):7577-7580, 12 pages.

Roberts, S.G.E. (Aug. 2000). "Mechanisms Of Action Of Transcription Activation And Repression Domains," Cell. Mol. Life Sci. 57(8-9):1149-1160.

Roe, J. S. et al. (Aug. 24, 2017). "Enhancer Reprogramming Promotes Pancreatic Cancer Metastasis," Cell 170(5):875-888, e820.

Sabari, B.R. et al. (Jul. 27, 2018, e-pub Jun. 21, 2018). "Coactivator Condensation At Super-Enhancers Links Phase Separation And Gene Control," Science, 361(6400): eaar3958, 1-24.

Saha, S. et al. (Sep. 8, 2016, e-pub. Sep. 1, 2016). "Polar Positioning Of Phase-Separated Liquid Compartments In Cells Regulated By An Mma Competition Mechanism," 166(6):1572-1584.

Sakamoto, K.M. et al. (Jul. 17, 2001). "Protacs: Chimeric Molecules That Target Proteins To The Skp1-Cullin-F Box Complex For Ubiquitination And Degradation," Proceedings of the National Academy of Sciences 98(15):8554-8559.

Sever, R. et al. (Mar. 1, 2013). "Signaling By Nuclear Receptors," Cold Harbor Perspectives in Biology 5(3):1-4.

Shang, Y. et al. (Dec. 8, 2000). "Cofactor Dynamics And Sufficiency In Estrogen Receptor-Regulated Transcription," Cell 103(6):843-852.

Shin, Y. et al. (Sep. 22, 2017). "Liquid Phase Condensation In Cell Physiology And Disease," Science 357(6357):eaaf4382, 13 pages.

Shrinivas, K. et al. (Dec. 17, 2018). "Enhancer Features That Drive Formation Of Transcriptional Condensates," Molecular Cell 75(3):549-561, 28 pages.

Sigler, P.B. (May 19, 1988). "Acid Blobs And Negative Noodles," Nature 333(6170):210-212.

Skene, P.J. et al. (Feb. 26, 2010). "Neuronal MeCP2 Is Expressed at Near Histone-Octamer Levels and Globally Alters the Chromatin State," Molecular Cell 37(4):457-468.

Smith, R. et al. (2016). "Raman Spectroscopy: An Evolving Technique For Live Cell Studies," Analyst 141(12):3590-3600.

Soufi, A. et al. (Nov. 21, 2012). "Facilitators And Impediments Of The Pluripotency Reprogramming Factors' Initial Engagement With The Genome," Cell 151(5):994-1004.

Staby, L. et al. (Aug. 2017). "Eukaryotic Transcription Factors: Paradigms Of Protein Intrinsic Disorder," Biochem. J. 474(15):2509-2532.

Strom, A.R. et al. (Jul. 13, 2017). "Phase Separation Drives Heterochromatin Domain Formation," Nature 547 (7662):241-245, 19 pages.

Tate, P. et al. (Feb. 1996). "The Methyl-Cpg Binding Protein Mecp2 Is Essential For Embryonic Development In The Mouse," Nat Genet 12(2):205-208.

Triezenberg, S.J. (Apr. 1995). "Structure And Function Of Transcriptional Activation Domains," Curr. Opin. Genet. Dev. 5(2):190-196.

Tsai, A. et al. (Nov. 2, 2017). "Nuclear Microenvironments Modulate Transcription From Low-Affinity Enhancers," Elife 6:e28975, 18 pages.

Tuttle, L.M. et al. (Mar. 20, 2018). "Gcn4-Mediator Specificity Is Mediated By A Large And Dynamic Fuzzy Protein-Protein Complex," Cell Rep. 22(12):3251-3264.

U.S. Appl. No. 16/653,874, filed Oct. 15, 2019, for Hyman et al.(U.S. Patent Application is not submitted herewith pursuant to the waiver of 37 C.F.R. § 1.98(a)(2)(iii) issued by the Office dated Sep. 21, 2004.).

Van Esch, H. et al. (Sep. 2005, e-pub Jul. 29, 2005). "Duplication of the MECP2 Region Is a Frequent Cause of Severe Mental Retardation and Progressive Neurological Symptoms in Males," The American Journal of Human Genetics 77(3):442-453.

Wakefield, R.I.D. et al. (Sep. 3, 1999). "The Solution Structure Of The Domain From Mecp2 That Binds To Methylated DNA," Journal of Molecular Biology 291(5):1055-1065.

Waks, A.G. et al. (Jan. 22, 2019). "Breast Cancer Treatment: A Review," JAMA 321(3):288-300.

Wang, Y. et al. (Sep. 24, 2015). "CDK7-Dependent Transcriptional Addiction In Triple-Negative Breast Cancer," Cell 163(1):174-186.

Wang, J. et al. (May 2016). "New Insights into the Regulation of Heterochromatin," Trends in Genetics 32(5):284-294, 19 pages.

Wang, T. et al. (2018, e-pub. May 26, 2018). "α-Lipoic Acid Attenuates Oxidative Stress And Neurotoxicity Via The ERK/Akt-Dependent Pathway In The Mutant hSOD1 Related Drosophila Model And The NSC34 Cell Line Of Amyotrophic Lateral Sclerosis," Brain Research Bulletin 140(26):299-310.

Wegmann, S. et al. (Apr. 3, 2018, e-pub. Feb. 22, 2018). "Tau Protein Liquid-Liquid Phase Separation Can Initiate Tau Aggregation," The EMBO Journal 37(7):e98049, 21 pages.

Wheeler, R.J. et al. (Dec. 15, 2017). "M128: Small Molecules For Modulating Protein Driven Liquid-Liquid Phase Separation In Neurodegenerative Disease," Molecular Biology of the Cell; Annual Joint Meeting of American Society for Cell Biology/European Molecular Biology Organization (ASCB/EMBO), American Society for Cell Biology: Philadelphia, PA, 28(26):M128, 2 pages (Abstract only).

Wheeler, R.J. et al. (Aug. 21, 2019) "Small Molecules For Modulating Protein Driven Liquid-Liquid Phase Separation In Treating Neurodegenerative Disease," BioRxiv 721001,48 pages.

Wheeler, R.J. et al. (May 26, 2018). "Controlling Compartmentalization By Non-Membrane-Bound Organelles," Philosophical Transactions of the Royal Society B: Biological Sciences 373(1747):20170193, 9 pages.

Winter, G.E. et al. (Jun. 19, 2015). "Selective Target Protein Degradation via Phthalimide Conjugation," Science 348(6241):1376-1381, 13 pages.

Andreassen, O.A. (Apr. 2001). "Effects Of An Inhibitor Of Poly(ADP-Ribose) Polymerase, Desmethylselegiline, Trientine, And Lipoic Acid In Transgenic ALS Mice," Exp Neurol. 168(2):419-424.

Bailey, J.K. et al. (2017, e-pub. Aug. 9, 2017) "Nucleic Acid Binding Proteins Affect The Subcellular Distribution Of Phosphorothioate Antisense Oligonucleotides." Nucleic Acids Research 45(18):10649-10671.

(56) References Cited

OTHER PUBLICATIONS

Basturea, G.N. et al. (Jul. 1, 2019). "Biological Condensates," Material Methods 9, 17 pages.
Bracha, D. et al. (Nov. 29, 2018) "Mapping Local And Global Liquid Phase Behavior In Living Cells Using Photo-Oligomerizable Seeds," Cell 175(6):1467-1480.
Cai, D. et al. (Feb. 10, 2021). "Biomolecular Condensates and Their Links to Cancer Progression", Trends in Biochemical Sciences 46(7):535-549.
Caicedo, J. C. et al. (Sep. 2019, e-pub. Jul. 16, 2019). "Evaluation of Deep Learning Strategies for Nucleus Segmentation in Fluorescence Images," Cytometry, Part A: the journal of the International Society for Analytical Cytology 95(9):952-965.
Cooper, M.S. et al. (Feb. 1, 2010, e-pub Sep. 5, 2009). "Visualizing Green Oil In Live Algal Cells", Journal of Bioscience and Bioengineering 109(2):198-201.
Cuccarese, M.F. et al. (2020). "Functional Immune Mapping With Deep-Learning Enabled Phenomics Applied To Immunomodulatory And COVID-19 Drug Discovery," bioRxiv, 24 pages.
Davies, N. M. et al. (2018, e-pub. Jul. 12, 2018). "Reading Mendelian Randomisation Studies: A Guide, Glossary, And Checklist For Clinicians," BMJ 362(k601):1-11.
Dolgin, E. (Feb. 9, 2021). "Drug Startups Coalesce Around Condensates", Nature Biotechnology 39(2):123-125.
Finucane, H.K. et al. (Apr. 2018). "Heritability Enrichment Of Specifically Expressed Genes Identifies Disease-Relevant Tissues And Cell Types," Nat Genet. 50(4):621-629.
Gill, S.J. et al. (Jun. 25, 1980). "Ligand-Linked Phase Equilibria Of Sickle Cell Hemoglobin," J Mol Biol. 140(2):299-312.
Guo, W. et al. (Feb. 10, 2018). "RBM20, A Potential Target For Treatment Of Cardiomyopathy Via Titin Isoform Switching," Biophysical Reviews 10(1):15-25.
Handoko, L. et al. (Apr. 3, 2018, e-pub. Aug. 6, 2018). "JQ1 Affects BRD2-Dependent And Independent Transcription Regulation Without Disrupting H4-Hyperacetylated Chromatin States," Epigenetics 13(4):410-431.
Huang, H. (Jul. 13, 2017). "Fine-Mapping Inflammatory Bowel Disease Loci To Single-Variant Resolution," Nature 547(7662):173-178.
International Preliminary Report on Patentability dated Apr. 14, 2021 for Patent Application No. PCT/EP2019/077818, filed Oct. 14, 2019, 8 pages.
International Preliminary Report on Patentability dated Aug. 10, 2021 for Patent Application No. PCT/US2020/017333, filed Feb. 7, 2020, 7 pages.
International Preliminary Report on Patentability dated Aug. 25, 2021 for Patent Application No. PCT/US2020/015329, filed Jan. 28, 2020, 6 pages.
International Preliminary Report on Patentability dated Mar. 15, 2022 for Patent Application No. PCT/US2020/051331, filed Sep. 17, 2020, 11 pages.
International Preliminary Report On Patentability, dated Nov. 16, 2021, for PCT Application No. PCT/US2020/033295, filed on May 15, 2020, 13 pages.
International Preliminary Report On Patentability, dated Sep. 29, 2020, for PCT Application No. PCT/US2019/023694, filed on Mar. 22, 2019, 11 pages.
International Search Report and Written Opinion of the International Searching Authority dated Apr. 2, 2020, for International Application No. PCT/US2020/015329, filed Jan. 28, 2020, 9 pages.
International Search Report and Written Opinion of the International Searching Authority dated Apr. 23, 2020, for International Application No. PCT/EP2019/077818, filed Oct. 14, 2019, 10 pages.
International Search Report and Written Opinion of the International Searching Authority dated Jul. 3, 2020, for International Application No. PCT/US2020/017333, filed Feb. 7, 2020, 10 pages.
International Search Report and Written Opinion of the International Searching Authority dated Jul. 25, 2022, for International Application No. PCT/US2022/018311, filed Mar. 1, 2022, 23 pages.
International Search Report and Written Opinion of the International Searching Authority dated Jul. 29, 2020, for International Application No. PCT/US2020/033295, filed May 15, 2020, 17 pages.
International Search Report and Written Opinion of the International Searching Authority dated Mar. 28, 2022, for International Application No. PCT/US2021/045592, filed Aug. 11, 2021, 48 pages.
International Search Report and Written Opinion of the International Searching Authority dated May 17, 2022, for International Application No. PCT/US2022/018282, filed Mar. 1, 2022, 18 pages.
International Search Report and Written Opinion of the International Searching Authority dated Nov. 26, 2020, for International Application No. PCT/US2020/051331, filed Sep. 17, 2020, 16 pages.
Invitation to Pay Additional Fees dated Dec. 14, 2021, for International Application No. PCT/US2021/045592, filed Aug. 11, 2021, 15 pages.
Invitation to Pay Additional Fees dated Jun. 1, 2022, for International Application No. PCT/US2022/018311, filed Mar. 1, 2022, 13 pages.
Jain, A. et al. (Jun. 8, 2017). "RNA Phase Transitions In Repeat Expansion Disorders," Nature 546(7657):243-247.
Klein, I.A. et al. (Jun. 19, 2020). "Partitioning Of Cancer Therapeutics In Nuclear Condensates," Science 368(6497):1386-1392.
Kraus, O. Z., et al. (2016). "Classifying And Segmenting Microscopy Images With Deep Multiple Instance Learning," Bioinformatics 32(12):i52-i59.
Lanni, E.J. et al. (Aug. 1, 2012, e-pub Aug. 30, 2013). "Mass Spectrometry Imaging And Profiling Of Single Cells," Journal of Proteomics 75(16):5036-5051.
Lau, M. S. et al. (Mar. 10, 2017). "Mutation Of A Nucleosome Compaction Region Disrupts Polycomb-Mediated Axial Patterning," Science 355(6329):1081-1084.
Lee, T.H. et al. (2017, e-pub. Jul. 17, 2017). "Molecular Mechanism of PD-1/PD-L1 Blockade via Anti-PD-L1 Antibodies Atezolizumb and Durvalumab," Scientific Reports 7(1):1-12.
Li, C.H et al. (Oct. 2020, e-pub. Jul. 22, 2020). "Mecp2 Links Heterochromatin Condensates And Neurodevelopmental Disease," Nature 586(7829):440-444.
Lowe, D. (Aug. 6, 2019). "A Condensate-Modifying Compound, Put to the Test Science AAAS", Biological News (science.erg), 4 pages, as retrieved from https://www.science.org/content/blog-pest/condensate-modifying-compound-put-test.
Mahajan, A. et al. (Nov. 2018, e-pub. Dec. 10, 2018). "Fine-Mapping Type 2 Diabetes Loci To Single-Variant Resolution Using High-Density Imputation And Islet-Specific Epigenome Maps," Nature Genetics 50(11):1505-1513.
Martin, E.W. et al. (Feb. 7, 2020). "Valence And Patterning Of Aromatic Residues Determine The Phase Behavior Of Prion-Like Domains," Science 367(6478):694-699.
Mateju, D.E. et al. (Jun. 14, 2017, e-pub. Apr. 4, 2017). "An Aberrant Phase Transition Of Stress Granules Triggered By Misfolded Protein And Prevented By Chaperone Function", The Embo Journal 36(12):1669-1687.
Mcquin, C. et al. (Jul. 3, 2018). "Cellprofiler 3.0: Next-Generation Image Processing For Biology," Plos Biology 16(7):e2005970, 17 pages.
Mitrea, D.M. et al. (Feb. 26, 2018). "Self-Interaction Of Npml Modulates Multiple Mechanisms Of Liquid-Liquid Phase Separation," Nature Communications 9(1):1-13.
Mullard, A. et al. (May 1, 2019). "Biomolecular Condensates Pique Drug Discovery Curiosity", Nature Reviews 18:324-326.
Murayama, R. et al. (2018, e-pub Jun. 12, 2018). "Phosphorylation Of The RSRSP Stretch Is Critical For Splicing Regulation By RNA-Binding Motif Protein 20 (RBM20) Through Nuclear Localization," Scientific Reports 8(1):1-14.
Nabet, B, et al. (May 2018, e-pub Dec. 17, 2018). "The Dtag System For Immediate And Target-Specific Protein Degradation," Nature Chemical Biology 14(5):431-441.
Pers, T. H. et al. (Jan. 19, 2015). "Biological Interpretation Of Genome-Wide Association Studies Using Predicted Gene Functions," Nature Communications 6(1):1-9.

(56) References Cited

OTHER PUBLICATIONS

Qi, G. et al. (2019). "Mendelian Randomization Analysis Using Mixture Models For Robust And Efficient Estimation Of Causal Effects," Nature Communications 10(1):1-10.
Riback, J.A. et al. (2020, e-pub May 6, 2020). "Composition-Dependent Thermodynamics Of Intracellular Phase Separation," Nature 581(7807):209-214.
Riback, J.A. et al. (Oct. 22, 2019). "Composition Dependent Phase Separation Underlies Directional Flux Through The Nucleolus," bioRxiv 809210:26 pages.
Rossin, E. J. et al. (Jan. 13, 2011). "Proteins encoded in genomic regions associated with immune-mediated disease physically interact and suggest underlying biology," PLoS genetics 7(1):e1001273, 13 pages.
Ruff, K.M. et al. (Mar. 9, 2021). "Ligand Effects On Phase Separation Of Multivalent Macromolecules," Proc Natl Acad Sci U S A. 118(10):e2017184118, 10 pages.
Schneider, J.W. et al. (Nov. 2020, e-pub. Nov. 13, 2020). "Dysregulated Ribonucleoprotein Granules Promote Cardiomyopathy In RBM20 Gene-Edited Pigs," Nature Medicine 26(11):1788-1800, 2 pages. (Abstract Only).
Tisel, W.A. et al. (Oct. 10, 1980). "Polyphasic Linkage Between Protein Solubility And Ligand Binding In The Hemoglobin-Polyethylene Glycol System," J Biol Chem 255(19):8975-8978.
Tulpule, A. et al. (Apr. 9, 2020). "Kinase-Mediated RAS Signaling Via Membraneless Cytoplasmic Protein Granules," Biorxiv 704312:48 pages.
U.S. Appl. No. 17/040,967, filed Mar. 22, 2019, for Young et al.(U.S. Patent Application is not submitted herewith pursuant to the waiver of 37 C.F.R. § 1.98(a)(2)(iii) issued by the Office dated Sep. 21, 2004.).
U.S. Appl. No. 17/721,054, filed Apr. 14, 2022, for Szewczak et al.(U.S. Patent Application is not submitted herewith pursuant to the waiver of 37 C.F.R. § 1.98(a)(2)(iii) issued by the Office dated Sep. 21, 2004.).
U.S. Appl. No. 17/761,545, filed Mar. 17, 2022, for Patel et al.(U.S. Patent Application is not submitted herewith pursuant to the waiver of 37 C.F.R. § 1.98(a)(2)(iii) issued by the Office dated Sep. 21, 2004.).
Vuignier, K. et al. (Sep. 2010). "Drug-Protein Binding: A Critical Review Of Analytical Tools," Anal Bioanal Chem. 398(1):53-66.
Vujkovic, M. et al. (Jul. 2020, e-pub. Jun. 15, 2020). "Discovery Of 318 New Risk Loci For Type 2 Diabetes And Related Vascular Outcomes Among 1.4 Million Participants In A Multi-Ancestry Meta-Analysis," Nature Genetics 52(7):680-691.
Wan, L. et al. (Jan. 2020, e-pub. Mar. 9, 2020). "Impaired Cell Fate Through Gain-Of-Function Mutations In A Chromatin Reader," Nature 577(7788):121-126.
Watanabe, K. et al. (Nov. 28, 2017). "Functional Mapping And Annotation Of Genetic Associations With FUMA," Nat Commun. 8(1):1826, 1-11.
Weeks, E. M. et al. (2020). "Leveraging Polygenic Enrichments Of Gene Features To Predict Genes Underlying Complex Traits And Diseases," MedRxiv, 24 pages.
White, M. R. et al. (May 16, 2019). "C9orf72 Poly (PR) Dipeptide Repeats Disturb Biomolecular Phase Separation And Disrupt Nucleolar Function," Molecular Cell 74(4):713-728.
Yu, C. et al. (May 2021, e-pub. Sep. 2, 2020). "Proteome-Scale Analysis Of Phase-Separated Proteins In Immunofluorescence Images," Briefings In Bioinformatics 22(3):bbaa187, 15 pages.
Zhang, P. et al. (Jun. 18, 2018). "Optogranules Reveal The Evolution Of Stress Granules To ALS-FTD Pathology," bioRxv 348870, 35 pages, as retrieved from https://www.biorxiv.org/content/biorxiv/early/2018/06/18/348870.full.pdf.
Zhou, M. et al. (Mar. 19, 2020). "Phase-Separated Condensate-Aided Enrichment Of Biomolecular Interactions For High-Throughput Drug Screening In Test Tubes", Journal of Biological Chemistry 295(33):11420-11434.
Zhu, C. et al. (Feb. 1, 2015, e-pub Jan. 8, 2015). "RBM20 Is An Essential Factor For Thyroid Hormone-Regulated Titin Isoform Transition," Journal Of Molecular Cell Biology 7(1):88-90.

* cited by examiner

METHODS OF CHARACTERIZING CONDENSATE-ASSOCIATED CHARACTERISTICS OF COMPOUNDS AND USES THEREOF

CROSS-REFERENCE TO RELATED APPLICATIONS

This application claims priority benefit to U.S. Provisional Patent Application No. 62/803,365, filed on Feb. 8, 2019, and U.S. Provisional Patent Application No. 62/866,526, filed on Jun. 25, 2019, the disclosure of each of which is hereby incorporated herein by reference in its entirety.

TECHNICAL FIELD

The present invention relates to the field of biological condensates.

BACKGROUND

In addition to membrane-bound organelles, such as mitochondria, lysosomes, and the endoplasmic reticulum, cells contain distinct sub-compartments that do not comprise a membrane between them and their immediate surrounding solution. Numerous of these membrane-less molecular assemblies have been shown to be formed through a process termed liquid-liquid phase separation or condensation. During this process, a solution comprising biological macromolecules separates into different phases, a condensate that is enriched in some of those macromolecules and a surrounding phase that is relatively depleted in those macromolecules. A number of cellular condensates have been recognized. In addition, phase-separated condensates can be formed outside of the cell, such as in solution or extracellularly (Alberti et al., *J Mol Biol,* 430(23), 2018, 4806-4820; Muiznieks et al., *J Mol Biol,* 430(23), 2018, 4741-4753). However, little or nothing is known about the mechanisms governing the partitioning of compounds into or the exclusion of compounds from condensates or the differences in the partitioning of compounds among various condensates.

Various condensates are known to be important for modulating cellular processes. For example, a condensate can bring together molecules at an elevated concentration to accelerate reactions inside the condensate or can sequester molecules in the condensate, reducing their concentration in the surrounding medium. Aberrant condensate function has also been implicated in various human diseases, such as neurodegenerative and proliferative diseases (Naumann et al., *Nat Commun,* 9(1), 2018, 335; Wegmann et al., *EMBO J,* 37(7), 2018, e98049; Aguzzi et al., *Trends Cell Biol,* 26(7), 2016, 547-558). However, in addition to the lack of understanding of the mechanisms governing condensate partitioning of compounds, there is little or nothing known regarding how to identify test compounds that interact with condensates, how to design compounds to improve interactions with condensates, and how such information can be used to improve treatment of diseases.

All references cited herein, including patent applications and publications, are incorporated by reference in their entirety.

BRIEF SUMMARY

In some aspects, provided herein are methods of determining a partition characteristic of a test compound in a target condensate, the method comprising: (a) combining the test compound and a composition comprising the target condensate and an extra-condensate solution; (b) determining the amount of the test compound in the target condensate, thereby determining the partition characteristic of the test compound in the target condensate. In some embodiments, the methods further comprise causing the formation of the target condensate prior to step (a).

In some aspects, provided herein are methods of determining a partition characteristic of a test compound in a target condensate, the method comprising: (a) adding the test compound to a composition comprising a target condensate and an extra-condensate solution; and (b) determining the amount of the test compound in the target condensate, thereby determining the partition characteristic of the test compound in the target condensate. In some embodiments, the methods further comprise causing the formation of the target condensate prior to step (a).

In some aspects, provided herein are methods of determining a partition characteristic of a test compound in a target condensate, the method comprising: (a) causing the formation of the target condensate in the presence of the test compound to obtain a composition comprising the target condensate and an extra-condensate solution; and (b) determining the amount of the test compound in the target condensate, thereby determining the partition characteristic of the test compound in the target condensate.

In some aspects, provided herein are methods of determining a partition characteristic of a test compound in a target condensate, the method comprising: (a) adding the test compound to a composition comprising precursor molecules; (b) causing the formation of the target condensate to obtain a composition comprising the target condensate and an extra-condensate solution; and (c) determining the amount of the test compound in the target condensate, thereby determining the partition characteristic of the test compound in the target condensate. In some embodiments, the methods further comprise combining the test compound and a precursor composition comprising precursor molecules prior to step (a). In some embodiments, the methods further comprise adding the test compound to a precursor composition comprising precursor molecules prior to step (a).

In some embodiments, the methods further comprise determining the amount of the test compound in the extra-condensate solution. In some embodiments, the amount of the test compound in the target condensate is determined prior to, simultaneously with, or after the amount of the test compound in the extra-condensate solution is determined. In some embodiments, the methods further comprise determining the ratio of the amount of test compound in the target condensate and the amount of test compound in the extra-condensate solution. In some embodiments, the methods further comprise separating the target condensate from the extra-condensate solution. In some embodiments, the methods further comprise identifying the target condensate prior to determining the amount of test compound in the target condensate.

In some embodiments, dysregulation of the target condensate is associated with a disease. In some embodiments, the methods further comprise characterizing the target condensate by identifying one or more macromolecules comprised therein. In some embodiments, the identifying comprises determining the amount of the one or more macromolecules in the target condensate. In some embodiments, the methods further comprise determining the ratio of the amount of test compound in the target condensate and the amount of the one or more macromolecules in the target condensate. In some embodiments, the target condensate comprises a protein comprising an intrinsically disordered sequence. In some embodiments, the methods further comprise labeling the target condensate in order to visualize the target condensate. In some embodiments, the target condensate is labeled with a radioactive label, a colorimetric label, a chemically-reactive label, or a fluorescent label.

In some embodiments, the composition comprises a cell. In some embodiments, the cell is a microorganism or an animal cell. In some embodiments, the cell comprises a condensate that is determined to be dysregulated. In some embodiments, the cell has one or more features of a neurodegenerative or proliferative disease.

In some embodiments, the target condensate is a cellular condensate. In some embodiments, cellular condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a signaling cluster, a Sam68 nuclear body, a stress granule, or a splicing speckle. In some embodiments, the target condensate is in a cell. In some embodiments, the cell is a microorganism or an animal cell. In some embodiments, the cell has one or more features of a neurodegenerative or proliferative disease. In some embodiments, the extra-condensate solution is intracellular fluid. In some embodiments, the intracellular fluid is cytosol or nucleosol.

In some embodiments, the target condensate is not in a cell. In some embodiments, the target condensate is an extracellular condensate. In some embodiments, the extra-condensate solution is extracellular fluid. In some embodiments, the extracellular fluid is interstitial fluid.

In some embodiments, the method is a cell free assay method. In some embodiments, the composition does not comprise a cell. In some embodiments, the composition comprises one or more of: a macromolecule, a salt, and a buffer.

In some embodiments, the composition comprises two or more target condensates. In some embodiments, the methods further comprise repeating the steps of the method for one or more additional condensates.

In some embodiments, the test compound is small molecule, a polypeptide, or a nucleic acid. In some embodiments, the test compound comprises a test compound label. In some embodiments, the test compound label is a radioactive label, a colorimetric label, a chemically-reactive label, or a fluorescent label. In some embodiments, the test compound label is a fluorescent label. In some embodiments, the amount of the test compound is determined by detecting the test compound label. In some embodiments, the amount of the test compound is determined by mass spectrometry, liquid chromatography, quantitative fluorescent microscopy and spectroscopy, nuclear magnetic resonance spectroscopy, Raman spectroscopy, and/or ultraviolet-visible spectrophotometry.

In some aspects, provided herein are methods of determining the partition characteristics of a plurality of test compounds in a target condensate, the method comprising performing a method of determining the partition characteristic described herein with a plurality of test compounds. In some embodiments, the methods further comprise comparing the partition characteristics of a subset or all of the plurality of test compounds in the target condensate. In some embodiments, the methods further comprise identifying test compounds that have the same or similar partition characteristics in a target condensate. In some embodiments, the methods further comprise identifying a characteristic that a subset or all of the identified test compounds have in common in addition to the same or similar partition characteristics. In some embodiments, the methods further comprise determining the partition characteristic in a target condensate for one or more additional test compounds that comprise the identified characteristic. In some embodiments, the methods further comprise determining the partition characteristic in a target condensate for one or more additional test compounds that do not comprise the identified characteristic.

In some aspects, provided herein are methods of determining a relative partition characteristic of a test compound in a target condensate, the method comprising: (i) determining the partition characteristic of the test compound by performing a method of determining a partition characteristic described herein with the test compound; (ii) determining the partition characteristic of a reference compound by performing a method of determining a partition characteristic described herein with the reference compound; and (iii) calculating the ratio of the partition characteristics determined in (i) and (ii), thereby determining the relative partition characteristic of the test compound in the target condensate. In some embodiments, the test compound comprises a test compound label. In some embodiments, the reference compound is the test compound label.

In some aspects, provided herein are methods of determining relative partition characteristics of a plurality of test compounds in a target condensate, the method comprising: (1) performing a method of determining a relative partition characteristic of a test compound in a target condensate; and (2) repeating steps (i) and (iii) with a plurality of test compounds. In some embodiments, the methods further comprise comparing the relative partition characteristics in the target condensate of a subset or all of the plurality of test compounds. In some embodiments, the methods further comprise identifying test compounds that have the same or similar relative partition characteristics in the target condensate. In some embodiments, the methods further comprise identifying a characteristic that a subset or all of the identified test compounds have in common in addition to the same or similar relative partition characteristics. In some embodiments, the methods further comprise determining the relative partition characteristic in the target condensate for one or more additional test compounds that comprise the identified characteristic. In some embodiments, the methods further comprise determining the relative partition characteristic in the target condensate for one or more additional test compounds that do not comprise the identified characteristic.

In some aspects, provided herein are methods of determining a condensate preference profile of a test compound, the method comprising: (a) determining the partition characteristic of the test compound in a first target condensate according to a method disclosed herein; (b) determining the partition characteristic of the test compound in a second target condensate according to a method disclosed herein; and (c) calculating a ratio of the partition characteristic of the test compound determined in the first target condensate and the second target condensate, thereby determining the condensate preference profile of the test compound. In some embodiments, the first target condensate and the second target condensate are in the same composition. In some embodiments, the first target condensate and the second target condensate are in different compositions. In some embodiments, the partition characteristic of the test compound in the first target condensate is determined prior to, simultaneously with, or after the partition characteristic of the test compound in the second target condensate is determined.

In some aspects, provided herein are methods of determining a condensate preference profile of a test compound, the method comprising: (a) determining the relative partition characteristic of the test compound in a first target condensate according to a method disclosed herein; (b) determining the relative partition characteristic of the test compound in a second target condensate according to a method disclosed herein; and (c) calculating a ratio of the partition characteristic of the test compound determined in the first target condensate and the second target condensate, thereby determining the condensate preference profile of the test compound. In some embodiments, the first target condensate and the second target condensate are in the same composition. In some embodiments, the first target condensate and the second target condensate are in different compositions. In some embodiments, the relative partition characteristic of the test compound in the first target condensate is determined prior to, simultaneously with, or after the relative partition characteristic of the test compound in the second target condensate is determined.

In some aspects, provided herein are methods of determining a condensate preference profile of a test compound, the method comprising: (a) adding the test compound to a composition comprising a first target condensate and a second target condensate; (b) determining the amount of the test compound in the first target condensate; (c) determining the amount of the test compound in the second target condensate; and (d) calculating a ratio of the amount of the test compound determined in the first target condensate and the second target condensate, thereby determining the condensate preference profile of the test compound. In some embodiments, the methods further comprise causing the formation of the first target condensate and/or the second target condensate prior to step (a).

In some aspects, provided herein are methods of determining a condensate preference profile of a test compound, the method comprising: (a) adding the test compound to a composition comprising precursor molecules; (b) causing the formation of a first target condensate and a second target condensate in the composition; (c) determining the amount of the test compound in the first target condensate; (d) determining the amount of the test compound in the second target condensate; and (e) calculating a ratio of the amount the test compounds determined in the first target condensate and the second target condensate, thereby determining the condensate preference profile of the test compound. In some embodiments, the amount of the test compound in the first target condensate is determined prior to, simultaneously with, or after the amount of the test compound in the second target condensate is determined.

In some embodiments, the methods further comprise separating the first target condensate and the second target condensate from the composition. In some embodiments, the methods further comprise identifying the first target condensate and/or the second target condensate prior to determining the amount of test compound in the first condensate and/or the second condensate.

In some embodiments, dysregulation of the first target condensate and/or the second target condensate is associated with a disease. In some embodiments, the methods further comprise characterizing the first target condensate and/or the second target condensate by identifying one or more macromolecules comprised therein. In some embodiments, the methods further comprise labeling the first target condensate and/or the second target condensate in order to visualize the first target condensate and/or the second target condensate. In some embodiments, the methods further comprise labeling the first target condensate and the second target condensate in order to visualize the first condensate target condensate and the second target condensate. In some embodiments, the first target condensate and the second target condensate are labeled with different labels. In some embodiments, the first target condensate and/or the second target condensate are labeled with a radioactive label, a colorimetric label, a chemically-reactive label, or a fluorescent label.

In some embodiments, the composition comprises a cell. In some embodiments, the cell is a microorganism or an animal cell. In some embodiments, the cell comprises a condensate that is determined to be dysregulated. In some embodiments, the cell has one or more features of a neurodegenerative or proliferative disease.

In some embodiments, the first target condensate and/or the second target condensate are cellular condensates. In some embodiments, the first target condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a signaling cluster, a viral condensate, a Sam68 nuclear body, a stress granule, or a splicing speckle. In some embodiments, the second target condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a signaling cluster, a viral condensate, a Sam68 nuclear body, a stress granule, or a splicing speckle. In some embodiments, the first target condensate and/or the second target condensate are in a cell.

In some embodiments, the first target condensate and/or the second target condensate are extracellular condensates.

In some embodiments, the composition does not comprise a cell. In some embodiments, the composition comprises one or more of: a macromolecule, a salt, and a buffer.

In some embodiments, the composition comprises one or more additional target condensates. In some embodiments, the methods further comprise repeating the steps of the method for one or more additional target condensates.

In some aspects, provided herein are methods of determining condensate preference profiles of a plurality of test compounds, the method comprising performing a method of determining a condensate preference profile described herein with a plurality of test compounds. In some embodiments, the methods further comprise comparing condensate preference profiles of a subset or all of the plurality of test compounds. In some embodiments, the methods further comprise identifying test compounds that have the same or similar condensate preference profiles. In some embodiments, the methods further comprise identifying a characteristic that a subset or all of the identified test compounds have in common in addition to the same or similar condensate preference profiles. In some embodiments, the methods further comprise determining the relative partition characteristic for one or more additional test compounds that comprise the identified characteristic. In some embodiments, the methods further comprise determining the relative partition characteristic for one or more additional test compounds that do not comprise the identified characteristic.

In some aspects, provided herein are methods of identifying a compound characteristic associated with partitioning a compound into or out of a condensate, the method comprising: (a) determining partition characteristics of a plurality of test compounds in the target condensate according to a method described herein; (b) comparing the partition characteristics of a subset or all of the plurality of test compounds in the target compound; (c) identifying test compounds that have the same or similar partition characteristics in the target condensate; and (d) identifying a characteristic that a subset or all of the identified test compounds have in common in addition to the same or similar partition characteristics.

In some aspects, provided herein are methods of identifying a compound characteristic associated with partitioning a compound into a condensate, the method comprising: (a) determining partition characteristics of a plurality of test compounds in the target condensate according to a method described herein; (b) comparing the partition characteristics of a subset or all of the plurality of test compounds in the target compound; (c) identifying test compounds that have the same or similar partition characteristics in the target condensate; and (d) identifying a characteristic that a subset or all of the identified test compounds have in common in addition to the same or similar partition characteristics.

In some aspects, provided herein are methods of identifying a compound characteristic associated with partitioning a compound into or out of a condensate, the method comprising: (a) determining relative partition characteristics of a plurality of test compounds in the target condensate according to a method described herein; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics.

In some aspects, provided herein are methods of identifying a compound characteristic associated with partitioning a compound into a condensate, the method comprising: (a) determining relative partition characteristics of a plurality of test compounds in the target condensate according to a method described herein; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics.

In some aspects, provided herein are methods of identifying a compound characteristic associated with partitioning a compound into or out of a condensate, the method comprising: (a) determining condensate preference profiles of a plurality of test compounds according to a method described herein; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles.

In some aspects, provided herein are methods of identifying a compound characteristic associated with partitioning a compound into a condensate, the method comprising: (a) determining condensate preference profiles of a plurality of test compounds according to a method described herein; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles.

In some aspects, provided herein are methods of designing a compound with a desired partition characteristic into or out of a target condensate, the method comprising: (a) determining partition characteristics of a plurality of test compounds in the target condensate according to a method described herein; (b) comparing the partition characteristics of a subset or all of the plurality of test compounds in the target condensate; (c) identifying test compounds that have the same or similar partition characteristics in the target condensate; (d) identifying a characteristic that a subset or all of the identified test compounds have in common in addition to the same or similar partition characteristics; and (e)(i) designing a compound that comprises the identified characteristic; or (ii) designing a compound that does not comprise the identified characteristic, thereby designing a compound with the desired partition characteristic into or out of the target condensate. In some embodiments, designing the compound comprises attaching a moiety that comprises the identified characteristic, thereby conferring the desired partition characteristic to the compound. In some embodiments, designing the compound comprises removing a moiety that comprises the identified characteristic, thereby conferring the desired partition characteristic to the compound. In some embodiments, designing the compound comprises changing a first moiety to a second moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some aspects, provided herein are methods of designing a compound with a desired partition characteristic to a target condensate, the method comprising: (a) determining partition characteristics of a plurality of test compounds in the target condensate according to a method described herein; (b) comparing the partition characteristics of a subset or all of the plurality of test compounds in the target condensate; (c) identifying test compounds that have the same or similar partition characteristics in the target condensate; (d) identifying a characteristic that a subset or all of the identified test compounds have in common in addition to the same or similar partition characteristics; and (e) designing a compound that comprises the identified characteristic. In some embodiments, designing the compound comprises attaching a moiety that comprises the identified characteristic, thereby conferring the desired partition characteristic to the compound. In some embodiments, designing the compound comprises changing a first moiety to a second moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some aspects, provided herein are methods of designing a compound with a desired relative partition characteristic into or out of a target condensate, the method comprising: (a) determining relative partition characteristics of a plurality of test compounds in the target condensate according to a method disclosed herein; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e)(i) designing a compound that comprises the identified characteristic; or (ii) designing a compound that does not comprise the identified characteristic, thereby designing a compound with the desired relative partition characteristic into or out of the target condensate. In some embodiments, designing the compound comprises attaching a moiety that comprises the identified characteristic, thereby conferring the desired relative partition characteristic to the compound. In some embodiments, designing the compound comprises removing a moiety that comprises the identified characteristic, thereby conferring the desired partition characteristic to the compound. In some embodiments, designing the compound comprises changing a first moiety to a second moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some aspects, provided herein are methods of designing a compound with a desired relative partition characteristic, the method comprising: (a) determining relative partition characteristics of a plurality of test compounds in the target condensate according to a method described herein; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e) designing a compound that comprises the identified characteristic. In some embodiments, designing the compound comprises attaching a moiety that comprises the identified characteristic, thereby conferring the desired relative partition characteristic to the compound. In some embodiments, designing the compound comprises changing a first moiety to a second moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some aspects, provided herein are methods of designing a compound with a desired condensate preference profile, the method comprising: (a) determining condensate preference profiles of a plurality of test compounds according to a method disclosed herein; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e)(i) designing a compound that comprises the identified characteristic; or (ii) designing a compound that does not comprise the identified characteristic, thereby designing a compound with the desired condensate preference profile. In some embodiments, the methods further comprise making the compound. In some embodiments, designing the compound comprises attaching a moiety that comprises the identified characteristic, thereby conferring the desired condensate preference profile to the compound. In some embodiments, designing the compound comprises removing a moiety that comprises the identified characteristic, thereby conferring the desired partition characteristic to the compound. In some embodiments, designing the compound comprises changing a first moiety to a second moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some aspects, provided herein are methods of designing a compound with a desired condensate preference profile, the method comprising: (a) determining condensate preference profiles of a plurality of test compounds according to a method described herein; (b) comparing the condensate preference profiles of a subset or all of the plurality of test compounds; (c) identifying test compounds that have the same or similar condensate preference profiles; (d) identifying a characteristic, such as a chemical moiety or motif, that a subset or all of the identified test compounds have in common in addition to the same or similar condensate preference profiles; and (e) designing a compound that comprises the identified characteristic. In some embodiments, designing the compound comprises attaching a moiety that comprises the identified characteristic, thereby conferring the desired condensate preference profile to the compound. In some embodiments, designing the compound comprises changing a first moiety to a second moiety that comprises the identified characteristic, thereby conferring the desired partition characteristic to the compound. In some embodiments, there is provided a plurality of compounds designed by the methods described herein. In some embodiments, the compound is designed, in whole or in part, using an approach comprising a modeling, computer, and/or calculation-based technique, e.g., a bioinformatic, cheminformatic, and/or artificial intelligence (AI)-based technique. In some embodiments, the methods further comprise making the compound.

In some aspects, provided herein are methods of screening a test compound for a desired partition characteristic from a group of candidate compounds, the method comprising: (a) determining a partition characteristic of each of the group of candidate compounds; and (b) identifying the test compound having the desired partition characteristic. In some embodiments, the partition characteristic of each of the group of candidate compounds is determined in vitro. In some embodiments, the test compound has a suitable partition characteristic for being useful for treating a disease in an individual.

In some aspects, provided herein are methods of identifying a test compound useful for treating a disease in an individual in need thereof, the method comprising: (a) identifying a target condensate associated with the disease;

and (b) determining a partition characteristic of a candidate compound in the target condensate, and (c) identifying the test compound having a suitable partition characteristic for being useful for treating the disease.

In some aspects, provided herein are methods of determining a partition characteristic of a test compound in a target condensate, the methods comprising: (a) combining the test compound and a composition comprising the target condensate and an extra-condensate solution; (b) obtaining a reference control; (c) measuring a MS signal of the test compound in the extra-condensate solution, or a portion thereof, using a mass spectrometry technique; (d) measuring a MS signal of the test compound in the reference control, or a portion thereof, using a mass spectrometry technique; and (e) comparing the MS signal of the test compound from the extra-condensate solution and the MS signal of the test compound from the reference control, thereby determining the partition characteristic of the test compound in the target condensate. In some embodiments, the amount of the test compound combined with the composition is 100 nM or less, and the amount of a precursor molecule in the composition, including in the target condensate, is about 5 µM.

In some aspects, provided herein is a library comprising a plurality of compounds, wherein each compound of the plurality of compounds comprises the same moiety comprising a characteristic having a desired partition characteristic.

In some aspects, provided herein is a method of designing a test compound having a desired partition characteristic, the method comprising modifying a precursor of the test compound by attaching a moiety to the compound, wherein the moiety comprises a characteristic having a desired partition characteristic.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects.

DETAILED DESCRIPTION

Figure 1:
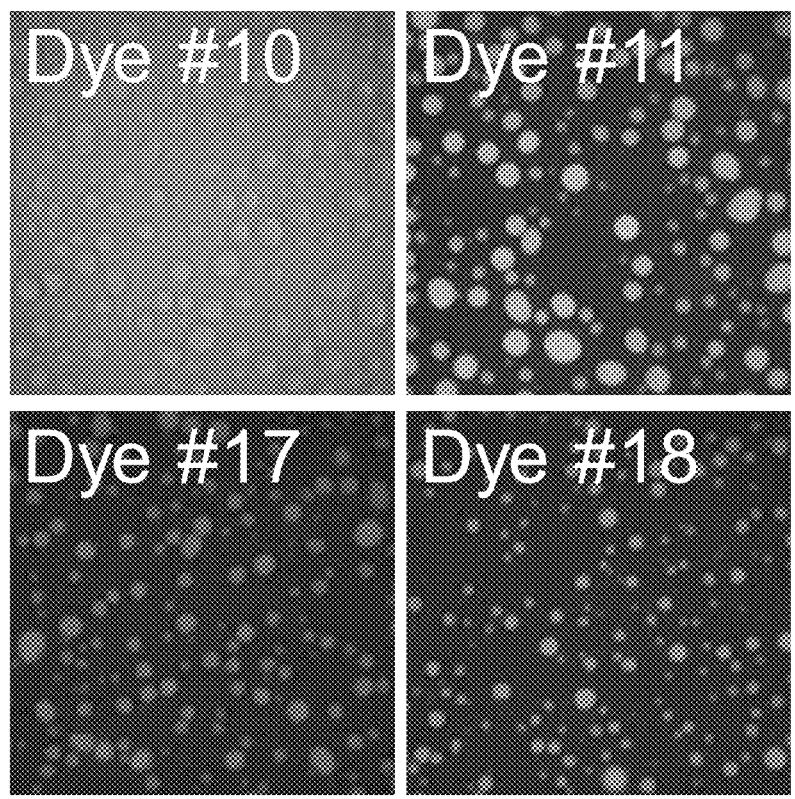
FIG. 1 shows exemplary fluorescent images of dyes partitioning in condensates. Dye #10 is not enriched in the condensate, while other dyes are enriched in the condensate.

The invention includes, in some aspects, methods of assessing, such as characterizing or determining, condensate-associated characteristics of a compound, such as a test compound, and applications thereof.

The disclosure of the present application is based, in part, on the inventors' unique insights of methods of assessing, such as determining or characterizing, condensate-associated characteristics of a compound and that such methods may be useful for, e.g., identifying, characterizing, and developing compounds, or moieties thereof, capable of a desired interaction (including a lack of an interaction) with a condensate. In some embodiments, the desired interaction with a condensate results in a desired biological activity associated with a compound. In some aspects, the disclosure of the present application is based, in part, on the inventors' findings and developments regarding the use of quantitative techniques, such as mass spectrometry, for determining a condensate-associated characteristic of a compound, such as a partition characteristic of a test compound for a target condensate. Such methods allow for, e.g., accurate and reliable determination of a partition characteristic of a test compound for a target condensate in a high-throughput manner that is suitable for use in both simple and complex systems. Additionally, e.g., these methods are hypothesis-free (i.e., do not require a known, labeled compound or condensate, or a component thereof), compatible with a high-degree of compound multiplexing, do not require compound enrichment, do not require compound extraction from a condensate, can be used in homotypic and heterotypic systems, and can be performed with a lower amount of compound and/or condensate precursor macromolecules, which represents a more biologically relevant model and reduces the use of starting materials and reagents. These methods allow for the identification of test compounds, or portions thereof, that can be used to guide further identification and/or design of one or more compounds having a desired partition characteristic, thus providing a method for identifying a target compound with improved potency, therapeutic index, and/or safety. The identification of test compounds, or portions thereof, also enables the advancement of certain drug development application using such knowledge, e.g., the development of privileged libraries of compound having a desired partitioning characteristic, and modeling and/or calculation-based techniques for drug discovery and screening.

As described herein, the methods of assessing condensate-associated characteristics of a compound may be applied to many methods and forms thereof, including methods of determining a partition characteristic of a test compound, methods of determining a relative partition characteristic of a test compound, methods of determining a condensate preference profile of a test compound, methods of identifying a compound characteristic associated with condensate association, methods of designing a compound with a desired condensate association, and methods of identifying a compound useful for treating a disease in an individual. Forms of the methods described herein, include, e.g., assays for: assessing interactions of a single test compound, or a portion thereof, with a single target condensate, assessing interactions of a single test compound, or a portion thereof, with a plurality of target condensates, and assessing interactions of a plurality of test compounds, or a subset thereof, with a single target condensate. As described herein, the inventors' unique insights enable, e.g., identification, development, and optimization of compounds, such as pharmaceutically acceptable compounds, useful for the treatment of a disease in an individual.

Thus, in some aspects, the invention includes methods of determining a partition characteristic of a test compound in a target condensate, the method comprising: (a) adding the test compound to a composition comprising a target condensate and an extra-condensate solution; (b) determining the amount of the test compound in the target condensate, thereby determining the partition characteristic of the test compound in the target condensate.

In other aspects, the invention includes methods of determining a partition characteristic of a test compound in a target condensate, the method comprising: (a) adding the test compound to a composition comprising precursor molecules; (b) causing the formation of the target condensate to obtain a composition comprising the target condensate and an extra-condensate solution; (c) determining the amount of the test compound in the target condensate, thereby determining the partition characteristic of the test compound in the target condensate.

In other aspects, the invention includes methods of determining the partition characteristics of a plurality of test compounds in a target condensate, the method comprising performing any one or more methods described herein using a plurality of test compounds.

In some embodiments, the invention includes methods of identifying a compound characteristic associated with partitioning a compound into a condensate, the method comprising: (a) determining partition characteristics of a plurality of test compounds in the target condensate by performing a method of determining the partition characteristics of a plurality of test compounds in the target condensate; (b) comparing the partition characteristics of a subset or all of the plurality of test compounds in the target condensate; (c) identifying test compounds that have the same or similar partition characteristics in the target condensate; and (d) identifying a characteristic that a subset or all of the identified test compounds have in common in addition to the same or similar partition characteristics. In some embodiments, the invention includes methods of designing a compound with a desired partition characteristic to a target condensate, the method comprising: (a) determining partition characteristics of a plurality of test compounds in the target condensate by performing a method of determining the partition characteristics of a plurality of test compounds in the target condensate; (b) comparing the partition characteristics of a subset or all of the plurality of test compounds in the target condensate; (c) identifying test compounds that have the same or similar partition characteristics in the target condensate; (d) identifying a characteristic that a subset or all of the identified test compounds have in common in addition to the same or similar partition characteristics; and (e) designing a compound that comprises the identified characteristic.

In other aspects, the invention includes methods of determining a relative partition characteristic of a test compound in a target condensate, the method comprising: (i) determining the partition characteristic of the test compound by performing any one or more methods described herein with the test compound; (ii) determining the partition characteristic of a reference compound by performing any one or more methods described herein with the reference compound; and (iii) calculating the ratio of the partition characteristics determined in (i) and (ii), thereby determining the relative partition characteristic of the test compound in the target condensate. In some embodiments, the methods further comprise repeating steps (i) and (iii) with a plurality of test compounds. In some embodiments, the invention includes methods of identifying a compound characteristic associated with partitioning a compound into a target condensate, the method comprising: (a) determining relative partition characteristics of a plurality of test compounds in the target condensate by performing a method of determining a relative partition characteristic of a plurality test compound in a target condensate; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics. In some embodiments, the invention includes methods of designing a compound with a desired relative partition characteristic, the method comprising: (a) determining relative partition characteristics of a plurality of test compounds in the target condensate by performing a method of determining a relative partition characteristic of a plurality test compound in the target condensate; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e) designing a compound that comprises the identified characteristic.

In other aspects, the invention includes methods of determining a condensate preference profile of a test compound, the method comprising: (a) adding the test compound to a composition comprising a first target condensate and a second target condensate; (b) determining the amount of the test compound in the first target condensate; (c) determining the amount of the test compound in the second target condensate; and (d) calculating a ratio of the amount of the test compound determined in the first target condensate and the second target condensate, thereby determining the condensate preference profile of the test compound.

In other aspects, the invention includes methods of determining a condensate preference profile of a test compound, the method comprising: (a) adding the test compound to a composition comprising precursor molecules; (b) causing the formation of a first target condensate and a second target condensate in the composition; (c) determining the amount of the test compound in the first target condensate; (d) determining the amount of the test compound in the second target condensate; (e) calculating a ratio of the amount the test compounds determined in the first target condensate and the second target condensate, thereby determining the condensate preference profile of the test compound.

In other aspects, the invention includes methods of determining condensate preference profiles of a plurality of test compounds, the method comprising performing any one or more of the methods described herein for determining a condensate preference profile of a test compound using a plurality of test compounds. In some embodiments, the invention includes methods of identifying a compound characteristic associated with partitioning a compound into a condensate, the method comprising: (a) determining condensate preference profiles of a plurality of test compounds by performing a method of determining condensate preference profiles of a plurality of test compounds; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles. In some embodiments, the invention includes methods of designing a compound with a desired condensate preference profile, the method comprising: (a) determining condensate preference profiles of a plurality of test compounds by performing a method of determining condensate preference profiles of a plurality of test compounds; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e) designing a compound that comprises the identified characteristic.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-translational modifications of the polypeptide, for example, glycosylation, sialylation, acetylation, phosphorylation, and the like.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

The section headings used herein are for organizational purposes only and are not to be construed as limiting the subject matter described.

Methods of Assessing Condensate-Associated Characteristics of a Compound

In some aspects of the application, methods of assessing a condensate-associated characteristic of a compound, such as a test compound, and applications thereof are provided. In some embodiments, "condensate" described herein refers to a non-membrane-encapsulated compartment formed by phase separation of one or more of proteins and/or other macromolecules (including all stages of phase separation).

Described in more detail below are techniques for assessing condensate-associated characteristics of a compound and applications to many methods and forms thereof. Those skilled in the art will recognize that, in view of the provided description, several embodiments are possible within the scope and spirit of the disclosure of this application.

In some aspects, provided herein are methods of determining a partition characteristic of a test compound, comprising determining the amount of the test compound in the target condensate. In some embodiments, determining the amount of the test compound in the target condensate thereby determines the partition characteristic of the test compound in the target condensate.

In some aspects, provided herein are methods of determining a relative partition characteristic of a test compound, comprising determining the amount of the test compound in the target condensate, determining the amount of a reference compound in the target condensate, and calculating the ratio of the amount of the test compound and the reference compound in the target condensate.

Additionally, in some aspects, provided herein are methods of determining a condensate preference profile of a test compound, comprising determining the amount of the test compound in a first target condensate, determining the amount of the test compound in a second target condensate, and calculating the ratio of the amount of the test compound in the first and second target condensates. In some embodiments, the methods of determining a condensate preference profile of a test compound comprise determining the partition characteristic or the relative partition characteristic of the test compound in a first target condensate, determining the partition characteristic or the relative partition characteristic of the test compound in a second target condensate, and calculating the ratio of the partition characteristic or the relative partition characteristic of the test compound in the first and second target condensates.

In some embodiments, the methods further comprise repeating the steps of the method for a plurality of test compounds. For example, in some embodiments, the methods comprise repeating the steps of the method for at least about any of 2, 3, 4, 5, 10, 15, 20, 25, 40, 50, 75, 100, 250, 500, 1,000, 10,000, 100,000 or more compounds.

In some embodiments, the methods further comprise combining the test compound and a composition comprising a target condensate and an extra-condensate solution. In some embodiments, the methods further comprise adding the test compound to a composition comprising a target condensate and an extra-condensate solution. In some embodiments, the methods further comprise causing the formation of the target condensate. In some embodiments, the methods further comprise combining the test compound and a precursor composition comprising condensate precursor molecules and then causing the formation of the target condensate. In some embodiments, the methods further comprise adding the test compound to a composition comprising condensate precursor molecules and then causing the formation of the target condensate.

In some embodiments, the methods further comprise combining the test compound and a composition comprising a cell. In some embodiments, the methods further comprise combining the test compound and a composition comprising a cell and then causing the formation of the target condensate. In some embodiments, the methods further comprise causing the formation of the target condensate in a composition comprising a cell and then combining the test compound and the composition. In some embodiments, the methods further comprise causing the compound to enter the cell.

In some embodiments, the methods further comprise adding the test compound to a composition comprising a cell. In some embodiments, the methods further comprise adding the test compound to a composition comprising a cell and then causing the formation of the target condensate. In some embodiments, the methods further comprise causing the formation of the target condensate in a composition comprising a cell and then adding the test compound to the composition. In some embodiments, the methods further comprise causing the compound to enter the cell.

In some embodiments, the methods further comprise separating the target condensate from the extra-condensate solution, e.g., for the purpose of quantifying the target compound in the condensate or the extra-condensate solution. In a cell-free solution, condensates are typically denser than extra-condensate solutions and will sediment. Accordingly, in some embodiments, separating the target condensate from the extra-condensate solution comprises separating the supernatant from the precipitate. In some embodiments, the methods comprise centrifuging the composition. In some embodiments, the methods comprise allowing the condensate to sediment.

Techniques for Determining a Condensate-Associated Characteristic of a Compound

In some aspects, provided herein are methods of determining a condensate-associated characteristic of a compound comprising determining an amount of a test compound that is depleted (including determining that there is a lack of depletion) from an extra-condensate solution due to the presence, formation, and/or modulation of a target condensate. In some embodiments, the method of determining a condensate-associated characteristic of a compound comprises use of a mass spectrometry-based technique (e.g., to determine an amount of a test compound). In some embodiments, the method of determining a condensate-associated characteristic of a compound comprises use of any one or more of liquid chromatography (e.g., HPLC), microscopy, quantitative image analysis, quantitative fluorescent microscopy and spectroscopy, nuclear magnetic resonance spectroscopy, Raman spectroscopy, and/or ultraviolet-visible spectrophotometry (e.g., to determine an amount of a test compound). In some embodiments, such methods are useful in determining a partition characteristic, a relative partition characteristic, and/or a condensate preference profile of a test compound in a composition comprising a target condensate and an extra-condensate solution.

In some embodiments, the method comprises determining an amount of a test compound that is depleted from a system due to the presence and/or formation of a target condensate. In some embodiments, the method comprises determining an amount of a test compound that is in an extra-condensate solution and not associated with a precursor molecule of a target condensate. In some embodiments, the method comprises determining an amount of a test compound that is associated with, such as in, a target condensate. In some embodiments, the method comprises determining an amount of a test compound that is associated with a precursor molecule of a target condensate. In some embodiments, the amount of the test compound depleted from a system due to the presence and/or formation of a target condensate is used to determine a condensate-associated characteristics, e.g., a partition characteristic of the test compound for a target condensate.

In some embodiments, the method comprises comparing a MS signal of a test compound from an extra-condensate solution, or a portion thereof, and a MS signal of the test compound from a reference control, or a portion thereof, such as via a ratio of the MS signal of the test compound from the extra-condensate solution, or the portion thereof, and the MS signal of the test compound from the reference control, or the portion thereof. In some embodiments, the ratio of a MS signal of a test compound from an extra-condensate solution and a MS signal of the test compound from a reference control represents a depletion value. In some embodiments, the depletion value is representative of an amount of a test compound that is depleted from a system due to the presence and/or formation of a target condensate. In some embodiments, the method further comprises obtaining, such as measuring a MS ion signal of a test compound in an extra-condensate solution, or a portion thereof, using a mass spectrometry technique. In some embodiments, the method further comprises obtaining, such as measuring a MS ion signal of a test compound in a reference control, or a portion thereof, using a mass spectrometry technique. In some embodiments, the method further comprises combining a test compound and a composition comprising a target condensate and an extra-condensate solution. In some embodiments, the method further comprises causing the formation of a target condensate in the presence of a test compound to obtain a composition comprising the target condensate and an extra-condensate solution. In some embodiments, the method further comprises separating a target condensate in a composition comprising the target condensate and an extra-condensate solution, such as via pelleting the target condensate in the composition. In some embodiments, the method further comprises obtaining, such as generating, a reference control.

In some embodiments, the amount of the test compound added to a composition comprising the target condensate and an extra-condensate solution, or a precursor thereof, is based on an amount such that a relatively small depletion of the total amount of test compound from the extra-condensate solution can be determined (such as determined by comparing a measurement of the amount of the compound in an extra-condensate and a measurement of the amount of the compound in a reference control). In some embodiments, the amount of the test compound added to a composition comprising the target condensate and an extra-condensate solution is based on the amount of the target condensate, and/or one or more precursor molecules thereof, in the composition. In some embodiments, the amount of the test compound added to a composition comprising the target condensate and an extra-condensate solution is based on the compound capacity of the target condensate. In some embodiments, the amount of the test compound is about 1 µM or less, such as about any of 900 nM or less, 800 nM or less, 700 nM or less, 600 nM or less, 500 nM or less, 450 nM or less, 400 nM or less, 350 nM or less, 300 nM or less, 250 nM or less, 200 nM or less, 150 nM or less, 125 nM or less, 100 nM or less, 90 nM or less, 80 nM or less, 70 nM or less, 60 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, or 1 nM or less. In some embodiments, the lower limit of the test compound is based on the analytical method used to measure the amount of the test compound. In some embodiments, the amount of precursor molecule in the composition is between about 1 µM and about 10 and the test compound is about 1 µM or less, such as about any of 900 nM or less, 800 nM or less, 700 nM or less, 600 nM or less, 500 nM or less, 450 nM or less, 400 nM or less, 350 nM or less, 300 nM or less, 250 nM or less, 200 nM or less, 150 nM or less, 125 nM or less, 100 nM or less, 90 nM or less, 80 nM or less, 70 nM or less, 60 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, or 1 nM or less.

In some embodiments, the method comprises use of a reference control and/or methods of preparing the reference control. The reference controls described herein provide a reference measurement that is useful for determining an amount of a test compound that is depleted from a system due to the presence and/or formation of a target condensate. In some embodiments, wherein a composition comprises: (a) an amount of a target condensate, (b) an extra-condensate solution, (c) an amount, such as concentration, of a precursor macromolecule of the target condensate in the extra-condensate solution, and (d) an amount, such as a concentration, of a test compound in the composition, including (i) an amount of the test compound associated with, including in, the target condensate, and (ii) an amount, such as a concentration, of the test compound in the extra-condensate solution, the reference control comprises the amount, such as concentration, of the precursor macromolecule of the target condensate in the extra-condensate solution, and the amount, such as a concentration, of the test compound in the composition. In some embodiments, the method comprises measuring the amount, such as concentration, of a precursor macromolecule of a target condensate in an extra-condensate solution, or a portion thereof, from a composition comprising the target condensate and the extra-condensate solution.

In some embodiments, the reference control comprises an amount of a precursor macromolecule of the target condensate based on an amount of the precursor macromolecule present in the extra-condensate solution after the composition has been subjected to pelleting of the target condensate. In some embodiments, the reference control has the same concentration of the precursor macromolecule as the concentration of the precursor macromolecule in the extra-condensate solution after the composition has been subjected to pelleting of the target condensate. In some embodiments, the reference control comprises the test compound at a concentration that is the same as that combined with the composition comprising the target condensate and the extra-condensate solution. In some embodiments, the reference control is substantially free of a target condensate. In some embodiments, the method further comprises determining the amount of the test compound in the reference control. In some embodiments, determining the amount of the test compound in the reference control comprises measuring the amount of the test compound in the reference control, or a portion thereof, using a mass spectrometry-based technique.

A variety of mass spectrometry-based techniques are suitable for the methods described herein. In some embodiments, the mass-spectrometry-based technique comprises measuring a MS signal of one or more ion species of one or more compounds, such as one or more test compounds. In some embodiments, the MS signal is of one or more ion species of a test compound, such as one or more charge states of ions of the test compound. In some embodiments, the MS signal is derived from a mass-to-charge (m/z) measurement. In some embodiments, the MS signal is ionization intensity. In some embodiments, the MS signal is peak height. In some embodiments, the MS signal is peak area, such as the integral of a signal corresponding with a MS ion signal. In some embodiments, the MS signal is peak volume, such as the integral of a signal corresponding with a MS ion signal. In some embodiments, the MS signal is a cumulative measurement of measured signals of ions of a test compound. In some embodiments, the mass spectrometry-based technique comprises a liquid chromatography/mass spectrometry (LC/MS) technique, a liquid chromatography/tandem mass spectrometry (LC/MS) technique and/or a direct sample introduction technique (e.g., direct spray). In some embodiments, the mass spectrometry-based technique comprises gas chromatography/mass spectrometry (GC/MS). In some embodiments, the mass spectrometry-based technique comprises an acquisition technique selected from data-dependent acquisition, data-independent acquisition, selected reaction monitoring (SRM), and multiple reaction monitoring (MRM).

Liquid chromatography techniques contemplated by the present application include methods for separating precursor macromolecules and/or test compounds compatible with mass spectrometry techniques. In some embodiments, the liquid chromatography technique comprises a high performance liquid chromatography (HPLC) technique. In some embodiments, the liquid chromatography technique comprises a high-flow liquid chromatography technique. In some embodiments, the liquid chromatography technique comprises a low-flow liquid chromatography technique, such as a micro-flow liquid chromatography technique or a nano-flow liquid chromatography technique. In some embodiments, the liquid chromatography technique comprises an online liquid chromatography technique coupled to a mass spectrometer. In some embodiments, capillary electrophoresis (CE) techniques, or electrospray or MALDI techniques may be used to introduce the sample to a mass spectrometer. In some embodiments, direct sample introduction techniques may be used to introduce the sample to a mass spectrometer. In some embodiment, the mass spectrometry technique comprises an ionization technique. Ionization techniques contemplated by the present application include techniques capable of charging precursor macromolecules and/or test compounds. In some embodiments, the ionization technique is electrospray ionization. In some embodiments, the ionization technique is nano-electrospray ionization. In some embodiments, the ionization technique is atmospheric pressure chemical ionization. In some embodiments, the ionization technique is atmospheric pressure photoionization. In some embodiments, the ionization technique is matrix-assisted laser desorption ionization (MALDI). In some embodiment, the mass spectrometry technique comprises electrospray ionization, nano-electrospray ionization, or a matrix-assisted laser desorption ionization (MALDI) technique.

Mass spectrometers contemplated by the present application, to which an online liquid chromatography technique may be coupled, include high-resolution mass spectrometers and low-resolution mass spectrometers. Thus, in some embodiments, the mass spectrometer is a time-of-flight (TOF) mass spectrometer. In some embodiments, the mass spectrometer is a quadrupole time-of-flight (Q-TOF) mass spectrometer. In some embodiments, the mass spectrometer is a quadrupole ion trap time-of-flight (QIT-TOF) mass spectrometer. In some embodiments, the mass spectrometer is an ion trap. In some embodiments, the mass spectrometer is a single quadrupole. In some embodiments, the mass spectrometer is a triple quadrupole (QQQ). In some embodiments, the mass spectrometer is an orbitrap. In some embodiments, the mass spectrometer is a quadrupole orbitrap. In some embodiments, the mass spectrometer is a Fourier transform ion cyclotron resonance (FT) mass spectrometer. In some embodiments, the mass spectrometer is a quadrupole Fourier transform ion cyclotron resonance (Q-FT) mass spectrometer. In some embodiments, the mass spectrometry technique comprises positive ion mode. In some embodiments, the mass spectrometry technique comprises negative ion mode. In some embodiments, the mass spectrometry technique comprises a time-of-flight (TOF) mass spectrometry technique. In some embodiments, the mass spectrometry technique comprises a quadrupole time-of-flight (Q-TOF) mass spectrometry technique. In some embodiments, the mass spectrometry technique comprises an ion mobility mass spectrometry technique. In some embodiments a low-resolution mass spectrometry technique, such as an ion trap, or single or triple-quadrupole approach is appropriate.

In some embodiments, the mass spectrometry-based technique comprises processing the obtained MS signals of the precursor macromolecules and/or test compounds. In some embodiments, the mass spectrometry-based technique comprises peak detection. In some embodiments, the mass spectrometry-based technique comprises determining an ionization intensity. In some embodiments, the mass spectrometry-based technique comprises determining peak height. In some embodiments, the mass spectrometry-based technique comprises determining peak area. In some embodiments, the mass spectrometry-based technique comprises determining peak volume.

In some embodiments, the mass spectrometry-based technique comprises identifying the test compound.

Thus, for example, in some embodiments, there is provided a method of determining a partition characteristic of a test compound in a target condensate, the method comprising comparing a MS signal of ions of a test compound from an extra-condensate solution and a MS signal of ions of the test compound from a reference control, thereby determining the partition characteristic of the test compound in the target condensate. In some embodiments, the method of determining a partition characteristic of the test compound in the target condensate comprises: (a) obtaining, such as measuring, a MS signal of the test compound in the extra-condensate solution, or a portion thereof, using a mass spectrometry technique; (b) obtaining, such as measuring, a MS ion signal of the test compound in the reference control, or a portion thereof, using a mass spectrometry technique; and (c) comparing the MS signal of ions of the test compound from the extra-condensate solution and the MS signal of ions of the test compound from the reference control, thereby determining the partition characteristic of the test compound in the target condensate.

In some embodiments, provided herein are methods of determining a condensate-associated characteristic of a small molecule test compound (such as a therapeutic small molecule that is 1,000 Da or less and/or satisfies Lipinski's rule of five) comprising determining an amount of the small molecule test compound that is depleted (including determining that there is a lack of depletion) from an extra-condensate solution due to the presence, formation, and/or modulation of a target condensate. In some embodiments, there is provided a method of determining a partition characteristic of a small molecule test compound in a target condensate, the method comprising comparing a MS signal of ions of the small molecule test compound from an extra-condensate solution and a MS signal of ions of the small molecule test compound from a reference control, thereby determining the partition characteristic of the small molecule test compound in the target condensate. In some embodiments, the method of determining a partition characteristic of the small molecule test compound in the target condensate comprises: (a) obtaining, such as measuring, a MS signal of the small molecule test compound in the extra-condensate solution, or a portion thereof, using a mass spectrometry technique; (b) obtaining, such as measuring, a MS ion signal of the small molecule small molecule test compound in the reference control, or a portion thereof, using a mass spectrometry technique; and (c) comparing the MS signal of ions of the small molecule test compound from the extra-condensate solution and the MS signal of ions of the small molecule test compound from the reference control, thereby determining the partition characteristic of the small molecule test compound in the target condensate.

In some embodiments, provided herein are methods of determining a condensate-associated characteristic of a therapeutic compound (such as any of, or any combination of, an exogenous compound, a small molecule, a polypeptide, an oligonucleotide, a nucleic acid, an antibody, or fragment thereof, a synthetically produced compound, including cell culture produced compounds, or a compound that is not a condensate precursor macromolecule) comprising determining an amount of a therapeutic compound that is depleted (including determining that there is a lack of depletion) from an extra-condensate solution due to the presence, formation, and/or modulation of a target condensate. In some embodiments, there is provided a method of determining a partition characteristic of a therapeutic compound in a target condensate, the method comprising comparing a MS signal of ions of the therapeutic compound from an extra-condensate solution and a MS signal of ions of the therapeutic compound from a reference control, thereby determining the partition characteristic of the therapeutic compound in the target condensate. In some embodiments, the method of determining a partition characteristic of the therapeutic compound in the target condensate comprises:

(a) obtaining, such as measuring, a MS signal of the therapeutic compound in the extra-condensate solution, or a portion thereof, using a mass spectrometry technique; (b) obtaining, such as measuring, a MS ion signal of the therapeutic compound in the reference control, or a portion thereof, using a mass spectrometry technique; and (c) comparing the MS signal of ions of the therapeutic compound from the extra-condensate solution and the MS signal of ions of the therapeutic compound from the reference control, thereby determining the partition characteristic of the therapeutic compound in the target condensate.

In some embodiments, the method of determining a partition characteristic of a test compound in a target condensate, the method comprising: (a) combining the test compound and a composition comprising the target condensate and an extra-condensate solution; (b) obtaining, such as preparing, a reference control; (c) measuring a MS signal of the test compound in the extra-condensate solution, or a portion thereof, using a mass spectrometry technique; (d) measuring a MS signal of the test compound in the reference control, or a portion thereof, using a mass spectrometry technique; (e) comparing the MS signal of the test compound from the extra-condensate solution and the MS signal of the test compound from the reference control, thereby determining the partition characteristic of the test compound in the target condensate.

In some embodiments, the method of determining a partition characteristic of a test compound in a target condensate, the method comprising: (a) combining the test compound and a composition comprising the target condensate and an extra-condensate solution; (b) obtaining, such as preparing, a reference control; (c) measuring a MS signal of the test compound in the extra-condensate solution, or a portion thereof, using a mass spectrometry technique; (d) measuring a MS signal of the test compound in the reference control, or a portion thereof, using a mass spectrometry technique; (e) comparing the MS signal of the test compound from the extra-condensate solution and the MS signal of the test compound from the reference control, thereby determining the partition characteristic of the test compound in the target condensate.

In some embodiments, the method of determining a partition characteristic of a test compound in a target condensate, the method comprising: (a) combining the test compound and a composition comprising the target condensate and an extra-condensate solution; (b) incubating the test compound and the composition; (c) pelleting the target condensate in the composition using a centrifugation technique; (d) obtaining, such as preparing, a reference control; (e) measuring a MS signal of the test compound in the extra-condensate solution, or a portion thereof, using a mass spectrometry technique; (f) measuring a MS signal of the test compound in the reference control, or a portion thereof, using a mass spectrometry technique; (g) comparing the MS signal of the test compound from the extra-condensate solution and the MS signal of the test compound from the reference control, thereby determining the partition characteristic of the test compound in the target condensate.

In some embodiments, the method of determining a partition characteristic of a test compound in a target condensate, the method comprising: (a) combining the test compound and a composition comprising the target condensate and an extra-condensate solution; (b) incubating the test compound and the composition; (c) pelleting the target condensate in the composition using a centrifugation technique; (d) obtaining, such as preparing, a reference control; (e) measuring a MS signal of the test compound in the extra-condensate solution, or a portion thereof, using a mass spectrometry technique; (f) measuring a MS signal of the test compound in the reference control, or a portion thereof, using a mass spectrometry technique; (g) comparing the MS signal of the test compound from the extra-condensate solution and the MS signal of the test compound from the reference control, thereby determining the partition characteristic of the test compound in the target condensate.

In some embodiments of any of the methods or method steps described herein, the method is suitable for determining a condensate-associated characteristic for each of plurality of test compounds in a single composition comprising a target condensate. For example, in some embodiments, there is provided a method comprising: (a) combining a plurality of test compounds and a composition comprising the target condensate and an extra-condensate solution; and (b) comparing a MS signal of ions of a first test compound of the plurality of test compounds from an extra-condensate solution and a MS signal of ions of the first test compound from a reference control. In some embodiments, the MS signal of ions of each test compound of the plurality of test compounds from an extra-condensate solution are compared with a respective MS signal of ions of each respective test compound from a reference control. In some embodiments, the reference control comprises a plurality of compounds. In some embodiments, the number of compounds in the plurality of test compounds is limited only by the capacity of the analytical method used for measuring the quantity of each compound. In some embodiments, the plurality of test compounds comprises at least 5, such as at least any of 10, 15, 20, 25, 30, 35, 40, 45, 50, 75, 100, 125, 150, 175, 200, 250, 300, 350, 400, 450, 500, 600, 700, 800, 900, or 1,000, compounds. In some embodiments, the method further comprises obtaining, such as measuring, a MS signal of each of the test compounds in the extra-condensate solution, or a portion thereof, using a mass spectrometry technique. In some embodiments, the method further comprises obtaining, such as measuring, a MS signal of each of the test compounds in the reference control, or a portion thereof, using a mass spectrometry technique. In some embodiments, the MS signal of each of the test compounds in either the extra-condensate solution or the reference control are obtained in a single mass spectrometry analysis.

Test Compounds and Analysis

In some embodiments, the test compound is a small molecule, a polypeptide, a peptidomimetic, a lipid, or a nucleic acid. In some embodiments, the test compound is an approved compound, such as a compound approved for medical treatment by the United States Food and Drug Administration. In some embodiments, the test compound is a novel compound. In some embodiments, the test compound is charged. In some embodiments, the test compound is hydrophobic. In some embodiments, the test compound is hydrophilic. In some embodiments, the test compound is a small molecule. In some embodiments, the small molecule is an alkaloid, a glycoside, a phenazine, a phenol, a polyketide, a terpene, or a tetrapyrrole. In some embodiments, the test compound is an antibody. In some embodiments, the target condensate is an extracellular condensate and the test compound is an antibody. In some embodiments, the test compound is a nucleic acid. In some embodiments, the test compound is RNA, such as a siRNA, miRNA, mRNA, or lnRNA. In some embodiments, the test compound is a siRNA, miRNA, or mRNA. In some embodiments, the test compound is a non-naturally occurring compound. In some embodiments, the test compound is a protein.

In some embodiments, the methods herein comprise adding two or more test compounds. In some embodiments, the two or more compounds are each selected from any of a small molecule, a polypeptide, a lipid, or a nucleic acid. In some embodiments, the two or more test compounds are added sequentially or simultaneously.

In some embodiments, the test compound comprises a label. In some embodiments, the label is a radioactive label, a colorimetric label, a luminescent label, a chemically-reactive label (such as a component moiety used in click chemistry), or a fluorescent label. In some embodiments, the test compound is a small molecule comprising a label. In some embodiments, the test compound is a small molecule comprising a fluorophore. In some embodiments, the test compound is a polypeptide comprising a label. In some embodiments, the test compound is a polypeptide comprising a fluorophore. In some embodiments, the test compound is a nucleic acid comprising a label. In some embodiments, the test compound is a nucleic acid comprising a fluorophore. The test compound label can be conjugated to the test compound covalently or non-covalently.

Methods of determining the amount of test compound are known. In some embodiments, determining the amount of the test compound comprises quantifiably detecting the test compound. In some embodiments, determining the amount of the test compound comprises quantifiably detecting the test compound label. In some embodiments, determining the amount of the test compound comprises detecting activity of the test compound and calculating the amount of test compound needed to cause the amount of activity detected. In some embodiments, the amount of test compound is determined by mass spectrometry, liquid chromatography, and/or ultraviolet-visible spectrophotometry. In some embodiments, the amount of test compound is determined by fluorescence microscopy. Standard curves may be used to aid in determining the amount of test compound. Alternatively or additionally, the amount of test compound may be compared to a reference compound. In some embodiments, the reference compound is the test compound label.

The methods describe herein comprising determining an amount of a compound, such as a test compound or a reference compound, in a condensate are envisioned to encompass direct and indirect techniques for determining the amount of the compound in the condensate. In some embodiments, the amount of a compound in a condensate is determined directly. In some embodiments, the amount of a compound in a condensate is determined indirectly. In some embodiments, the amount of a compound in a condensate is determined via determining the amount of the compound not associated with the condensate, such as the amount of the compound in an extra-condensate solution. In some embodiments, the amount of a compound in a condensate is determined via determining the amount of a reporter compound. In some embodiments, the reporter compound is associated with the condensate. In some embodiments, the reporter compound is not associated with the condensate.

The amount of test compound in the target condensate can be compared to the amount of test compound in other solutions or to the amount added to the composition. Accordingly, in some embodiments, the methods further comprise comparing the amount of test compound in the target condensate to the amount added to the composition; and/or the amount in the extra-condensate solution; and/or the amount of test compound in the cell; and/or the amount of test compound in a second target condensate.

In some embodiments, the methods further comprise comparing the amount of test compound in the target condensate to the amount added to the composition. In some embodiments, comparing comprises calculating a ratio or percentage of the amount of test compound in the target condensate and the amount of test compound added to the composition.

In some embodiments, the methods further comprise comparing the amount of test compound in the target condensate to the amount of test compound in the extra-condensate solution. In some embodiments, comparing comprises calculating a ratio or percentage of the amount of test compound in the target condensate and the amount of test compound in the extra-condensate solution. In some embodiments, the methods further comprise determining the amount of test compound in an extra-condensate solution. In some embodiments, the amount of the test compound in the target condensate is determined prior to, simultaneously with, or after the amount of the test compound in the extra-condensate solution is determined.

In some embodiments, the methods further comprise comparing the amount of test compound in the target condensate to the amount of test compound in the cell. In some embodiments, comparing comprises calculating a ratio or percentage of the amount of test compound in the target condensate and the amount of test compound in the cell. In some embodiments, the methods further comprise determining the amount of test compound in the cell.

In some embodiments, the methods further comprise comparing the amount of test compound in the target condensate to the amount of test compound in a second target condensate. In some embodiments, comparing comprises calculating a ratio or percentage of the amount of test compound in the target condensate and the amount of test compound in the second target condensate. In some embodiments, the methods further comprise determining the amount of test compound in the second target condensate. In some embodiments, the amount of the test compound in the first target condensate is determined prior to, simultaneously with, or after the amount of the test compound in the second target condensate is determined.

In some embodiments, the methods further comprise comparing the amount of test compound in the target condensate to the amount of one or more macromolecules in the target condensate. In some embodiments, comparing comprises calculating a ratio or percentage of the amount of test compound in the target condensate and the amount of one or more macromolecules in the target condensate. In some embodiments, the methods further comprise determining the amount of one or more macromolecules in the target condensate. In some embodiments, the amount of the test compound in the target condensate is determined prior to, simultaneously with, or after the amount of the one or more macromolecules in target condensate is determined.

Methods of forming condensates are known and can vary by condensate. For example, a condensate can be formed by altering the temperature of the composition, such as exposing the composition to lower or higher temperatures; by altering the salt content of the composition, such as diluting a salt in the composition or adding salt to the composition; by increasing the concentration of precursor macromolecules, such as adding a nucleic acid, e.g., RNA, in the composition; adding or changing a buffer in the composition; altering the ionic strength of the composition; altering the pH, such as altering the pH to less than one unit away from the isoelectric point; or adding a crowding agent, such as PEG or dextran. Some exemplary methods of forming condensates are also disclosed in Alberti et al., *J Mol Biol*, 430(23), 2018, 4806-4820, which is herein incorporated by reference.

Compositions

In some embodiments, the composition comprises a cell. In some embodiments, the target condensate is in the cell. In some embodiments, the extra-condensate solution is intracellular fluid, such as cytosol or nucleosol.

In some embodiments, the composition comprises a cell. In some embodiments, the target condensate is not in the cell. In some embodiments, the target condensate is an extracellular condensate, such as a condensate in the extracellular matrix. In some embodiments, the extracellular fluid is interstitial fluid or plasma.

In some embodiments, the cell is a microorganism or an animal cell. In some embodiments, cell is a human cell. In some embodiments, the cell is a neuron. In some embodiments, the cell is a cancer cell. In some embodiments, the cell is or is derived from induced pluripotent stem cells (iPS cells), HeLa cells, or HEK293 cells. In some embodiments, the cell comprises a condensate that is determined to be dysregulated. In some embodiments, the cell comprises a mutation associated with a disease. In some embodiments, the cell has one or more features of a neurodegenerative or proliferative disease. In some embodiments, the cell has been treated with arsenate (and/or another compound known to modulate a condensate), a temperature change, or a pH change. In some embodiments, the cell expresses a protein that is labeled with a fluorescent protein. In some embodiments, the protein is a protein known to concentrate in the target condensate. In some embodiments, the cell expresses a first protein and a second protein, wherein the first protein is labeled with a first label, wherein the first protein is known to concentrate in a first target condensate, wherein the second protein is labeled with a second label, wherein the second protein is known to concentrate in a second target condensate, and wherein the first label and the second label are distinguishable. In some embodiments, the cell expresses a first protein and a second protein, wherein the first protein is labeled with a first fluorescent protein, wherein the first protein is known to concentrate in a first target condensate, wherein the second protein is labeled with a second fluorescent protein, wherein the second protein is known to concentrate in a second target condensate, and wherein the first fluorescent protein and second fluorescent protein are distinguishable.

In some embodiments, the composition does not comprise a cell. In some embodiments, the composition is cell-free. In some embodiments, the composition comprises precursor molecules, which are non-phase separated components that can be incorporated into a condensate and/or have been incorporated into a condensate. Condensates can be formed in cell-free systems from just a few components. For example, the composition may comprise a protein or protein fragments, such as a portion of a protein or a peptide, capable of forming a condensate. In some embodiments, the composition comprises a protein or protein fragment comprising a Low Complexity Domain or an Intrinsically Disordered Sequence. In some embodiments, the composition comprises nucleic acid oligomers or polymers, such as RNA. In some embodiments, the composition comprises a small molecule. In some embodiments, the composition comprises a buffer. In some embodiments, the composition may also comprise one or more salts, and/or one or more macromolecular crowding agents (e.g., poly ethylene glycol or dextran).

In some embodiments, the composition comprises a cell comprising the precursor molecules. In some embodiments, the composition comprises a cell and the method comprises forming the target condensate in the cell. In some embodiments, the method comprises altering the temperature of the cell, such as exposing the composition to lower or higher temperatures; altering the salt content of the cell; adding or changing a buffer surrounding the cell; altering the pH of the cell; or adding a crowding agent, such as PEG or dextran to the cell. In some embodiments, the composition comprises a cell, and the cell comprises a mutation that causes the target condensate to form and/or modifies the target condensate. In some embodiments, the mutation modifies one or more of the following: the size of the target condensate, the shape of the target condensate, the concentration of one or more components of the target condensate, and heterogeneous distribution of components within the target condensate. In some embodiments, the composition comprises a cell, and the cell comprises a mutation that causes the condensate to form.

In some embodiments, the composition comprises a plurality of condensates. In some embodiments, the composition comprises at least any of 2, 3, 4, 5, 6, 7, 8, 9, 10, 15, 20, or 25 condensates. In some embodiments, the composition comprises two or more target condensates. In some embodiments, the composition comprises at least any of 2, 3, 4, 5, 6, 7, 8, 9, 10, 15, 20, or 25 target condensates. In some embodiments, the method comprises repeating the steps of the method for one or more additional target condensates, such as for at least any of 2, 3, 4, 5, 6, 7, 8, 9, 10, 15, 20, or 25 target condensates. In some embodiments, the composition comprises at least any of 2, 3, 4, 5, 6, 7, 8, 9, 10, 15, 20, or 25 condensates of the same condensate type, e.g., condensates that have the same composition and/or partitioning properties. In some embodiments, the composition comprises at least any of 2, 3, 4, 5, 6, 7, 8, 9, 10, 15, 20, or 25 different condensate types, e.g., condensates that do not have the same composition and/or partitioning properties.

Condensates

Many condensates are well known in the art. Examples of known condensates include cleavage bodies, P-granules, histone locus bodies, multivesicular bodies, neuronal RNA granules, nuclear gems, nuclear pores, nuclear speckles, nuclear stress bodies, a nucleolus, Oct1/PTF/transcription (OPT) domains, paraspeckles, perinucleolar compartments, PML nuclear bodies, PML oncogenic domains, polycomb bodies, processing bodies, signaling clusters, viral condensates, Sam68 nuclear bodies, stress granules, or splicing speckles. Many condensates can be identified using microscopy. In some embodiments, the methods further comprise identifying the target condensate.

Condensates used in the methods described herein may be naturally occurring or non-naturally occurring. For example, in some embodiments, the condensate is naturally occurring. In some embodiments, the condensate is non-naturally occurring. In some embodiments, the condensate is artificial. In some embodiments, the condensate is synthetic. In some embodiments, the condensate is semi-synthetic. In some embodiments, the condensate is modified. In some embodiments, the condensate is a modified condensate, wherein a parent condensate of the modified condensate is modified by adding, removing, and/or substituting one or more condensate components.

In some embodiments, wherein the methods described herein assess two more condensates, the first condensate and a second condensate of the two or more condensates may be any combination of condensates. In some embodiments, the first condensate is a modified condensate. In some embodiments, the first condensate is a modified condensate, and the second condensate is a parent condensate of the first condensate. In some embodiments, the first condensate is a target condensate in a first system, such as a first composition, and the second condensate is the target condensate in a second system, such as a second composition. In some embodiments, the first condensate is a normal condensate and the second condensate is a dysregulated condensate.

In some embodiments, provided are methods of determining a condensate preference profile of a test compound, the method comprising: (a) combining the test compound and a first composition comprising a first target condensate; (b) combining the test compound and a second composition comprising a second target condensate; (c) determining the amount of the test compound in the first target condensate; and (d) determining the amount of the test compound in the second target condensate, thereby determining a condensate preference profile of the test compound.

In some embodiments, provided are methods of determining a condensate preference profile of a test compound, the method comprising: (a) adding the test compound to a first composition comprising a first target condensate; (b) adding the test compound to a second composition comprising a second target condensate; (c) determining the amount of the test compound in the first target condensate; and (d) determining the amount of the test compound in the second target condensate, thereby determining a condensate preference profile of the test compound.

The identification of condensates can be aided by the use of a label. For example, a dye or labeled compound can be added to a condensate. In some embodiments, the dye or labeled compound could preferentially enter the target condensate. In some embodiments, the label is a radioactive label, a colorimetric label, a chemically-reactive label, or a fluorescent label. In some embodiments, the composition comprises a first target condensate and a second target condensate, and the first target condensate and the second target condensate are each labeled with different labels, such as the first target condensate is labeled with RFP and the second target condensate is labeled with GFP.

Some condensates may comprise specific macromolecules. Accordingly, in some embodiments, the methods further comprise characterizing a macromolecule in the target condensate. In some embodiments, the macromolecule is a protein or protein fragment. In some embodiments, the protein or protein fragment comprises a Low Complexity Domain or an Intrinsically Disordered Sequence. In some embodiments, the macromolecule is a transcription factor or an RNA binding protein. In some embodiments, the macromolecule is tau, FUS, huntingtin protein, hnRNPA1, TDP43, PGL-3, or fragments or aggregates thereof. In some embodiments, the macromolecule is a nucleic acid, such as RNA or DNA. In some embodiments, the macromolecule is a RNA.

In some embodiments, the target condensate is a cellular condensate. Numerous cellular condensates have been described and numerous more are known to form, but have not yet been described. In some embodiments, the cellular condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a signaling cluster, a viral condensate, a Sam68 nuclear body, a stress granule, or a splicing speckle.

In some embodiments, the target condensate is in a cell when the amount of target compound in the target condensate is determined.

In some embodiments, the target condensate is an extracellular condensate. Extracellular condensates can form in biological solutions outside of a cell, such as the extracellular matrix or plasma, to facilitate reactions or sequester molecules (Muiznieks et al., *J Mol Biol,* 430(23), 2018, 4741-4753).

The dysregulation of various condensates can be associated with a disease. For example, based on cellular and cell-free condensate experiments, disease-associated mutations in the protein fused in sarcoma (FUS) have been shown to cause aberrant phase-separation behavior that contributes directly to development of the motor neuron disease, amyotrophic lateral sclerosis (ALS) (Naumann et al., *Nat Commun,* 9(1), 2018, 335). Accordingly, in some embodiments dysregulation of the target condensate is associated with a disease. In some embodiments, the dysregulation comprises an alteration in one or more of: size of the target condensate; shape of the target condensate; concentration of one or more components of the target condensate; and heterogeneous distribution of components within the condensate, e.g., components located in the core instead of the shell of the condensate. In some embodiments, the alteration is compared to a similar non-dysregulated target condensate.

Methods of Determining a Compound Characteristic Associated with Partitioning of a Test Compound In some embodiments, the invention includes methods of identifying a compound characteristic associated with the partitioning of a compound, or portion thereof, in a condensate, such as associated with the surface and/or core of the condensate.

In some embodiments, the methods comprise determining partition characteristics of a plurality of test compounds in a target condensate by performing a method disclosed herein. In some embodiments, the methods comprise identifying or determining an attribute of a compound, or a portion thereof, contributing, in whole or in part, to partitioning of a compound, or portion thereof, with a condensate.

In some embodiments, identifying a compound characteristic associated with the partitioning of a compound, or portion thereof, that has a desired, such as a similar, partition characteristic in a target condensate comprises identifying a common moiety or motif of the test compounds having a desired, such as similar, partition characteristic. In some embodiments, the compound characteristic of a compound, or a portion thereof, is based on one or more of charge and hydrophobicity.

In some embodiments, the partition characteristic of a compound is based on determining an amount, such as a relative amount, of the compound in a condensate or as compared to one or more condensates, such as a condensate preference profile. For example, in some embodiments, the methods comprise: (a) determining partition characteristics of a plurality of test compounds in the target condensate by performing a method described herein; and (b) identifying test compounds, or a portion thereof, that have a desired partition characteristic, such as a similar partition characteristic, in the condensate. In some embodiments, the methods comprise: (a) determining partition characteristics of a plurality of test compounds in the target condensate by performing a method described herein; (b) comparing the partition characteristics of a subset or all of the plurality of test compounds in the target condensate; (c) identifying test compounds that have the same or similar partition characteristics in the target condensate; and (d) identifying a characteristic that a subset or all of the identified test compounds have in common in addition to the same or similar partition characteristics.

In some embodiments, the methods comprise: (a) determining relative partition characteristics of a plurality of test compounds in the target condensate by performing a method described herein; and (b) identifying test compounds, or a portion thereof, that have a desired relative partition characteristic, such as a similar relative partition characteristic, in the condensate. In some embodiments, the methods comprise: (a) determining relative partition characteristics of a plurality of test compounds in the target condensate by performing a method described herein; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics.

In some embodiments, the methods comprise: (a) determining condensate preference profiles of a plurality of test compounds in the target condensate by performing a method described herein; and (b) identifying test compounds, or a portion thereof, that have a desired condensate preference profile, such as a similar condensate preference profile, in the condensate. In some embodiments, the methods comprise (a) determining condensate preference profiles of a plurality of test compounds by performing a method described herein; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles.

In some embodiments of the methods described herein, identifying test compounds that have the same or similar partition characteristics, relative partition characteristics, or condensate preference profiles in the target condensate comprises identifying two or more test compounds that associate with any portion of a target condensate. In some embodiments of the methods described herein, identifying test compounds that have the same or similar partition characteristics, relative partition characteristics, or condensate preference profiles in the target condensate comprises identifying two or more test compounds that do not associate with any portion of a target condensate.

In some embodiments, the methods disclosed herein further comprise making the compound identified and/or designed using the methods described herein.

Methods of Designing a Compound with a Desired Partition Characteristic

In some embodiments, the invention includes methods of designing a compound with a desired partition characteristic with regards to a target condensate. In some embodiments, the invention includes methods of designing a compound with a desired partition characteristic to a target condensate.

In some embodiments, the methods comprise identifying or determining a compound, or a portion thereof, comprising a desired partition characteristic with regards to a target condensate. In some embodiments, the methods comprise identifying or determining an attribute of a compound, or a portion thereof, contributing, in whole or in part, to a desired partition characteristic with regards to a target condensate. In some embodiments, the methods comprise identifying or determining a compound, or a portion thereof, comprising a desired partition characteristic to a target condensate. In some embodiments, the methods comprise identifying or determining an attribute of a compound, or a portion thereof, contributing, in whole or in part, to a desired partition characteristic to a target condensate. In some embodiments, the methods comprise modifying an identified compound, or a portion thereof, to optimize a desired partition characteristic.

In some embodiments, the method of designing a compound with a desired partition characteristic comprises (a) determining a partition characteristics for each of a plurality of test compounds in a target condensate by performing a method described herein; and (b) identifying one or more of the plurality of test compounds, or portions thereof, having a desired, such as similar, partition characteristic in a the target condensate. In some embodiments, the methods comprise comparing partition characteristics of a subset or all of a plurality of test compounds in a target condensate. In some embodiments, the methods comprise selecting and/or designing a compound, or portion thereof, of a plurality of test compounds having a desired partition characteristic.

In some embodiments, the method of identifying a compound characteristic associated with a desired partitioning characteristic with regards to a target condensate comprises: (a) determining partition characteristics of a plurality of test compounds in the target condensate by performing a method described herein; (b) comparing the partition characteristics of a subset or all of the plurality of test compounds; (c) identifying test compounds that have the same or similar partition characteristics in the target condensate; and (d) identifying a characteristic that a subset or all of the identified test compounds have in common in addition to the same or similar partition characteristics.

In some embodiments, the method of identifying a compound characteristic associated with partitioning a compound into a condensate comprises: (a) determining partition characteristics of a plurality of test compounds in the target condensate by performing a method described herein; (b) comparing the partition characteristics of a subset or all of the plurality of test compounds; (c) identifying test compounds that have the same or similar partition characteristics in the target condensate; and (d) identifying a characteristic that a subset or all of the identified test compounds have in common in addition to the same or similar partition characteristics.

In some embodiments, identifying test compounds, or portions thereof, that have the same or a desired, such as a similar, partition characteristic in a target condensate comprises identifying a common moiety or motif of the test compounds having a desired, such as similar, partition characteristic. In some embodiments, the compound characteristic of a compound, or a portion thereof, is based on one or more of charge and hydrophobicity.

In some embodiments, identified test compounds, or portion(s) thereof, can be used as the basis for the identification and/or design of one or more compounds having a desired partition characteristic. In some embodiments, the one or more compounds represents a privileged library. In some embodiments, the privileged library comprises a set of one or more compounds, the set being a part or the whole of the privileged library, comprising a moiety that comprises the identified compound, or portion(s) thereof. In some embodiments, each of the compounds of the privileged library have a similar partition characteristic, such as partition characteristics within at least about 20% of one another. In some embodiments, each of the compounds of the privileged library meet or exceed a threshold partition characteristic. In some embodiments, the privileged library comprises at least about 10 compounds, such as at least about any of 25 compounds, 50 compounds, 150 compounds, 200 compounds, 250 compounds, 300 compounds, 350 compounds, 400 compounds, 450 compounds, 500 compounds, 1,000 compounds, 1,500 compounds, 2,000 compounds, 2,500 compounds, 3,000 compounds, 3,500 compounds, 4,000 compounds, 4,500 compounds, 5,000 compounds, 10,000 compounds, 20,000 compounds, 30,000 compounds, 40,000 compounds, or 50,000 compounds. In some embodiments, each of the compounds of a set of a privileged library are suitable for administration to an individual. In some embodiments, each of the compounds of a privileged library has a molecular weight of less than 1,000 Da, such as 500 Da or less. In some embodiments, each of the compounds of a privileged library satisfy Lipinski's rule of five. In some embodiments, the privileged library comprises compounds present in a single composition. In some embodiments, the privileged library can be used to identify one or more compounds useful for targeting a target condensate, wherein the one or more compounds are identified from the privileged library using one or more traditional drug screening methods.

In some embodiments, designing the compound comprises adding (such as attaching, e.g., covalently attaching) a moiety that comprises the identified characteristic to the compound, thereby conferring the desired partition characteristic to the compound. In some embodiments, designing the compound comprises removing a moiety that comprises the identified characteristic, thereby conferring the desired partition characteristic to the compound. In some embodiments, the compound is designed, in whole or in part, using an approach comprising a modeling, computer, and/or calculation-based technique, e.g., a bioinformatic, cheminformatic, and/or artificial intelligence (AI)-based technique.

In some embodiments, the methods comprise designing a test compound, or a portion thereof, based on an attaching a moiety that comprises a characteristic, such as a chemical structure or motif, identified via a condensate-associated characteristic, thereby conferring a desired partition characteristic to the test compound. In some embodiments, the identified characteristic, in whole or in part, modulates a condensate-associated characteristic, such as a partition characteristic, of the test compound, such as increasing or decreasing the degree to which the test compound partitions in a test condensate. In some embodiments, the methods of designing a test compound comprise attaching a moiety that comprises a characteristic identified via a condensate-associated characteristic to a precursor of the test compound at any number of position and/or stereochemical orientations. In some embodiments, the methods of designing a test compound comprise removing a moiety that comprises a characteristic identified via a condensate-associated characteristic. In some embodiments, the methods of designing a test compound comprise changing a moiety to another moiety that comprises a characteristic identified via a condensate-associated characteristic to a precursor of the test compound at any number of position and/or stereochemical orientations. In some embodiments, the methods of designing a test compound comprise attaching, removing, and/or changing more than one moiety that comprises a characteristic identified via a condensate-associated characteristic to a precursor of the test compound. In some embodiments, the test compound comprises a feature to facilitate modulation (such as attaching, removing, changing) of a moiety, such as a compound label (e.g., a component moiety used in click chemistry).

In some embodiments, identified test compounds, or portion(s) thereof, can be used as the basis for the identification and/or design of one or more compounds having a desired biological activity. In some embodiments, the one or more compounds represents a privileged library. In some embodiments, the methods described herein comprise designing a test compound, or a portion thereof, based on an attaching, removing, or changing a moiety that comprises a characteristic, such as a chemical structure or motif, identified via a condensate-associated characteristic, thereby conferring a desired biological activity to the test compound. In some embodiments, the desired biological activity of a precursor compound is improved by modulating a condensate-associated characteristic of the precursor compound. In some embodiments, the undesired biological activity of a precursor compound is decreased by modulating a condensate-associated characteristic of the precursor compound.

In some embodiments, condensate-associated characteristic data, such as partition characteristic data, and/or identified test compounds, or portions thereof, can be used to develop one or more rule sets. In some embodiments, the one or more rule sets can be used as a basis for the identification and/or design of one or more compounds using an approach comprising modeling, computer and/or calculation-based techniques, e.g., bioinformatic, cheminformatic, and/or artificial intelligence (AI)-based identification of a compound having a desired partition characteristic. Also provided are computer software for determining and/or applying the one or more rule sets.

In some embodiments, the partition characteristic of a compound is based on determining an amount, such as a relative amount, of the compound in a condensate or as compared to one or more condensates, such as a condensate preference profile. For example, in some embodiments, the method of designing a compound with a desired relative partition characteristic comprises determining relative partition characteristics of a plurality of test compounds in the target condensate by performing a method described herein. In some embodiments, the method of designing a compound with a desired relative partition characteristic comprises: (a) determining relative partition characteristics of a plurality of test compounds in the target condensate by performing a method described herein; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e) designing a compound that comprises the identified characteristic. In some embodiments, the method of designing a compound with a desired relative partition characteristic comprises: (a) determining relative partition characteristics of a plurality of test compounds in the target condensate by performing a method described herein; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e) designing a compound that does not comprise the identified characteristic.

In some embodiments, the method of designing a compound with a desired condensate preference profile comprises determining condensate preference profiles of a plurality of test compounds by performing a method disclosed herein. In some embodiments, the method of designing a compound with a desired condensate preference profile comprises (a) determining condensate preference profiles of a plurality of test compounds by performing a method disclosed herein; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e) designing a compound that comprises the identified characteristic. In some embodiments, the method of designing a compound with a desired condensate preference profile comprises (a) determining condensate preference profiles of a plurality of test compounds by performing a method disclosed herein; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e) designing a compound that does not comprise the identified characteristic.

In some embodiments, the methods disclosed herein further comprise making the compound identified and/or designed using the methods described herein.

Methods of Screening a Test Compound

In some embodiments, the invention includes methods of screening a test compound for a desired partition characteristic from a group of candidate compounds, the method comprising: (a) determining a partition characteristic of each of the group of candidate compounds; and (b) identifying the test compound having the desired partition characteristic.

In some embodiments, the desired partition characteristic is based on a partition characteristic associated with a target condensate. In some embodiments, the desired partition characteristic is based on a partition characteristic associated with a plurality of target condensates. In some embodiments, the methods comprise identifying or determining a target condensate. In some embodiments, the target condensate is associated with a disease. In some embodiments, the target condensate associated with a disease is known in the art. In some embodiments, the methods comprise obtaining a target condensate, such as a target condensate associated with a disease.

In some embodiments, the partition characteristic of a group of candidate compound, such as more than one candidate compounds, in the target condensate is determined according to the methods described herein. In some embodiments, the group of candidate compounds is at least about any of 2, 5, 10, 15, 50, 75, 100, 150, 200, 300, 400, or 500 candidate compounds. In some embodiments, the partition characteristic of a candidate compound in the target condensate is determined in vitro. In some embodiments, the partition characteristic of a candidate compound in the target condensate is determined in a cellular system. In some embodiments, the partition characteristic of a candidate compound in the target condensate is determined in a non-cellular system, such as a composition comprising a target condensate or components thereof.

In some embodiments, identifying a test compound, or portion thereof, having a desired partition characteristic comprises identifying a test compound, or portion thereof, that associates with any portion of the target condensate, such as associates with the exterior, surface, and/or core of the target condensate. In some embodiments, the desired partition characteristic is a suitable partition characteristic for being useful for treating a disease in an individual.

In some embodiments, the invention includes methods of identifying a test compound useful for treating a disease in an individual in need thereof. In some embodiments, the methods comprise: (a) identifying a target condensate associated with a disease; and (b) determining a partition characteristic of a candidate compound in the target condensate, and (c) identifying a test compound, or portion thereof, having a suitable partition characteristic for being useful for treating the disease.

In some embodiments, the methods comprise identifying or determining a target condensate associated with a disease. In some embodiments, the target condensate associated with a disease is known in the art. In some embodiments, the methods comprise obtaining a target condensate associated with a disease. In some embodiments, the methods comprise identifying or determining one or more target condensates associated with a disease.

In some embodiments, the method of screening a test compound comprises: (a) determining a partition characteristic of the test compound in the presence of a second compound; and (b) determining a partition characteristic of the test compound in the absence of the second compound. In some embodiments, the method further comprises comparing the partition characteristic of the test compound in the presence of the second compound and the partition characteristic of the test compound in the absence of the second compound. In some embodiments, the method further comprises determining the alteration of the partition characteristic of a test compound in the presence or absence of a second compound.

In some embodiments, the method of screening a test compound comprises: (a) determining a partition characteristic of a second compound in the presence of the test compound; and (b) determining a partition characteristic of the second compound in the absence of the test compound. In some embodiments, the method further comprises comparing the partition characteristic of the second compound in the presence of the test compound and the partition characteristic of the second compound in the absence of the test compound. In some embodiments, the method further comprises determining the ability of a test compound to alter the partition characteristic of the second compound.

In some embodiments, the partition characteristic of a candidate compound, such as one or more candidate compounds, in the target condensate is determined according to the methods described herein. In some embodiments, the methods comprise determining a partition characteristic of a plurality of candidate compounds for a target condensate. In some embodiments, the plurality of candidate compounds is at least about any of 2, 5, 10, 15, 50, 75, 100, 150, 200, 300, 400, or 500 candidate compounds. In some embodiments, the partition characteristic of a candidate compound in the target condensate is determined in vitro. In some embodiments, the partition characteristic of a candidate compound in the target condensate is determined in a cellular system. In some embodiments, the partition characteristic of a candidate compound in the target condensate is determined in a non-cellular system, such as a composition comprising a target condensate or components thereof.

In some embodiments, identifying a test compound, or portion thereof, having a suitable partition characteristic for being useful for treating the disease comprises identifying a test compound, or portion thereof, that associates with any portion of the target condensate, such as associates with the exterior, surface, and/or core of the target condensate.

In some embodiments, the methods disclosed herein comprising identifying, determining, designing, and/or screening for a compound, such as a compound from a group of candidate compounds, further comprises assessing the compound based on an additional parameter of the compound. In some embodiments, identifying a compound is based on assessing, such as characterizing or determining, condensate-associated characteristics of the compound and one or more additional parameters, such as molecular weight and pharmaceutical utility.

In some embodiments, the methods disclosed herein further comprise making the compound identified, designed, and/or screened for using the methods described herein.

Exemplary Embodiments

Among the provided embodiments are:

Embodiment 1. A method of determining a partition characteristic of a test compound in a target condensate, the method comprising: (a) adding the test compound to a composition comprising a target condensate and an extra-condensate solution; and (b) determining the amount of the test compound in the target condensate, thereby determining the partition characteristic of the test compound in the target condensate.

Embodiment 2. The method of embodiment 1, further comprising causing the formation of the target condensate prior to step (a).

Embodiment 3. A method of determining a partition characteristic of a test compound in a target condensate, the method comprising: (a) adding the test compound to a composition comprising precursor molecules; (b) causing the formation of the target condensate to obtain a composition comprising the target condensate and an extra-condensate solution; and (c) determining the amount of the test compound in the target condensate, thereby determining the partition characteristic of the test compound in the target condensate.

Embodiment 4. The method of any one of embodiments 1-3, further comprising determining the amount of the test compound in the extra-condensate solution.

Embodiment 5. The method of embodiment 4, wherein the amount of the test compound in the target condensate is determined prior to, simultaneously with, or after the amount of the test compound in the extra-condensate solution is determined.

Embodiment 6. The method of embodiment 4 or 5, further comprising determining the ratio of the amount of test compound in the target condensate and the amount of test compound in the extra-condensate solution.

Embodiment 7. The method of any one of embodiments 1-6, further comprising separating the target condensate from the extra-condensate solution.

Embodiment 8. The method of any one of embodiments 1-7, further comprising identifying the target condensate prior to determining the amount of test compound in the target condensate.

Embodiment 9. The method of any one of embodiments 1-8, wherein dysregulation of the target condensate is associated with a disease.

Embodiment 10. The method of any one of embodiments 1-9, further comprising characterizing the target condensate by identifying one or more macromolecules comprised therein.

Embodiment 11. The method of any one of embodiments 1-10, wherein the target condensate comprises a protein comprising an intrinsically disordered sequence.

Embodiment 12. The method of any one of embodiments 1-11, further comprising labeling the target condensate in order to visualize the target condensate.

Embodiment 13. The method of embodiment 12, wherein the target condensate is labeled with a radioactive label, a colorimetric label, or a fluorescent label.

Embodiment 14. The method of any one of embodiments 1-13, wherein the composition comprises a cell.

Embodiment 15. The method of embodiment 14, wherein the cell is a microorganism or an animal cell.

Embodiment 16. The method of embodiment 14 or 15, wherein the cell comprises a condensate that is determined to be dysregulated.

Embodiment 17. The method of any one of embodiment 14-16, wherein the cell has one or more features of a neurodegenerative or proliferative disease.

Embodiment 18. The method of any one of embodiments 1-17, wherein the target condensate is a cellular condensate.

Embodiment 19. The method of embodiment 18, wherein the cellular condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

Embodiment 20. The method of any one of embodiments 1-19, wherein the target condensate is in a cell.

Embodiment 21. The method of any one of embodiment 1-20, wherein the extra-condensate solution is intracellular fluid.

Embodiment 22. The method of embodiment 21, wherein the intracellular fluid is cytosol or nucleosol.

Embodiment 23. The method of any one of embodiments 1-17, wherein the target condensate is an extracellular condensate.

Embodiment 24. The method of any embodiment 23, wherein the extra-condensate solution is extracellular fluid.

Embodiment 25. The method of embodiment 24, wherein the extracellular fluid is interstitial fluid.

Embodiment 26. The method of any one of embodiments 1-13, wherein the composition does not comprise a cell.

Embodiment 27. The method of any one of embodiments 1-26, wherein the composition comprises one or more of: a macromolecule, a salt, and a buffer.

Embodiment 28. The method of any one of embodiments 1-27, wherein the composition comprises two or more target condensates.

Embodiment 29. The method of any one of embodiments 1-28, wherein the method comprises repeating the steps of the method for one or more additional condensates.

Embodiment 30. The method of any one of embodiments 1-29, wherein the test compound is small molecule, a polypeptide, or a nucleic acid.

Embodiment 31. The method of any one of embodiments 1-30, wherein the test compound comprises a test compound label.

Embodiment 32. The method of embodiment 31, wherein the test compound label is a radioactive label, a colorimetric label, or a fluorescent label.

Embodiment 33. The method of embodiment 31 or 32, wherein the test compound label is a fluorescent label.

Embodiment 34. The method of any one of embodiments 31-33, wherein the amount of the test compound is determined by detecting the test compound label.

Embodiment 35. The method of any one of embodiments 1-34, wherein the amount of the test compound is determined by mass spectrometry, liquid chromatography, and/or ultraviolet-visible spectrophotometry.

Embodiment 36. A method of determining the partition characteristics of a plurality of test compounds in a target condensate, the method comprising performing the method of any one of embodiments 1-35 with a plurality of test compounds.

Embodiment 37. The method of embodiment 36, further comprising comparing the partition characteristics of a subset or all of the plurality of test compounds in the target condensate.

Embodiment 38. The method of embodiment 37, further comprising identifying test compounds that have the same or similar partition characteristics in a target condensate.

Embodiment 39. The method of embodiment 38, further comprising identifying a characteristic that a subset or all of the identified test compounds have in common in addition to the same or similar partition characteristics.

Embodiment 40. The method of embodiment 39, further comprising determining the partition characteristics in a target condensate for one or more additional test compounds that comprise the identified characteristic.

Embodiment 41. A method of determining a relative partition characteristic of a test compound in a target condensate, the method comprising: (i) determining the partition characteristic of the test compound by performing the method of any one of embodiments 1-35 with the test compound; (ii) determining the partition characteristic of a reference compound by performing the method of any one of embodiments 1-35 with the reference compound; and (iii) calculating the ratio of the partition characteristics determined in (i) and (ii), thereby determining the relative partition characteristic of the test compound in the target condensate.

Embodiment 42. The method of embodiment 41, wherein the test compound comprises a test compound label.

Embodiment 43. The method of embodiment 42, wherein the reference compound is the test compound label.

Embodiment 44. A method of determining relative partition characteristics of a plurality of test compounds in a target condensate, the method comprising: (1) performing the method of any one of embodiments 41-43; and (2) repeating steps (i) and (iii) with a plurality of test compounds.

Embodiment 45. The method of embodiment 44, further comprising comparing the relative partition characteristics in the target condensate of a subset or all of the plurality of test compounds.

Embodiment 46. The method of embodiment 45, further comprising identifying test compounds that have the same or similar relative partition characteristics in the target condensate.

Embodiment 47. The method of embodiment 46, further comprising identifying a characteristic that a subset or all of the identified test compounds have in common in addition to the same or similar relative partition characteristics.

Embodiment 48. The method of embodiment 47, further comprising determining the relative partition characteristics in the target condensate for one or more additional test compounds that comprise the identified characteristic.

Embodiment 49. A method of determining a condensate preference profile of a test compound, the method comprising: (a) adding the test compound to a composition comprising a first target condensate and a second target condensate; (b) determining the amount of the test compound in the first target condensate; (c) determining the amount of the test compound in the second target condensate; and (d) calculating a ratio of the amount of the test compound determined in the first target condensate and the second target condensate, thereby determining the condensate preference profile of the test compound.

Embodiment 50. The method of embodiment 49, further comprising causing the formation of the first target condensate and/or the second target condensate prior to step (a).

Embodiment 51. A method of determining a condensate preference profile of a test compound, the method comprising: (a) adding the test compound to a composition comprising precursor molecules; (b) causing the formation of a first target condensate and a second target condensate in the composition; (c) determining the amount of the test compound in the first target condensate; (d) determining the amount of the test compound in the second target condensate; and (e) calculating a ratio of the amount the test compounds determined in the first target condensate and the second target condensate, thereby determining the condensate preference profile of the test compound.

Embodiment 52. The method of any one of embodiments 49-51, wherein the amount of the test compound in the first target condensate is determined prior to, simultaneously with, or after the amount of the test compound in the second target condensate is determined.

Embodiment 53. The method of any one of embodiments 49-52, further comprising separating the first target condensate and the second target condensate from the composition.

Embodiment 54. The method of any one of embodiments 49-53, further comprising identifying the first target condensate and/or the second target condensate prior to determining the amount of test compound in the first condensate and/or the second condensate.

Embodiment 55. The method of any one of embodiments 49-54, wherein dysregulation of the first target condensate and/or the second target condensate is associated with a disease.

Embodiment 56. The method of any one of embodiments 49-55, further comprising characterizing the first target condensate and/or the second target condensate by identifying one or more macromolecules comprised therein.

Embodiment 57. The method of any one of embodiments 49-56, further comprising labeling the first target condensate and/or the second target condensate in order to visualize the first condensate target condensate and/or the second target condensate.

Embodiment 58. The method of embodiment 57, wherein the first target condensate and the second target condensate are labeled with different labels.

Embodiment 59. The method of embodiment 57 or 58, wherein the first target condensate and/or the second target condensate are labeled with a radioactive label, a colorimetric label, or a fluorescent label.

Embodiment 60. The method of any one of embodiments 49-56, wherein the composition comprises a cell.

Embodiment 61. The method of embodiment 60, wherein the cell is a microorganism or an animal cell.

Embodiment 62. The method of embodiment 60 or 61, wherein the cell comprises a condensate that is determined to be dysregulated.

Embodiment 63. The method of any one of embodiments 60-62, wherein the cell has one or more features of a neurodegenerative or proliferative disease.

Embodiment 64. The method of any one of embodiments 49-56, wherein the first target condensate and/or the second target condensate are cellular condensates.

Embodiment 65. The method of embodiment 64, wherein the first target condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

Embodiment 66. The method of embodiment 64 or 65, wherein the second target condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

Embodiment 67. The method of any one of embodiments 49-66, wherein the first target condensate and/or the second target condensate are in a cell.

Embodiment 68. The method of any one of embodiments 49-63, wherein the first target condensate and/or the second target condensate are extracellular condensates.

Embodiment 69. The method of any one of embodiments 49-59, wherein the composition does not comprise a cell.

Embodiment 70. The method of any one of embodiments 49-69, wherein the composition comprises one or more of: a macromolecule, a salt, and a buffer.

Embodiment 71. The method of any one of embodiments 49-70, wherein the composition comprises one or more additional target condensates.

Embodiment 72. The method of any one of embodiments 49-71, wherein the method comprises repeating the steps of the method for one or more additional target condensates.

Embodiment 73. A method of determining condensate preference profiles of a plurality of test compounds, the method comprising performing the method of any one of embodiments 49-72 with a plurality of test compounds.

Embodiment 74. The method of embodiment 73, further comprising comparing condensate preference profiles of a subset or all of the plurality of test compounds.

Embodiment 75. The method of embodiment 74, further comprising identifying test compounds that have the same or similar condensate preference profiles.

Embodiment 76. The method of embodiment 75, further comprising identifying a characteristic that a subset or all of the identified test compounds have in common in addition to the same or similar condensate preference profiles.

Embodiment 77. The method of embodiment 76, further comprising determining the relative partition characteristic for one or more additional test compounds that comprise the identified characteristic.

Embodiment 78. A method of identifying a compound characteristic associated with partitioning a compound into a condensate, the method comprising: (a) determining partition characteristics of a plurality of test compounds in the target condensate by performing the method of embodiment 36; (b) comparing the partition characteristics of a subset or all of the plurality of test compounds in the target compound; (c) identifying test compounds that have the same or similar partition characteristics in the target condensate; and (d) identifying a characteristic that a subset or all of the identified test compounds have in common in addition to the same or similar partition characteristics.

Embodiment 79. A method of identifying a compound characteristic associated with partitioning a compound into a condensate, the method comprising: (a) determining relative partition characteristics of a plurality of test compounds in the target condensate by performing the method of embodiment 44; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics.

Embodiment 80. A method of identifying a compound characteristic associated with partitioning a compound into a condensate, the method comprising: (a) determining condensate preference profiles of a plurality of test compounds by performing the method of embodiment 73; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles.

Embodiment 81. A method of designing a compound with a desired partition characteristic to a target condensate, the method comprising: (a) determining partition characteristics of a plurality of test compounds in the target condensate by performing the method of embodiment 36; (b) comparing the partition characteristics of a subset or all of the plurality of test compounds in the target condensate; (c) identifying test compounds that have the same or similar partition characteristics in the target condensate; (d) identifying a characteristic that a subset or all of the identified test compounds have in common in addition to the same or similar partition characteristics; and (e) designing a compound that comprises the identified characteristic.

Embodiment 82. A method of designing a compound with a desired relative partition characteristic, the method comprising: (a) determining relative partition characteristics of a plurality of test compounds in the target condensate by performing the method of embodiment 44; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e) designing a compound that comprises the identified characteristic.

Embodiment 83. A method of designing a compound with a desired condensate preference profile, the method comprising: (a) determining condensate preference profiles of a plurality of test compounds by performing the method of embodiment 73; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e) designing a compound that comprises the identified characteristic.

Embodiment 84. The method of any one of embodiments 81-83, further comprising making the compound.

Embodiment 85. A method of screening a test compound for a desired partition characteristic from a group of candidate compounds, the method comprising: (a) determining a partition characteristic of each of the group of candidate compounds; and (b) identifying the test compound having the desired partition characteristic.

Embodiment 86. The method of embodiment 85, wherein the partition characteristic of each of the group of candidate compounds is determined in vitro.

Embodiment 87. The method of embodiment 85 or 85, wherein the test compound has a suitable partition characteristic for being useful for treating a disease in an individual.

Embodiment 88. A method of identifying a test compound useful for treating a disease in an individual in need thereof, the method comprising: (a) identifying a target condensate associated with the disease; (b) determining a partition characteristic of a candidate compound in the target condensate, and (c) identifying the test compound having a suitable partition characteristic for being useful for treating the disease.

Further Exemplary Embodiments

Also among the provided embodiments are:

E1. A method of determining a partition characteristic of a test compound in a target condensate, the method comprising: (a) combining the test compound and a composition comprising the target condensate and an extra-condensate solution; (b) determining the amount of the test compound in the target condensate, thereby determining the partition characteristic of the test compound in the target condensate.

E2. The method of embodiment E1, further comprising causing the formation of the target condensate prior to step (a).

E3. A method of determining a partition characteristic of a test compound in a target condensate, the method comprising: (a) causing the formation of the target condensate in the presence of the test compound to obtain a composition comprising the target condensate and an extra-condensate solution; and (b) determining the amount of the test compound in the target condensate, thereby determining the partition characteristic of the test compound in the target condensate.

E4. The method of embodiment E3, further comprising combining the test compound and a precursor composition comprising precursor molecules prior to step (a).

E5. The method of embodiment E3, further comprising adding the test compound to a precursor composition comprising precursor molecules prior to step (a).

E6. The method of any one of embodiments E1-E5, further comprising determining the amount of the test compound in the extra-condensate solution.

E7. The method of embodiment E6, wherein the amount of the test compound in the target condensate is determined prior to, simultaneously with, or after the amount of the test compound in the extra-condensate solution is determined.

E8. The method of embodiment E6 or E7, further comprising determining the ratio of the amount of test compound in the target condensate and the amount of test compound in the extra-condensate solution.

E9. The method of any one of embodiments E1-E8, further comprising separating the target condensate from the extra-condensate solution.

E10. The method of any one of embodiments E1-E9, further comprising identifying the target condensate prior to determining the amount of test compound in the target condensate.

E11. The method of any one of embodiments E1-E10, wherein dysregulation of the target condensate is associated with a disease.

E12. The method of any one of embodiments E1-E11, further comprising characterizing the target condensate by identifying one or more macromolecules comprised therein.

E13. The method of embodiment E12, wherein the identifying comprises determining the amount of the one or more macromolecules in the target condensate.

E14. The method of embodiment E13, further comprising determining the ratio of the amount of test compound in the target condensate and the amount of the one or more macromolecules in the target condensate.

E15. The method of any one of embodiments E1-E14, wherein the target condensate comprises a protein comprising an intrinsically disordered sequence.

E16. The method of any one of embodiments E1-E15, further comprising labeling the target condensate in order to visualize the target condensate.

E17. The method of embodiment E16, wherein the target condensate is labeled with a radioactive label, a colorimetric label, or a fluorescent label.

E18. The method of any one of embodiments E1-E17, wherein the composition comprises a cell.

E19. The method of embodiment E18, wherein the cell is a microorganism or an animal cell.

E20. The method of embodiment E18 or E19, wherein the cell comprises a condensate that is determined to be dysregulated.

E21. The method of any one of embodiment E18-E20, wherein the cell has one or more features of a neurodegenerative or proliferative disease.

E22. The method of any one of embodiments E1-E21, wherein the target condensate is a cellular condensate.

E23. The method of embodiment E22, wherein the cellular condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

E24. The method of any one of embodiments E1-E23, wherein the target condensate is in a cell.

E25. The method of embodiment E24, wherein the cell is a microorganism or an animal cell.

E26. The method of embodiment E24 or E25, wherein the cell has one or more features of a neurodegenerative or proliferative disease.

E27. The method of any one of embodiment E1-E26, wherein the extra-condensate solution is intracellular fluid.

E28. The method of embodiment E27, wherein the intracellular fluid is cytosol or nucleosol.

E29. The method of any one of embodiments E1-E21, wherein the target condensate is not in a cell.

E30. The method of embodiment E29, wherein the target condensate is an extracellular condensate.

E31. The method of any one of embodiments E1-E22 or E29-E30, wherein the extra-condensate solution is extracellular fluid.

E32. The method of embodiment E31, wherein the extracellular fluid is interstitial fluid.

E33. The method of any one of embodiments E1-E17, wherein the method is a cell free assay method.

E34. The method of any one of embodiments E1-E33, wherein the composition comprises one or more of: a macromolecule, a salt, and a buffer.

E35. The method of any one of embodiments E1-E34, wherein the composition comprises two or more target condensates.

E36. The method of any one of embodiments E1-E35, wherein the method comprises repeating the steps of the method for one or more additional condensates.

E37. The method of any one of embodiments E1-E36, wherein the test compound is small molecule, a polypeptide, or a nucleic acid.

E38. The method of any one of embodiments E1-E37, wherein the test compound comprises a test compound label.

E39. The method of embodiment E38, wherein the test compound label is a radioactive label, a colorimetric label, or a fluorescent label.

E40. The method of embodiment E38 or E39, wherein the test compound label is a fluorescent label.

E41. The method of any one of embodiments E38-E40, wherein the amount of the test compound is determined by detecting the test compound label.

E42. The method of any one of embodiments E1-E41, wherein the amount of the test compound is determined by mass spectrometry, liquid chromatography, and/or ultraviolet-visible spectrophotometry.

E43. A method of determining the partition characteristics of a plurality of test compounds in a target condensate, the method comprising performing the method of any one of embodiments E1-E42 with a plurality of test compounds.

E44. The method of embodiment E43, further comprising comparing the partition characteristics of a subset or all of the plurality of test compounds in the target condensate.

E45. The method of embodiment E44, further comprising identifying test compounds that have the same or similar partition characteristics in a target condensate.

E46. The method of embodiment E45, further comprising identifying a characteristic that a subset or all of the identified test compounds have in common in addition to the same or similar partition characteristics.

E47. The method of embodiment E46, further comprising determining the partition characteristic in a target condensate for one or more additional test compounds that comprise the identified characteristic.

E48. The method of embodiment E46 or E47, further comprising determining the partition characteristic in a target condensate for one or more additional test compounds that do not comprise the identified characteristic.

E49. A method of determining a relative partition characteristic of a test compound in a target condensate, the method comprising: (i) determining the partition characteristic of the test compound by performing the method of any one of embodiments E1-E42 with the test compound; (ii) determining the partition characteristic of a reference compound by performing the method of any one of embodiments E1-E42 with the reference compound; and (iii) calculating the ratio of the partition characteristics determined in (i) and (ii), thereby determining the relative partition characteristic of the test compound in the target condensate.

E50. The method of embodiment E49, wherein the test compound comprises a test compound label.

E51. The method of embodiment E50, wherein the reference compound is the test compound label.

E52. A method of determining relative partition characteristics of a plurality of test compounds in a target condensate, the method comprising: (1) performing the method of any one of embodiments E49-E51; and (2) repeating steps (i) and (iii) with a plurality of test compounds.

E53. The method of embodiment E52, further comprising comparing the relative partition characteristics in the target condensate of a subset or all of the plurality of test compounds.

E54. The method of embodiment E53, further comprising identifying test compounds that have the same or similar relative partition characteristics in the target condensate.

E55. The method of embodiment E54, further comprising identifying a characteristic that a subset or all of the identified test compounds have in common in addition to the same or similar relative partition characteristics.

E56. The method of embodiment E55, further comprising determining the relative partition characteristic in the target condensate for one or more additional test compounds that comprise the identified characteristic.

E57. The method of embodiment E55 or E56, further comprising determining the relative partition characteristic in the target condensate for one or more additional test compounds that do not comprise the identified characteristic.

E58. A method of determining a condensate preference profile of a test compound, the method comprising: (a) determining the partition characteristic of the test compound in a first target condensate using the method of any one of embodiments E1-E42; (b) determining the partition characteristic of the test compound in a second target condensate using the method of any one of embodiments E1-E42; and (c) calculating a ratio of the partition characteristic of the test compound determined in the first target condensate and the second target condensate, thereby determining the condensate preference profile of the test compound.

E59. The method of embodiment E58, wherein the first target condensate and the second target condensate are in the same composition.

E60. The method of embodiment E58, wherein the first target condensate and the second target condensate are in different compositions.

E61. The method of any one of embodiments E58-E60, wherein the partition characteristic of the test compound in the first target condensate is determined prior to, simultaneously with, or after the partition characteristic of the test compound in the second target condensate is determined.

E62. A method of determining a condensate preference profile of a test compound, the method comprising: (a) determining the relative partition characteristic of the test compound in a first target condensate using the method of any one of embodiments E49-E51; (b) determining the relative partition characteristic of the test compound in a second target condensate using the method of any one of embodiments E49-E51; and (c) calculating a ratio of the partition characteristic of the test compound determined in the first target condensate and the second target condensate, thereby determining the condensate preference profile of the test compound.

E63. The method of embodiment E62, wherein the first target condensate and the second target condensate are in the same composition.

E64. The method of embodiment E62, wherein the first target condensate and the second target condensate are in different compositions.

E65. The method of any one of embodiments E62-E64, wherein the relative partition characteristic of the test compound in the first target condensate is determined prior to, simultaneously with, or after the relative partition characteristic of the test compound in the second target condensate is determined.

E66. The method of any one of embodiments E58-E65, further comprising labeling the first target condensate and the second target condensate in order to visualize the first condensate target condensate and the second target condensate.

E67. The method of embodiment E66, wherein the first target condensate and the second target condensate are labeled with different labels.

E68. The method of any one of embodiments E58-E67, wherein the method comprises repeating the steps of the method for one or more additional target condensates.

E69. A method of determining condensate preference profiles of a plurality of test compounds, the method comprising performing the method of any one of embodiments E58-E68 with a plurality of test compounds.

E70. The method of embodiment E69, further comprising comparing condensate preference profiles of a subset or all of the plurality of test compounds.

E71. The method of embodiment E70, further comprising identifying test compounds that have the same or similar condensate preference profiles.

E72. The method of embodiment E71, further comprising identifying a characteristic that a subset or all of the identified test compounds have in common in addition to the same or similar condensate preference profiles.

E73. The method of embodiment E72, further comprising determining the relative partition characteristic for one or more additional test compounds that comprise the identified characteristic.

E74. The method of embodiment E72 or E73, further comprising determining the relative partition characteristic for one or more additional test compounds that do not comprise the identified characteristic.

E75. A method of identifying a compound characteristic associated with partitioning a compound into or out of a condensate, the method comprising: (a) determining partition characteristics of a plurality of test compounds in the target condensate by performing the method of embodiment E43; (b) comparing the partition characteristics of a subset or all of the plurality of test compounds in the target compound; (c) identifying test compounds that have the same or similar partition characteristics in the target condensate; and (d) identifying a characteristic that a subset or all of the identified test compounds have in common in addition to the same or similar partition characteristics.

E76. A method of identifying a compound characteristic associated with partitioning a compound into or out of a condensate, the method comprising: (a) determining relative partition characteristics of a plurality of test compounds in the target condensate by performing the method of embodiment E52; (b) comparing the relative partition characteristics of a subset or all of the plurality of test compounds in the target condensate; (c) identifying test compounds that have the same or similar relative partition characteristics in the target condensate; and (d) identifying a characteristic that a subset or all of the identified test compounds have in common in addition to the same or similar relative partition characteristics.

E77. A method of identifying a compound characteristic associated with partitioning a compound into or out of a condensate, the method comprising: (a) determining condensate preference profiles of a plurality of test compounds by performing the method of embodiment E69; (b) comparing the condensate preference profiles of a subset or all of the plurality of test compounds; (c) identifying test compounds that have the same or similar condensate preference profiles; and (d) identifying a characteristic that a subset or all of the identified test compounds have in common in addition to the same or similar condensate preference profiles.

E78. A method of designing a compound with a desired partition characteristic into or out of a target condensate, the method comprising: (a) determining partition characteristics of a plurality of test compounds in the target condensate by performing the method of embodiment E43; (b) comparing the partition characteristics of a subset or all of the plurality of test compounds in the target condensate; (c) identifying test compounds that have the same or similar partition characteristics in the target condensate; (d) identifying a characteristic that a subset or all of the identified test compounds have in common in addition to the same or similar partition characteristics; and (e)(i) designing a compound that comprises the identified characteristic; or (ii) designing a compound that does not comprise the identified characteristic, thereby designing a compound with the desired partition characteristic into or out of the target condensate.

E79. A method of designing a compound with a desired relative partition characteristic into or out of a target condensate, the method comprising: (a) determining relative partition characteristics of a plurality of test compounds in the target condensate by performing the method of embodiment E52; (b) comparing the relative partition characteristics of a subset or all of the plurality of test compounds in the target condensate; (c) identifying test compounds that have the same or similar relative partition characteristics in the target condensate; (d) identifying a characteristic that a subset or all of the identified test compounds have in common in addition to the same or similar relative partition characteristics; and (e)(i) designing a compound that comprises the identified characteristic; or (ii) designing a compound that does not comprise the identified characteristic, thereby designing a compound with the desired relative partition characteristic into or out of the target condensate.

E80. A method of designing a compound with a desired condensate preference profile, the method comprising: (a) determining condensate preference profiles of a plurality of test compounds by performing the method of embodiment E69; (b) comparing the condensate preference profiles of a subset or all of the plurality of test compounds; (c) identifying test compounds that have the same or similar condensate preference profiles; (d) identifying a characteristic that a subset or all of the identified test compounds have in common in addition to the same or similar condensate preference profiles; and (e)(i) designing a compound that comprises the identified characteristic; or (ii) designing a compound that does not comprise the identified characteristic, thereby designing a compound with the desired condensate preference profile.

E81. The method of any one of embodiments E78-E80, further comprising making the compound.

E82. A method of screening a test compound for a desired partition characteristic from a group of candidate compounds, the method comprising: (a) determining a partition characteristic of each of the group of candidate compounds; and (b) identifying the test compound having the desired partition characteristic.

E83. The method of embodiment E82, wherein the partition characteristic of each of the group of candidate compounds is determined in vitro.

E84. The method of embodiment E82 or E83, wherein the test compound has a suitable partition characteristic for being useful for treating a disease in an individual.

E85. A method of identifying a test compound useful for treating a disease in an individual in need thereof, the method comprising: (a) identifying a target condensate associated with the disease; and (b) determining a partition characteristic of a candidate compound in the target condensate, and (c) identifying the test compound having a suitable partition characteristic for being useful for treating the disease.

E86. A method of determining a partition characteristic of a test compound in a target condensate, the method comprising: (a) combining the test compound and a composition comprising the target condensate and an extra-condensate solution; (b) obtaining a reference control; (c) measuring a MS signal of the test compound in the extra-condensate solution, or a portion thereof, using a mass spectrometry technique; (d) measuring a MS signal of the test compound in the reference control, or a portion thereof, using a mass spectrometry technique; and (e) comparing the MS signal of the test compound from the extra-condensate solution and the MS signal of the test compound from the reference control, thereby determining the partition characteristic of the test compound in the target condensate.

E87. The method of E86, wherein the amount of the test compound combined with the composition is 100 nM or less, and the amount of a precursor molecule in the composition, including in the target condensate, is about 5 µM.

E88. A library comprising a plurality of compounds, wherein each compound of the plurality of compounds comprises the same moiety comprising a characteristic having a desired partition characteristic.

E89. A method of designing a test compound having a desired partition characteristic, the method comprising modifying a precursor of the test compound by attaching a moiety to the compound, wherein the moiety comprises a characteristic having a desired partition characteristic.

Those skilled in the art will recognize that several embodiments are possible within the scope and spirit of the disclosure of this application. The disclosure is illustrated further by the examples below, which are not to be construed as limiting the disclosure in scope or spirit to the specific procedures described therein.

EXAMPLES

Example 1

Characterization of One or More Compounds in Solution-Based Condensates

Condensates are formed in a solution. For example, a solution comprising a high concentration of salt and a high concentration of one or more protein capable of forming a condensate are diluted into a buffer that mimics physiological salt conditions.

Alternatively, a solution comprising one or more proteins capable of forming a condensate is diluted into a buffer and a crowding agent is added. In one specific embodiment, proteins capable of forming a condensate are mixed with 10% Dextran in a buffer containing 25 mM Tris-HCl (pH 7.4), 150 mM KCl, 2.5% glycerol, and 0.5 mM DTT.

A test compound is added to the solution before or after condensate formation. When added after condensate formation, the solution is incubated to allow partitioning of the test compound.

The density of condensates is typically greater than the surrounding solution, so the condensate is allowed to sediment. In some instances, the condensate is imaged. For example, a dye or a labeled protein that is known to concentrate in the condensate is used to visualize the condensate.

In some instances, the supernatant liquid is removed from the condensate. In some instances, the supernatant liquid is analyzed to determine the amount of compound present.

The condensate is analyzed to determine the amount of compound present. In some instances, the ratio of compound in the condensate to compound in the supernatant is calculated.

Example 2

Characterization of Dye Compounds in Solution-Based FUS and PGL-3 Condensates

A variety of exemplary test compounds were assayed using exemplary methods to determine partition characteristics, relative partition characteristics, and condensate preference profiles. For this example, the exemplary test compounds used were dyes; however test compounds are not limited to dyes. The entire procedure was performed twice in two independent experiments on different days and in different orders.

Sample Preparation

All dye-stocks were stored as 1 mM solutions in 100% DMSO. The dyes used are shown in Table 1. The dyes were dissolved in dilution buffer (DB: 14.7 mM Tris, pH 7.25, 1 mM DTT) to yield 11.765 µM dye in 1.1765 DMSO. 17 µl of dye was distributed in a 384 well non-binding plate (Greiner).

TABLE 1

Assayed dyes.

| DYE # | NAME | STRUCTURE | CHANNEL |
|---|---|---|---|
| 1 | DAPI | 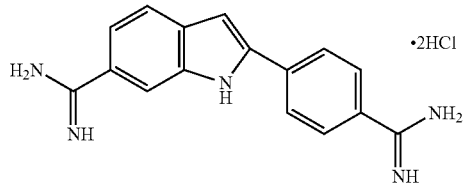 [SMILES: N=C(N)c1ccc(-c2cc3ccc(C(=N)N)cc3[nH]2)cc1] | 405 |

TABLE 1-continued

Assayed dyes.

| DYE # | NAME | STRUCTURE | CHANNEL |
|---|---|---|---|
| 2 | 7-Hydroxy-4-(trifluoromethyl) coumarin | 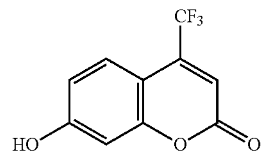 [SMILES: O=c1cc(C(F)(F)F)c2ccc(O)cc2o1] | 405 |
| 3 | Coumarin 343 | 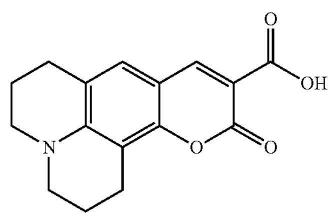 [SMILES: O=C(O)c1cc2cc3c4c(c2oc1=O)CCCN4CCC3] | 405 |
| 4 | Coumarin 334 | 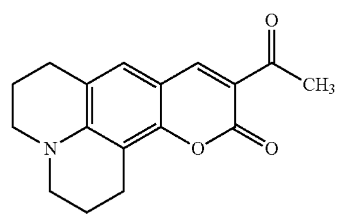 [SMILES: CC(=O)c1cc2cc3c4c(c2oc1=O)CCCN4CCC3] | 488 |
| 5 | Fluorescein mono-(N-acetyl-β-D-galactosaminide) | 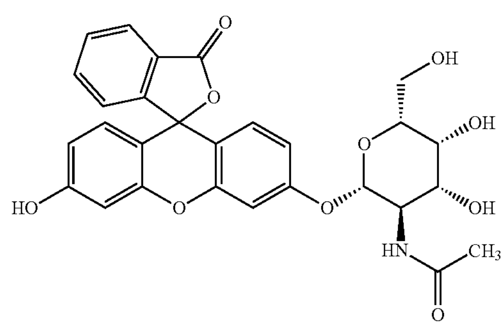 [SMILES: CC(=O)N[C@H]1[C@H](Oc2ccc3c(c2)Oc2cc(O)ccc2C32OC(=O)c3ccccc32)O[C@H](CO)[C@H](O)[C@@H]1O] | 488 |
| 6 | Fluorescein | 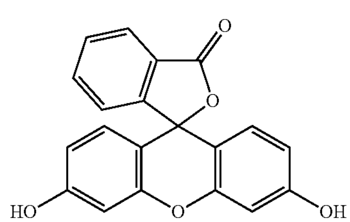 [SMILES: O=C1OC2(c3ccc(O)cc3Oc3cc(O)ccc32)c2ccccc21] | 488 |
| 7 | Fluorescein dilaurate | 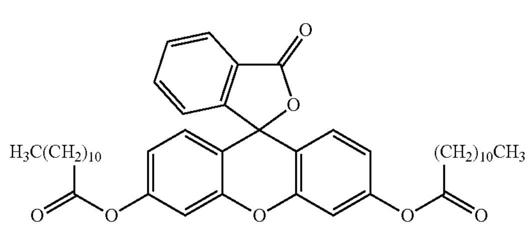 | 488 |

TABLE 1-continued

Assayed dyes.

| DYE # | NAME | STRUCTURE | CHANNEL |
|---|---|---|---|
| 8 | 6-[Fluorescein-5(6)-carboxamido]hexanoic acid | 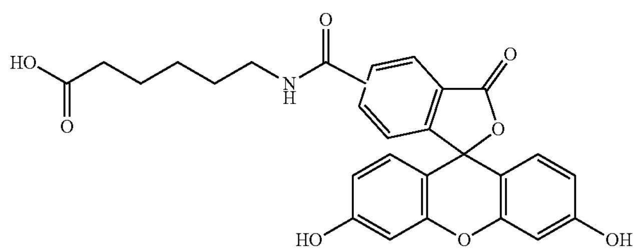 | 488 |
| 9 | Fluorescein diacetate | 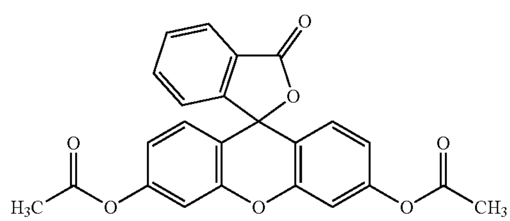 [SMILES: CC(=O)Oc1ccc2c(c1)Oc1cc(OC(C)=O)ccc1C21OC(=O)c2ccccc21] | 488 |
| 10 | Polysucrose 40-fluorescein isothiocyanate conjugate | 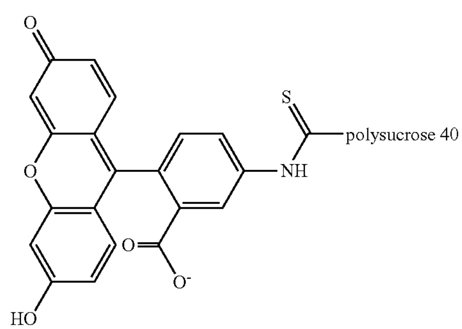 | 488 |
| 11 | Fluorescein-12-UTP | 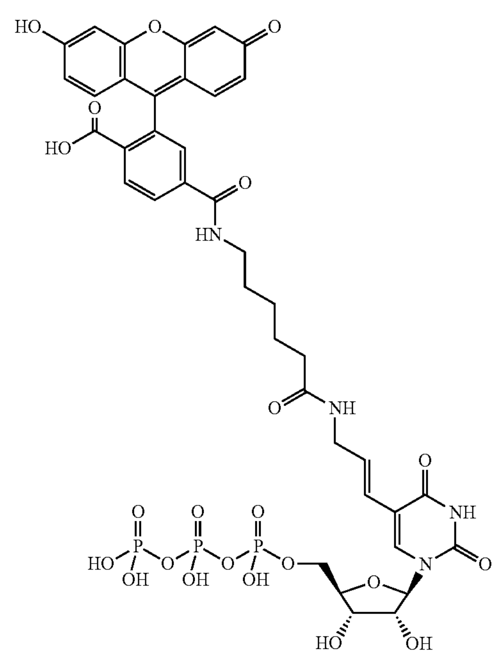 [SMILES: O=C(CCCCCNC(=O)c1ccc(C(=O)O)c(-c2c3ccc(=O)cc-3oc3cc(O)ccc23)c1)NC/C=C/c1cn([C@@H]2O[C@H](COP(=O)(O)OP(=O)(O)OP(=O)(O)O)[C@@H](O)[C@H]2O)c(=O)[nH]c1=O] | 488 |

TABLE 1-continued

Assayed dyes.

| DYE # | NAME | STRUCTURE | CHANNEL |
|---|---|---|---|
| 12 | Fluorescein di(β-D-galactopyranoside) | 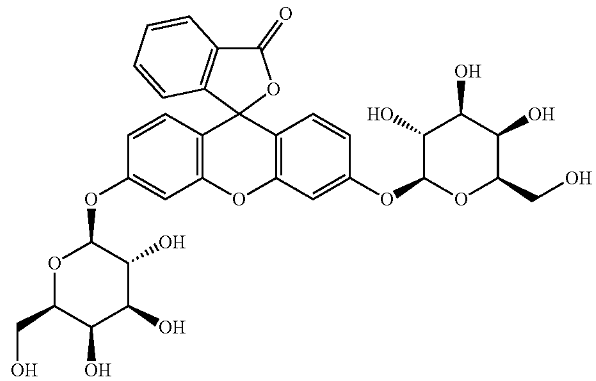 [SMILES: O=C1OC2(c3ccc(O[C@@H]4O[C@H](CO)[C@H](O)[C@H](O)[C@H]4O)cc3Oc3cc(O[C@@H]4O[C@H](CO)[C@H](O)[C@H](O)[C@H]4O)ccc32)c2ccccc21] | 488 |
| 13 | Biotin-4-Fluoroscein | 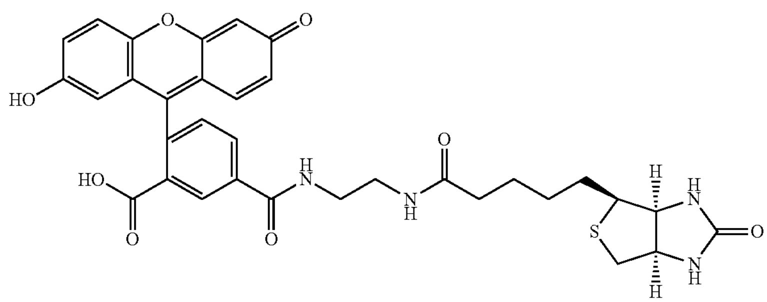 [SMILES: O=C(CCCC[C@@H]1SC[C@@H]2NC(=O)N[C@@H]21)NCCNC(=O)c1ccc(-c2c3ccc(=O)cc-3oc3ccc(O)cc23)c(C(=O)O)c1] | 488 |
| 14 | Rhodamine 123 | 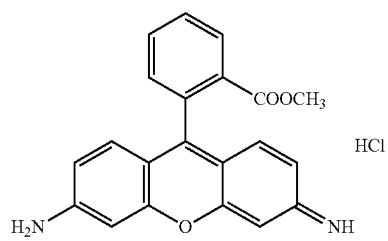 [SMILES: COC(=O)c1ccccc1-c1c2ccc(=N)cc-2oc2cc(N)ccc12 ; Cl] | 488 |
| 15 | N-(8-Amino-3,6-dioxaoctyl)rhodamine 6G-amine bis(trifluoroacetate) | 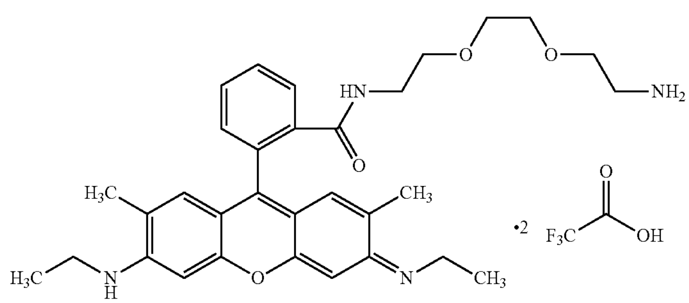 [SMILES: CC/N=c1/cc2oc3cc(NCC)c(C)cc3c(-c3ccccc3C(=O)NCCOCCOCCN)c-2cc1C ; O=C(O)C(F)(F)F] | 488 |
| 16 | Rhodamine B | 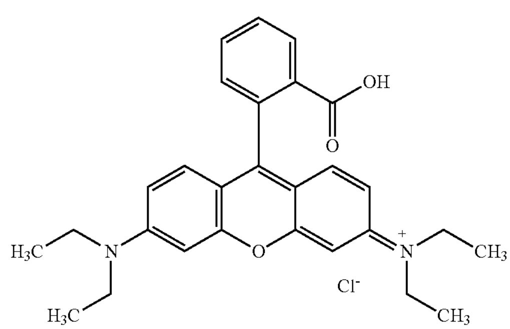 | 561 |

TABLE 1-continued

Assayed dyes.

| DYE # | NAME | STRUCTURE | CHANNEL |
|---|---|---|---|
| 17 | Rhodamine 101 inner salt | 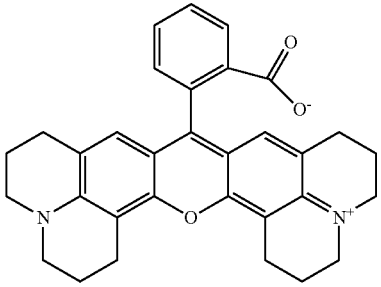 [SMILES: O=C([O-])c1ccccc1C1=c2cc3c4c(c2Oc2c1cc1c5c2CCCN5CCC1)CCC[N+]=4CCC3] | 561 |
| 18 | Rhodamine 800 | 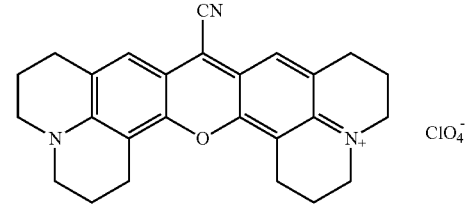 | 640 |

Either SNAP-tagged FUS protein or tag-free PGL-3 protein was thawed at room temperature for at least 10 min, and the buffer was exchanged to partitioning buffer (PB: 50 mM Tris pH 7.25, 500 mM KCl, 5% Glycerol, and 1 mM DTT). The protein was then diluted to 33.3 µM in PB. 3 µl of protein solution were added to the 384 well plate to initiate phase separation, yielding 20 µl of 5 µM protein and 10 µM dye in 75 mM KCl, 0.75% Glycerol, 20 mM Tris, 1 mM DTT, and 1% DMSO or for no dye control reactions, 20 µl of 5 µM protein in 75 mM KCl, 0.75% Glycerol, 20 mM Tris, 1 mM DTT.

Imaging

A spinning disk confocal microscope was used to acquire images of the samples. A 60× oil high-NA objective lens was used to capture the condensate droplets. The laser power was set to 20% and the exposure times were adjusted to the fluorescence emission intensity specific for each dye. Exposure times ranged from 1-1000 ms. Appropriate filter settings were used, matching the excitation and emission spectra of the respective dyes. The channels used for each dye are shown in Table 1. Three images per well were taken.

Exemplary images are shown in FIG. 1. The background signal of protein droplets in the absence of dye was recorded for all applied imaging conditions.

Image and Data Analysis

Figure 2A:
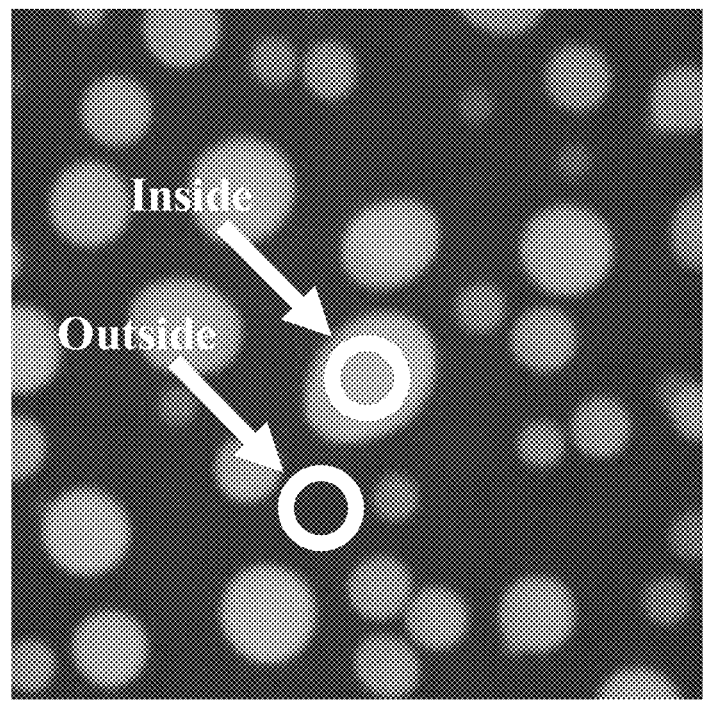
FIGS. 2A and 2B depict the regions inside and outside exemplary condensates that were chosen to measure intensities in the presence (FIG. 2A) and absence of dye (FIG. 2B).
Figure 2B:
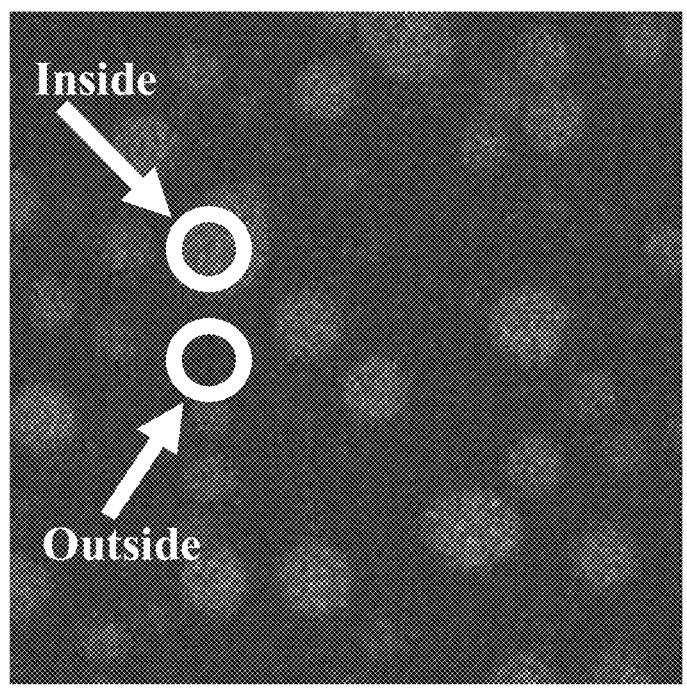

Fluorescence intensity was measured inside one exemplary target condensate (Intensity inside, I-in) per image and in a region next to the exemplary target condensate (Intensity outside, I-out) by hand using the image analysis software Fiji. An example depicting the regions measured is shown FIG. 2A. Three I-in and three I-out values were measured in total for each dye in each experiment and were averaged. The measured I-in and I-out values for FUS-SNAP condensates on one day of experiments are shown in Table 2 and Table 3, respectively. The measured I-in and I-out values for PGL-3 condensates on one day of experiments are shown in Table 4 and Table 5, respectively. All values were background corrected, based on the background images (no dye controls) taken with the same microscope conditions. An exemplary background image is shown in FIG. 2B and measured I-in or I-out background measurements are shown in Tables 3-5.

TABLE 2

Measurements of dyes inside FUS-SNAP condensates.

| Dye # | Intensity Inside with Dye | | | | Intensity Inside with No Dye | | | Intensity Inside Dye-No Dye |
|---|---|---|---|---|---|---|---|---|
| | 1 | 2 | 3 | Average | 1 | 2 | Average | |
| 1 | 638.5 | 599.9 | 628.8 | 622.4 | 120.6 | 119.3 | 120.0 | 502.4 |
| 2 | 278.2 | 278.1 | 286.5 | 280.9 | 120.6 | 119.3 | 120.0 | 160.9 |
| 3 | 3451.6 | 3462.2 | 3804.4 | 3572.7 | 120.6 | 119.3 | 120.0 | 3452.8 |
| 4 | 10755.9 | 10738.6 | 11058.9 | 10851.1 | 503.3 | 491.9 | 497.6 | 10353.6 |
| 5 | 2046.8 | 2005.1 | 1638.1 | 1896.7 | 503.3 | 491.9 | 497.6 | 1399.1 |
| 6 | 6328.8 | 6300.8 | 6201.7 | 6277.1 | 131.8 | 138.6 | 135.2 | 6141.9 |
| 7 | 548.7 | 492.0 | 481.3 | 507.3 | 503.3 | 491.9 | 497.6 | 9.7 |
| 8 | 5285.1 | 5631.6 | 5148.0 | 5354.9 | 131.8 | 138.6 | 135.2 | 5219.7 |
| 9 | 5836.4 | 6036.1 | 6229.9 | 6034.1 | 4134.6 | 4290.7 | 4212.6 | 1821.5 |
| 10 | 6139.7 | 6105.5 | 5024.6 | 5756.6 | 131.8 | 138.6 | 135.2 | 5621.4 |
| 11 | 13042.4 | 13375.9 | 12572.2 | 12996.8 | 131.8 | 138.6 | 135.2 | 12861.6 |

TABLE 2-continued

Measurements of dyes inside FUS-SNAP condensates.

| Dye # | Intensity Inside with Dye | | | | Intensity Inside with No Dye | | | Intensity Inside Dye-No Dye |
|---|---|---|---|---|---|---|---|---|
| | 1 | 2 | 3 | Average | 1 | 2 | Average | |
| 12 | 456.2 | 508.6 | 469.3 | 478.0 | 503.3 | 491.9 | 497.6 | −19.5 |
| 13 | 4600.2 | 4189.8 | 5218.3 | 4669.4 | 131.8 | 138.6 | 135.2 | 4534.2 |
| 14 | 3123.1 | 2956.9 | 2831.2 | 2970.4 | 131.8 | 138.6 | 135.2 | 2835.2 |
| 15 | 3084.2 | 3756.7 | 3599.3 | 3480.0 | 4134.6 | 4290.7 | 4212.6 | −732.6 |
| 16 | 2154.5 | 2074.7 | 1895.0 | 2041.4 | 99.7 | 99.6 | 99.6 | 1941.7 |
| 17 | 4695.6 | 5663.6 | 4511.0 | 4956.7 | 99.7 | 99.6 | 99.6 | 4857.1 |
| 18 | 15394.5 | 13908.5 | 15851.1 | 15051.4 | 129.9 | 133.8 | 131.9 | 14919.5 |

TABLE 3

Measurements of dyes outside FUS-SNAP condensates.

| Dye # | Intensity Outside with Dye | | | | Intensity Outside with No Dye | | | Intensity Outside (Dye-No Dye) |
|---|---|---|---|---|---|---|---|---|
| | 1 | 2 | 3 | Average | 1 | 2 | Average | |
| 1 | 233.9 | 233.3 | 218.7 | 228.6 | 120.1 | 120.1 | 120.1 | 108.6 |
| 2 | 235.7 | 228.5 | 232.0 | 232.0 | 120.1 | 120.1 | 120.1 | 112.0 |
| 3 | 1486.5 | 1529.0 | 1479.6 | 1498.4 | 120.1 | 120.1 | 120.1 | 1378.3 |
| 4 | 4894.0 | 5118.6 | 5078.2 | 5030.3 | 140.3 | 139.8 | 140.0 | 4890.2 |
| 5 | 1319.4 | 1306.9 | 1191.0 | 1272.5 | 140.3 | 139.8 | 140.0 | 1132.4 |
| 6 | 3771.1 | 3840.2 | 3742.7 | 3784.7 | 104.3 | 103.8 | 104.0 | 3680.6 |
| 7 | 141.6 | 135.4 | 138.4 | 138.5 | 140.3 | 139.8 | 140.0 | −1.6 |
| 8 | 3064.0 | 3267.0 | 3205.5 | 3178.8 | 104.3 | 103.8 | 104.0 | 3074.8 |
| 9 | 1487.5 | 1414.8 | 1552.6 | 1485.0 | 519.0 | 581.2 | 550.1 | 934.8 |
| 10 | 5878.5 | 5846.2 | 4791.0 | 5505.3 | 104.3 | 103.8 | 104.0 | 5401.2 |
| 11 | 2423.6 | 3035.6 | 2255.1 | 2571.4 | 104.3 | 103.8 | 104.0 | 2467.4 |
| 12 | 150.1 | 142.8 | 152.9 | 148.6 | 140.3 | 139.8 | 140.0 | 8.5 |
| 13 | 2286.6 | 2244.6 | 2195.6 | 2242.3 | 104.3 | 103.8 | 104.0 | 2138.2 |
| 14 | 2174.8 | 2322.7 | 2335.1 | 2277.6 | 104.3 | 103.8 | 104.0 | 2173.5 |
| 15 | 559.0 | 527.6 | 532.7 | 539.8 | 519.0 | 581.2 | 550.1 | −10.3 |
| 16 | 546.8 | 508.3 | 565.6 | 540.2 | 100.0 | 99.9 | 99.9 | 440.3 |
| 17 | 808.3 | 1011.5 | 887.5 | 902.4 | 100.0 | 99.9 | 99.9 | 802.5 |
| 18 | 2064.2 | 1988.2 | 2224.3 | 2092.2 | 133.8 | 130.8 | 132.3 | 1959.9 |

TABLE 4

Measurements of dyes inside PGL-3 condensates.

| Dye # | Intensity Inside with Dye | | | | Intensity Inside with No Dye | | | Intensity Inside (Dye-No Dye) |
|---|---|---|---|---|---|---|---|---|
| | 1 | 2 | 3 | Average | 1 | 2 | Average | |
| 1 | 211.3 | 211.0 | 215.7 | 212.6 | 121.1 | 120.4 | 120.8 | 91.9 |
| 2 | 273.9 | 267.0 | 268.3 | 269.8 | 121.1 | 120.4 | 120.8 | 149.0 |
| 3 | 2228.4 | 2006.3 | 2059.4 | 2098.0 | 121.1 | 120.4 | 120.8 | 1977.3 |
| 4 | 212.2 | 205.0 | 197.2 | 204.8 | 121.1 | 120.4 | 120.8 | 84.0 |
| 5 | 1912.6 | 1794.0 | 1797.0 | 1834.5 | 615.1 | 579.4 | 597.2 | 1237.3 |
| 6 | 4585.4 | 4501.5 | 4119.2 | 4402.0 | 146.6 | 146.4 | 146.5 | 4255.5 |
| 7 | 784.6 | 785.3 | 792.4 | 787.4 | 615.1 | 579.4 | 597.2 | 190.2 |
| 8 | 3527.5 | 3608.1 | 3480.3 | 3538.6 | 146.6 | 146.4 | 146.5 | 3392.1 |
| 9 | 824.1 | 801.2 | 860.4 | 828.6 | 615.1 | 579.4 | 597.2 | 231.3 |
| 10 | 5747.5 | 6281.4 | 4996.0 | 5674.9 | 146.6 | 146.4 | 146.5 | 5528.4 |
| 11 | 2451.3 | 2688.1 | 2362.8 | 2500.7 | 146.6 | 146.4 | 146.5 | 2354.2 |
| 12 | 689.4 | 656.9 | 723.9 | 690.1 | 615.1 | 579.4 | 597.2 | 92.8 |
| 13 | 2939.4 | 3141.8 | 3035.4 | 3038.9 | 146.6 | 146.4 | 146.5 | 2892.4 |
| 14 | 2874.7 | 2858.2 | 2900.3 | 2877.7 | 146.6 | 146.4 | 146.5 | 2731.2 |
| 15 | 6831.9 | 6829.0 | 5802.8 | 6487.9 | 4477.7 | 6041.9 | 5259.8 | 1228.1 |
| 16 | 5570.5 | 6179.8 | 5579.3 | 5776.5 | 101.5 | 101.6 | 101.5 | 5675.0 |
| 17 | 12579.6 | 14061.0 | 12561.8 | 13067.5 | 101.5 | 101.6 | 101.5 | 12966.0 |
| 18 | 714.9 | 700.1 | 777.4 | 730.8 | 125.2 | 127.2 | 126.2 | 604.6 |

TABLE 5

Measurements of dyes outside PGL-3 condensates.

| Dye # | Intensity Outside with Dye | | | | Intensity Outside with No Dye | | | Intensity Outside (Dye-No Dye) |
|---|---|---|---|---|---|---|---|---|
| | 1 | 2 | 3 | Average | 1 | 2 | Average | |
| 1 | 173.1 | 168.4 | 164.9 | 168.8 | 120.1 | 120.8 | 120.4 | 48.4 |
| 2 | 263.1 | 258.0 | 266.0 | 262.4 | 120.1 | 120.8 | 120.4 | 141.9 |
| 3 | 1472.5 | 1407.6 | 1461.1 | 1447.1 | 120.1 | 120.8 | 120.4 | 1326.6 |
| 4 | 178.0 | 179.6 | 179.5 | 179.0 | 120.1 | 120.8 | 120.4 | 58.6 |
| 5 | 1439.0 | 1386.2 | 1353.5 | 1392.9 | 165.2 | 160.6 | 162.9 | 1230.0 |
| 6 | 4395.6 | 4190.8 | 3912.1 | 4166.2 | 105.7 | 105.0 | 105.3 | 4060.8 |
| 7 | 215.9 | 212.1 | 214.8 | 214.2 | 165.2 | 160.6 | 162.9 | 51.3 |
| 8 | 3491.4 | 3551.4 | 3447.6 | 3496.8 | 105.7 | 105.0 | 105.3 | 3391.4 |
| 9 | 269.6 | 264.9 | 273.2 | 269.2 | 165.2 | 160.6 | 162.9 | 106.3 |
| 10 | 5900.4 | 6581.6 | 5199.5 | 5893.8 | 105.7 | 105.0 | 105.3 | 5788.5 |
| 11 | 2174.3 | 2443.9 | 2108.6 | 2242.3 | 105.7 | 105.0 | 105.3 | 2137.0 |
| 12 | 208.4 | 203.2 | 207.7 | 206.4 | 165.2 | 160.6 | 162.9 | 43.5 |
| 13 | 2781.8 | 2905.7 | 2825.1 | 2837.5 | 105.7 | 105.0 | 105.3 | 2732.2 |
| 14 | 2628.3 | 2616.4 | 2545.0 | 2596.6 | 105.7 | 105.0 | 105.3 | 2491.2 |
| 15 | 1289.1 | 1266.2 | 1236.3 | 1263.8 | 671.5 | 744.9 | 708.2 | 555.7 |
| 16 | 3907.8 | 4226.6 | 4131.5 | 4088.7 | 101.3 | 101.6 | 101.5 | 3987.2 |
| 17 | 7184.0 | 7157.1 | 7012.6 | 7117.9 | 101.3 | 101.6 | 101.5 | 7016.4 |
| 18 | 301.3 | 294.6 | 332.2 | 309.4 | 128.7 | 132.7 | 130.7 | 178.7 |

Figure 3:
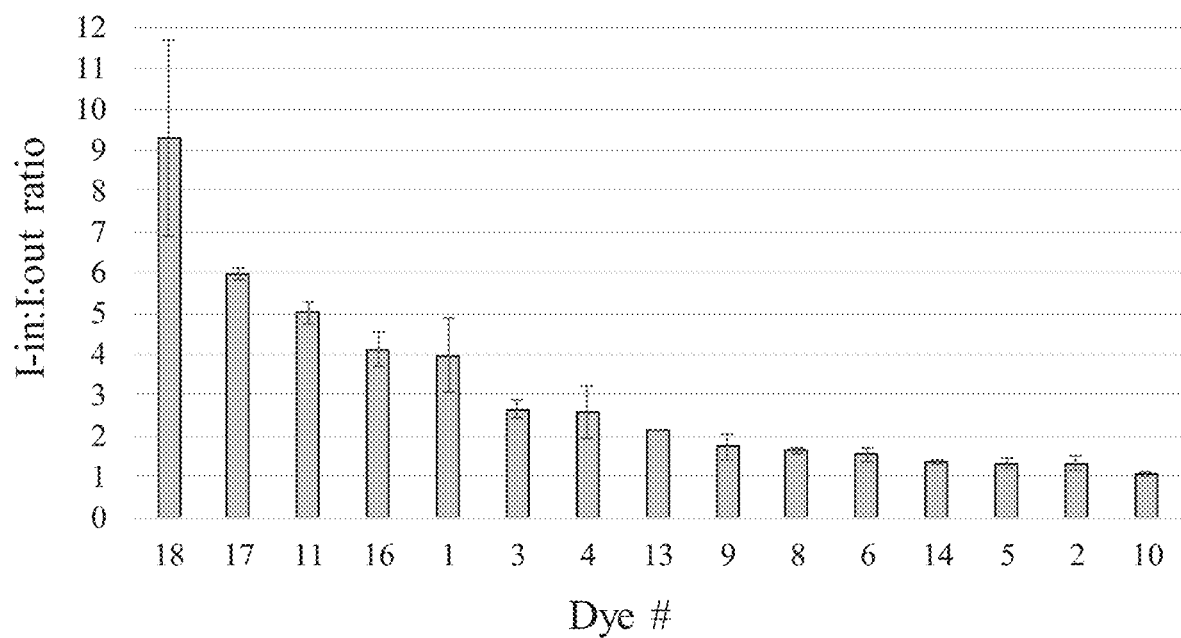
FIG. 3 shows the average intensity-in to intensity-out (I-in:I-out) ratios determined for each dye in FUS-SNAP condensates from two different days of experiments. Error bars show standard deviation of the two independent experiments.
Figure 4:
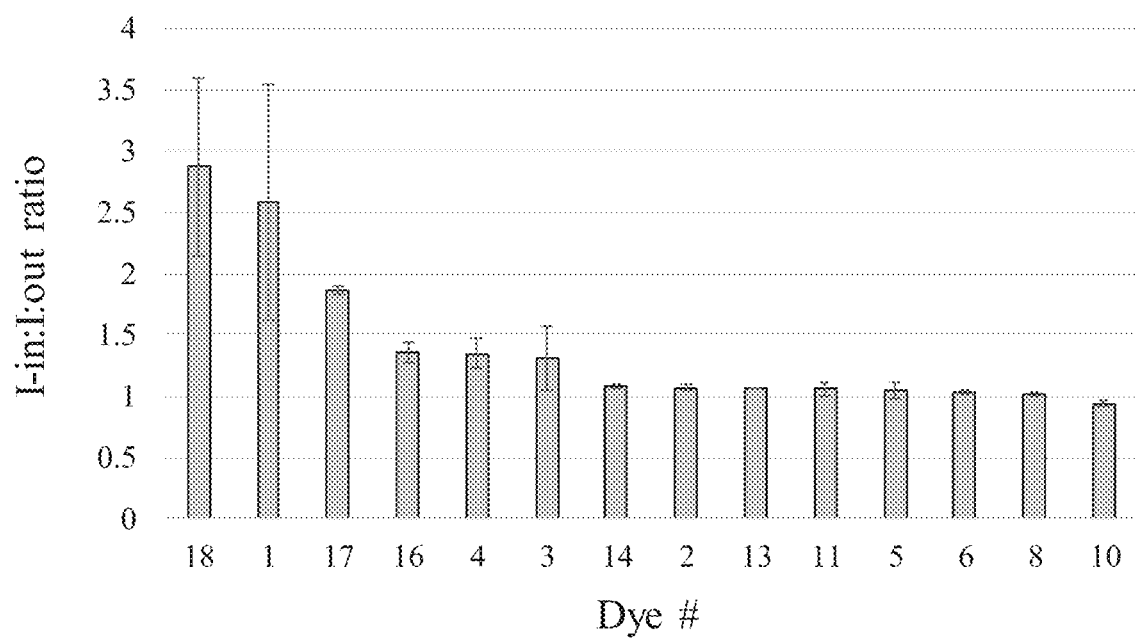
FIG. 4 shows the average intensity-in to intensity-out (I-in:I-out) ratios determined for each dye in PGL-3 condensates from two different days of experiments. Error bars show standard deviation of the two independent experiments.

The ratios of the average intensity measured in the target condensates and outside of the target condensates were calculated by dividing I-in by I-out, although dividing I-out by I-in could also have been used. The I-in:I-out ratios determined from the two different days of experiments were then averaged. The individual day and averaged I-in:I-out ratios are shown in Table 6. The average I-in:I-out ratios for FUS-SNAP condensates are shown in FIG. 3 and the average I-in:I-out ratios for PGL-3 condensates are shown in FIG. 4. The standard deviation between the two experiments is represented by the error bars in FIG. 3 and FIG. 4.

Figure 5:
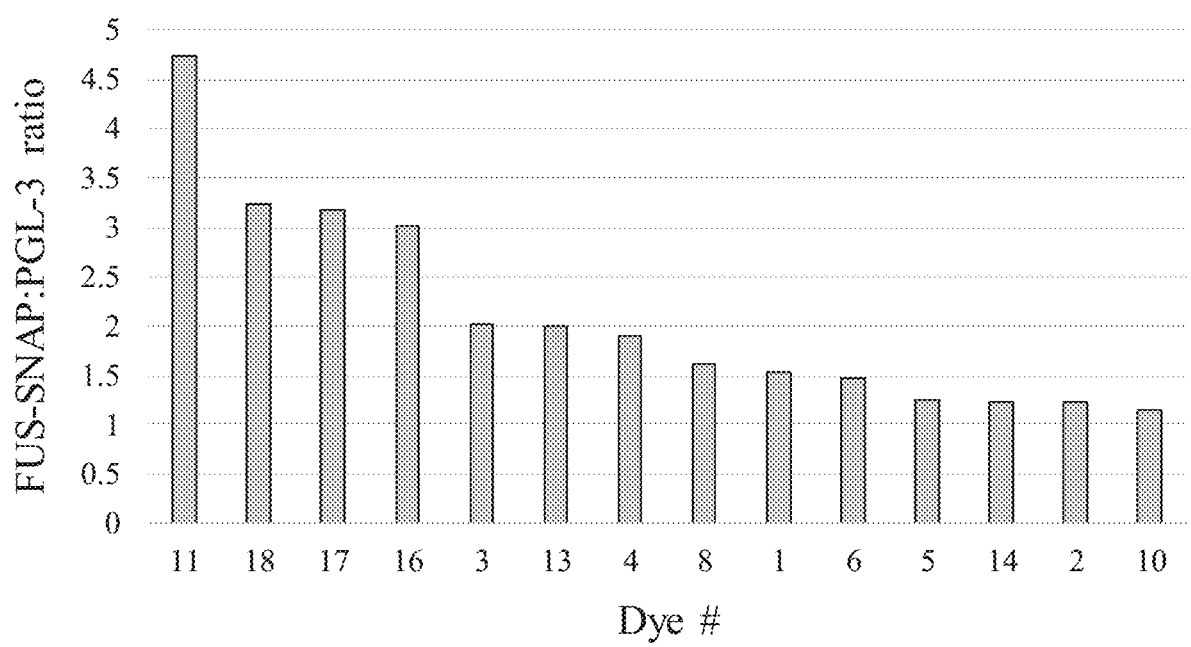
FIG. 5 shows the ratios of the average I-in:I-out ratio for each dye in FUS-SNAP condensates to the ratios of the average I-in:I-out ratio for each dye in PGL-3 condensates (FUS-SNAP:PGL-3 ratio).

The ratio of FUS-SNAP I-in:I-out to PGL-3 I-in:I-out was also calculated and is shown in Table 6 and FIG. 5.

TABLE 6

Calculated ratios of dye intensity.

| | Ratio of intensity inside:outside | | | | | | | Ratio of FUS-SNAP:PGL-3 |
|---|---|---|---|---|---|---|---|---|
| | FUS-SNAP Condensates | | | | PGL-3 Condensates | | | |
| Dye # | Day 1 | Day 2 | Average | Standard Deviation | Day 1 | Day 2 | Average | Standard Deviation |  |
| 1 | 4.6 | 3.3 | 4.0 | 0.9 | 1.9 | 3.3 | 2.6 | 1.0 | 1.5 |
| 2 | 1.4 | 1.2 | 1.3 | 0.2 | 1.0 | 1.1 | 1.1 | 0.0 | 1.2 |
| 3 | 2.5 | 2.8 | 2.7 | 0.2 | 1.5 | 1.1 | 1.3 | 0.3 | 2.0 |
| 4 | 2.1 | 3.0 | 2.6 | 0.6 | 1.4 | 1.3 | 1.3 | 0.1 | 1.9 |
| 5 | 1.2 | 1.4 | 1.3 | 0.1 | 1.0 | 1.1 | 1.1 | 0.1 | 1.3 |
| 6 | 1.7 | 1.4 | 1.5 | 0.2 | 1.0 | 1.0 | 1.0 | 0.0 | 1.5 |
| 7 | −6.2 | N/A | N/A | N/A | 3.7 | −4.1 | N/A | N/A | N/A |
| 8 | 1.7 | 1.6 | 1.6 | 0.1 | 1.0 | 1.0 | 1.0 | 0.0 | 1.6 |
| 9 | 1.9 | 1.5 | 1.7 | 0.3 | 2.2 | −0.4 | N/A | N/A | N/A |
| 10 | 1.0 | 1.1 | 1.1 | 0.0 | 1.0 | 0.9 | 0.9 | 0.0 | 1.1 |
| 11 | 5.2 | 4.8 | 5.0 | 0.3 | 1.1 | 1.0 | 1.1 | 0.1 | 4.7 |
| 12 | −2.3 | N/A | N/A | N/A | 2.1 | 1.9 | N/A | N/A | N/A |
| 13 | 2.1 | 2.1 | 2.1 | 0.0 | 1.1 | 1.1 | 1.1 | 0.0 | 2.0 |
| 14 | 1.3 | 1.4 | 1.3 | 0.0 | 1.1 | 1.1 | 1.1 | 0.0 | 1.2 |
| 15 | 70.8 | N/A | N/A | N/A | N/A | 3.3 | N/A | N/A | N/A |
| 16 | 4.4 | 3.8 | 4.1 | 0.4 | 1.4 | 1.3 | 1.4 | 0.1 | 3.0 |
| 17 | 6.1 | 5.9 | 6.0 | 0.1 | 1.8 | 1.9 | 1.9 | 0.0 | 3.2 |
| 18 | 7.6 | 11.0 | 9.3 | 2.4 | 3.4 | 2.4 | 2.9 | 0.7 | 3.2 |

N/A: not applicable, because the error was too large due to low signal of dye.

All compounds tested appear to be preferably partitioned into FUS-SNAP condensates over condensates formed by PGL-3. Compound #1 (DAPI), #11 (Fluorescein-12-UTP), #16 (Rhodamine B), #17 (Rhodamine 101 inner salt) and #18 (Rhodamine 800) has a I-in:I-out ratio for FUS-SNAP condensates of 4 or higher. Compounds #11, #16, #17, and #18 preferentially partitioned in FUS-SNAP condensates compared to PGL-3 with a ratio of 3 or higher.

Example 3

Co-Localization of Partitioned Compounds and FUS in FUS Condensates

To confirm that compounds that were partitioned into condensates in Example 2 were partitioned into condensates that contain FUS, Dye #18 (Rhodamine 800), which had an average I-in:I-out ratio of 9.3, was further assessed.

Sample Preparation

FUS-GFP condensates were prepared as described for FUS-SNAP in Example 2 using Dye 18.

Imaging

A spinning disk confocal microscope was used to acquire images of the samples. A 60× oil high-NA objective lens was used to capture the condensate droplets. The laser power was set to 20% and the exposure times were adjusted to the fluorescence emission intensity specific for each dye. Exposure times ranged from 1-1000 ms. Appropriate filter settings were used, matching the excitation and emission spectra of the dye and GFP. Control images were taken of condensates containing FUS-GFP with no dye.

Results

Figure 6:
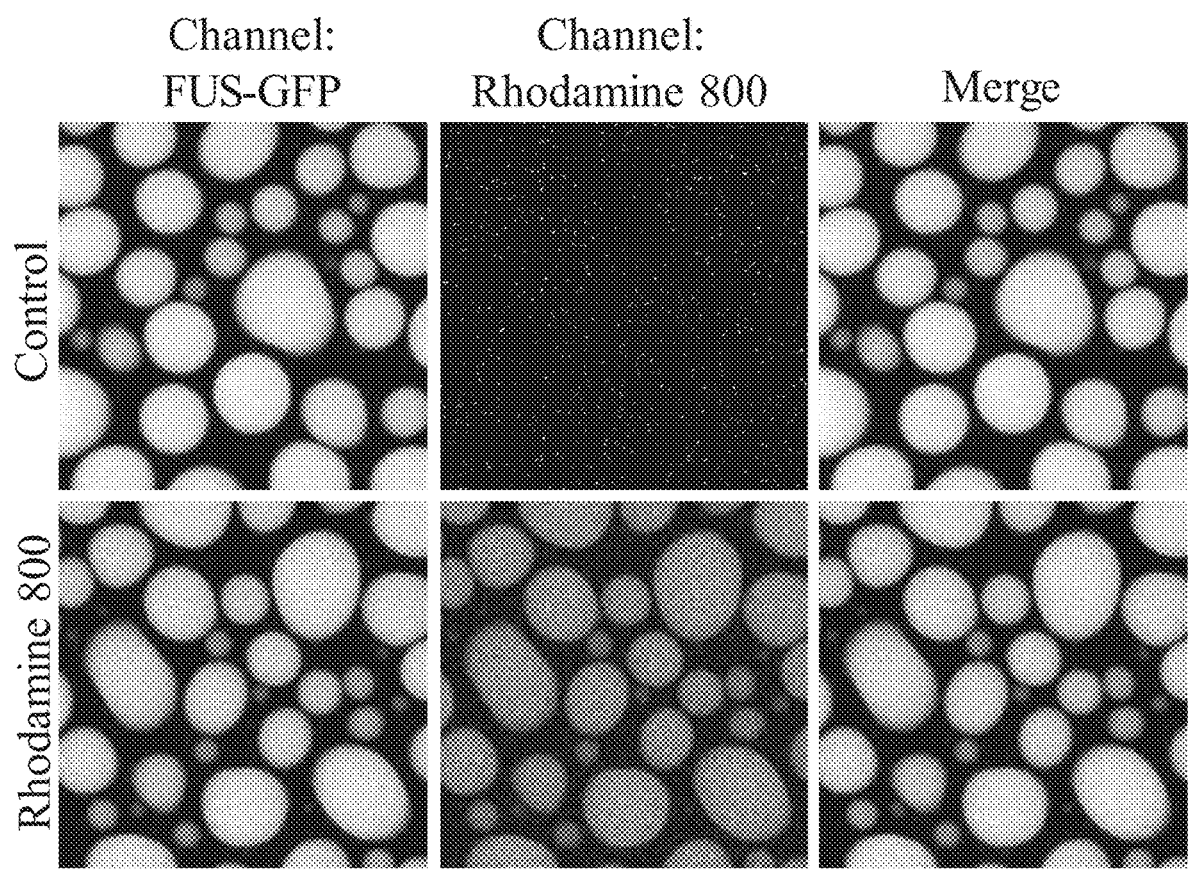
FIG. 6 shows fluorescent images of GFP-tag labeled FUS condensates in the presence or absence of Rhodamine 800 using a FUS-GFP channel, a Rhodamine 800 channel, and a merge of the other images.

The resulting images are shown in FIG. 6. GFP-labeled FUS was detected in condensates in the presence or absence of dye. Dye 18 was detected in condensates and the FUS protein and the dye were co-localized in the condensates. For no dye controls, fluorescence was not detected in the condensates when the Rhodamine 800 channel was used to acquire the images.

Example 4

Determining a Partition Characteristic of a Set of Compounds Using a Mass Spectrometry Assay A mass spectrometry-based method was developed to measure partition characteristics of exemplary test compounds. The measurements from the mass spectrometry-based method were compared to measurements obtained using the fluorescence-based assay disclosed in Example 2.

Methods

Protein Buffer was prepared (50 mM Tris, pH 7.25, 500 mM KCl, 1 mM DTT, and 5% glycerol). The high salt concentration of Protein Buffer prevents phase separation of macromolecules, e.g., proteins, contained therein. 20 µl aliquots of 70 µM FUS-SNAP protein stock solution were prepared in Protein Buffer. The aliquots of FUS-SNAP protein stock solution were frozen and stored prior to use. Dilution Buffer was prepared (14.7 mM Tris, pH 7.25, and 1 mM DTT).

Aliquots of 70 µM FUS-SNAP protein stock solution were thawed at room temperature for about 10 minutes. The aliquots of protein stock solution appeared clear with no visible precipitates. The thawed protein stock solution were filtered using centrifugation filters (Millipore, UFC30VV00). In brief, the aliquots of protein stock solution were added to a centrifugation filed and centrifuged for 1 minutes at 20,000 rcf at room temperature. The flow-through was collected. The protein concentration of the flow-through was measured and a solution of 33.3 µM FUS-SNAP was prepared by diluting the filtered flow-through and Dilution Buffer.

40 µL test reactions were prepared inside a PCR-tube or a PCR-strip (8 wells; AXYGEN™ 8-Strip PCR Tubes, 0.2 mL) using the following: (i) 34 µL Dilution Buffer, with the test compound at a given concentration, and with DMSO to obtain a final DMSO concentration of 1%, and (ii) 6 µL of 33.3 µM FUS-SNAP filtered protein solution. The final concentration of the 40 µL reactions were 5 µM FUS-SNAP, 75 mM KCl, 20 mM Tris, 0.75% Glycerol, 1 mM DTT, 1% DMSO, and, for the reactions containing a test compound, the desired test compound concentration.

40 µL reference reactions were prepared as described for the test reactions, however, no test compound was added at this stage.

The test reactions and the reference reactions were incubated for 15 minutes at room temperature. It is expected that within the test reactions, condensed high density liquid droplets (mM concentration of protein) of FUS-SNAP protein (condensed phase) are present in an environment of a lower concentrated solution (µM concentration of protein) of FUS-SNAP dilute phase. Test compounds may or may not partition into the condensed phase causing a reduction of the concentration outside (test compound in the dilute phase) and an increase of the concentration inside (test compound in the droplets). The volume of high density liquid droplets is estimated to be at least 1000-fold smaller than the total volume of the reaction, e.g., 20 nL of a condensed phase in a 20 µL reaction.

Following the 15 minute incubation period, the test reactions and reference reactions were processed to separate condensates (the high density liquid droplets) from the supernatant (the dilute phase). Briefly, the test reactions and reference reactions were centrifuged at 10,000 rcf for 10 minutes in a cooled centrifuge at 20° C. When PCR-strips were sued, the rotor used was the Eppendorf F-45-48-5-PCR. 35 µL of the supernatant from each tube was removed and transferred to a new tube being careful not to disturb the pellets, which contained the condensates.

For the reference reactions, a known amount of the test compound was added to the tube containing the supernatant (which contains protein not associated with a condensate), such that the final compound concentration is the same as the initial concentration of the compound in the test reaction. Reference reactions can also be formed by measuring the amount of protein in the supernatant of a test reaction and replicating a supernatant solution based on the obtained information. The known amount of the compound added to the supernatant from the reference reaction was used to calibrate the mass spectrometry signal of the test reaction.

Additionally, the compound was extracted from the test reactions in order to directly measure the amount of compound in the formed condensates. The supernatant, which includes an amount of the test compound, was separated from the pellet comprising condensed protein. Briefly, the lids of each PCR tube were removed with scissors and each PCR tube was placed upside down in a 1.5 mL Eppendorf tube. The tubes were then centrifuged at 2,000 rcf for 5 seconds on a standard table top centrifuge. When PCR-strips were used, the PCR-strip can be plugged in upside down in an Eppendorf Microplate 96/V-PP (Cat #951040188) and centrifuged at 4,500 rcf for 1 minute. Subsequently, the compound was isolated from each pellet using a solution of ACN:MeOH (1:1). The samples may be sonicated as necessary.

The resulting samples from the test reactions and the reference reactions were analyzed by mass spectrometry. The ratio between the integrals of the corresponding MS signals between the relevant supernatant test reaction and the reference reaction reflected the depletion of the test compound due to partitioning into the formed condensates.

The partition characteristics of the test compounds were also determined using the fluorescence-based assay method disclosed in Example 2.

Results

Figure 7:
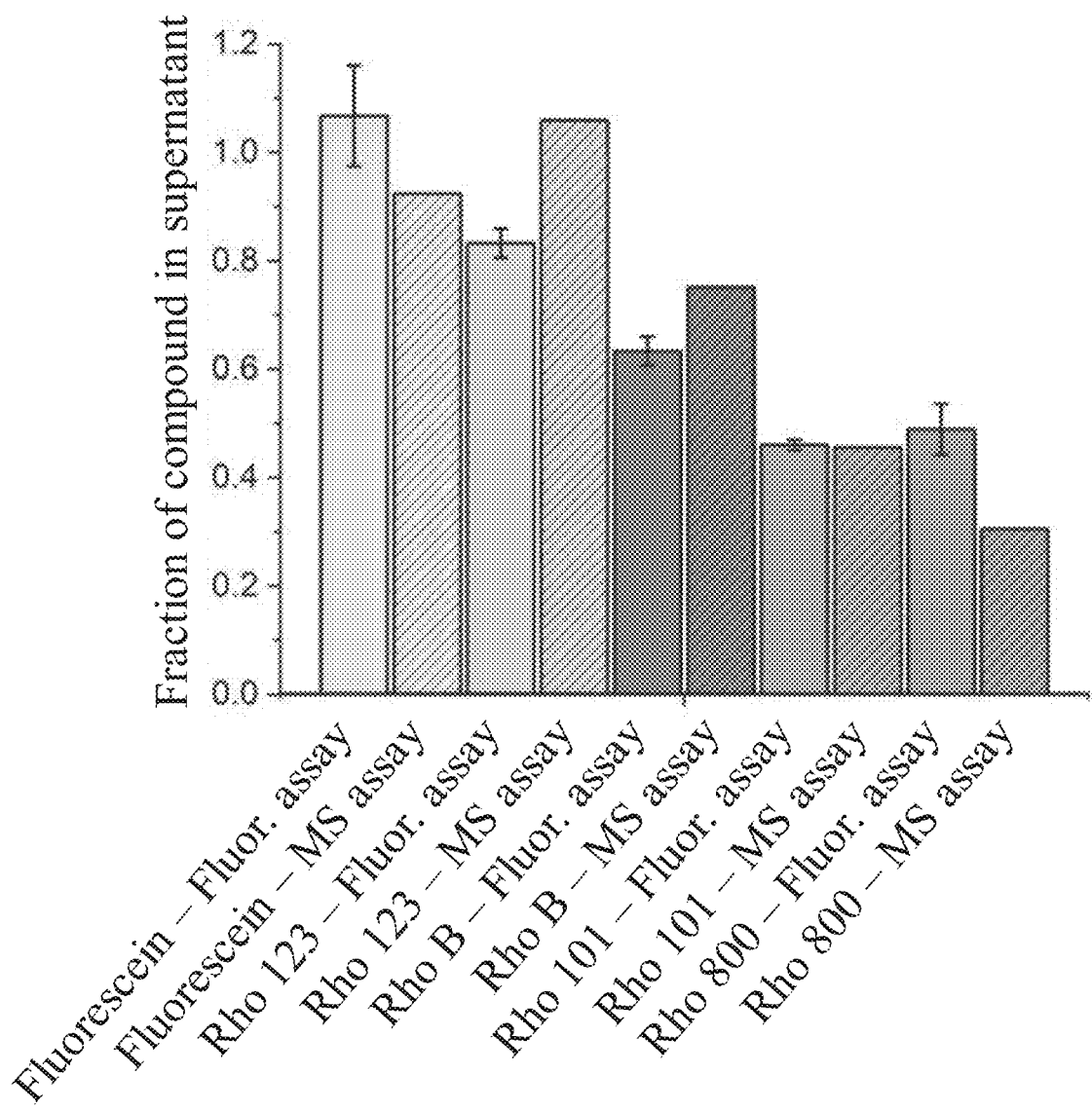
FIG. 7 shows a histogram of the fraction of compound in the supernatant (outside the condensates) of exemplary compounds using both a fluorescence-based assay and a mass spectrometry-based assay.

Rhodamine 101 (Rho 101), Rhodamine 800 (Rho 808), Rhodamine B (Rho B), Rhodamine 123 (Rho 123), and fluorescein were assessed using both the fluorescence-based assay and the mass spectrometry-based assay, as discussed above. As shown in FIG. 7, the two test methods produced partition characteristic measurements that were in good agreement for all of the tested compounds. Using the measurements, a ratio of compound concentration associated with the condensate compared to compound concentration not associated with the condensate was calculated for each compound. A condensate volume fraction of 1/1000 in relation to the outside phase was used. The results are provided in Table 7.

TABLE 8

Ratio of compound concentration in versus compound concentration out.

| Compound | MS-based assay | Fluorescence-based assay |
| --- | --- | --- |
| Rho 101 | >8,000 | 1,500 |
| Rho 800 | >2,000 | 1,000 |
| Rho B | 666 | 666 |
| Fluorescein | 1-100 | 1 |
| Rho 123 | 1-100 | 1 |

Additionally, the pelleted condensate samples were processed to extract and quantify the test compound therein. The results demonstrated that the sum of the amount of the test compound in the condensate and the amount of the test compound in the supernatant agreed with the total amount of the test compound added to the test reaction (data not provided).

As demonstrated herein, the mass spectrometry-based assay is a robust and sensitive assay to quantitatively determine partition characteristics of compounds. This technique is useful as a high-throughput screen. Certain additional advantages are realized for this mass spectrometry-based assay. For example, the mass spectrometry-based assay is not limited to fluorescent compounds, is a hypothesis-free technique (i.e., the identity of the test compound does not need to be known prior to the assay), is not limited by fluorescence quenching that may occur in the droplet interior, and, as demonstrated in Example 5, can be readily multiplexed.

Example 5

This example evaluates the impact of using different concentrations of test compound in the test reaction on the measurement of the test compound in the supernatant.

Test reactions and reference controls were prepared as described in Example 4. Fluorescein (which was identified as not partitioning into FUS-condensates) and Rhodamine 101 (which was identified as partitioning into FUS-condensates) were evaluated in separate test reactions at 0.01 µM, 0.1 µM, 1 µM, and 10 µM.

Results

Figure 8:
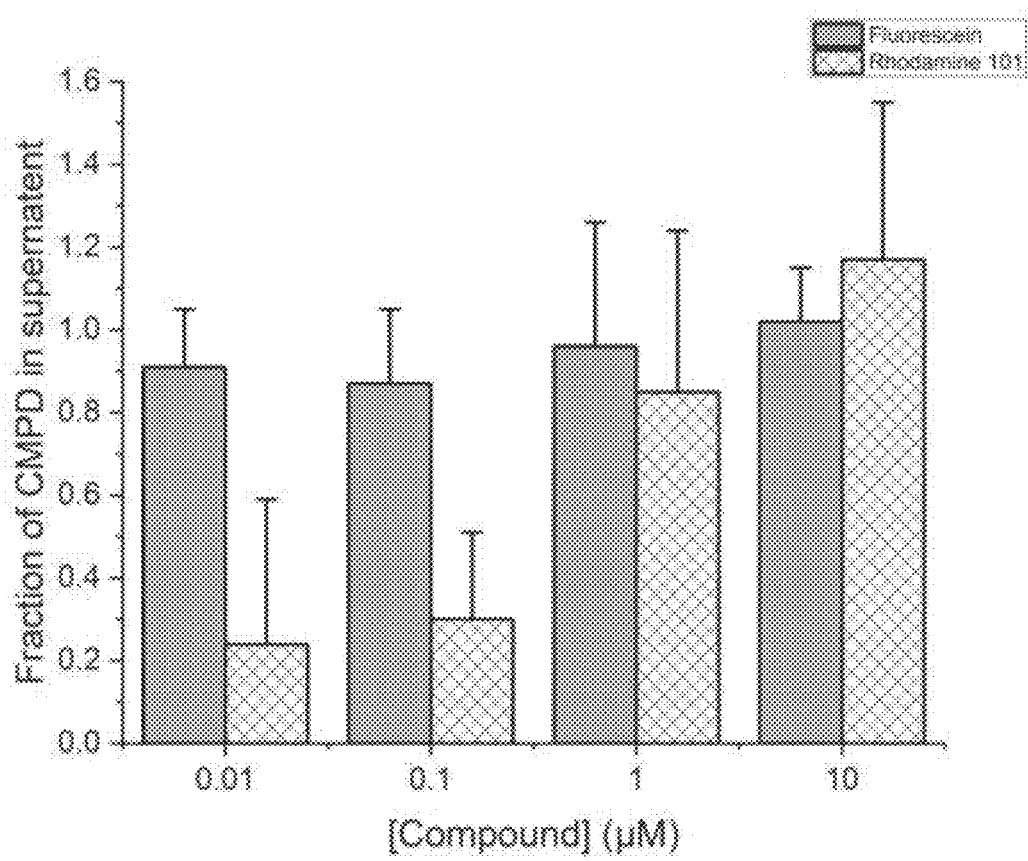
FIG. 8 shows a histogram of the fraction of compound in the supernatant of exemplary compounds evaluated at various compound concentrations.

As shown in FIG. 8, fluorescein does not partition into the FUS-condensates at any of the tested concentrations and the partitioning characteristic of fluorescein is concentration independent. Rhodamine 101 was observed to partition into the FUS-condensates at lower compound concentrations (see FIG. 8; 0.01 µM and 0.1 µM). Data represents mean±SD, N=3 technical repeats. As illustrated in FIG. 8, detection efficiency of a partitioning characteristic improves for reduced compound concentrations. As the amount of compound partitioning into a condensate may be small, using smaller amounts of a test compound added to the test reaction may allow for detection of small changes in the supernatant compound concentration relative to the reference control.

Example 6

Multiplexed Mass Spectrometry Depletion Assay

This example demonstrates the use of the mass spectrometry-based assay disclosed in Example 4 for studying systems comprising a plurality of test compounds.

Methods

FUS-SNAP protein reactions and reference reactions were prepared as described in Example 4. For test reactions, a set of four compounds, including Fluorescein and Rhodamine B, were used to create test reactions having a single compound at concentrations of 0.01 µM, 0.1 µM, and 1 µM, and test reactions having a mixture of all four compounds. All samples were prepared in triplicate. All samples were analyzed using the mass spectrometry-based assay described in Example 4.

Results

Figure 9A:
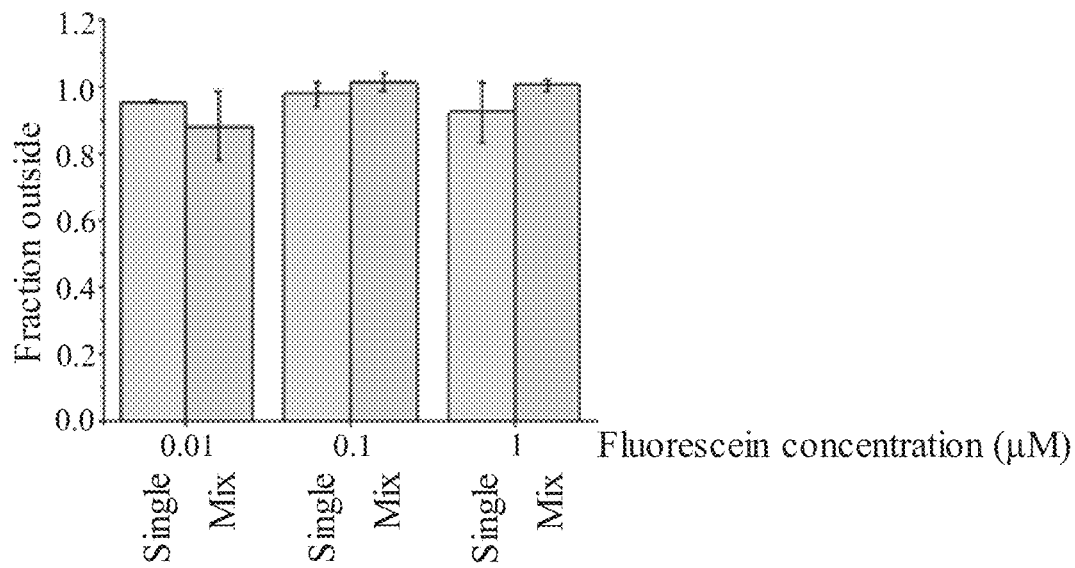
FIGS. 9A and 9B show histograms of the fraction of a compound of interest outside the condensates measured in systems having the single compound of interest and systems having a mixture of compounds including the compound of interest. Fluorescein is the compound of interest in FIG. 9A. Rhodamine B is the compound of interest in FIG. 9B.
Figure 9B:
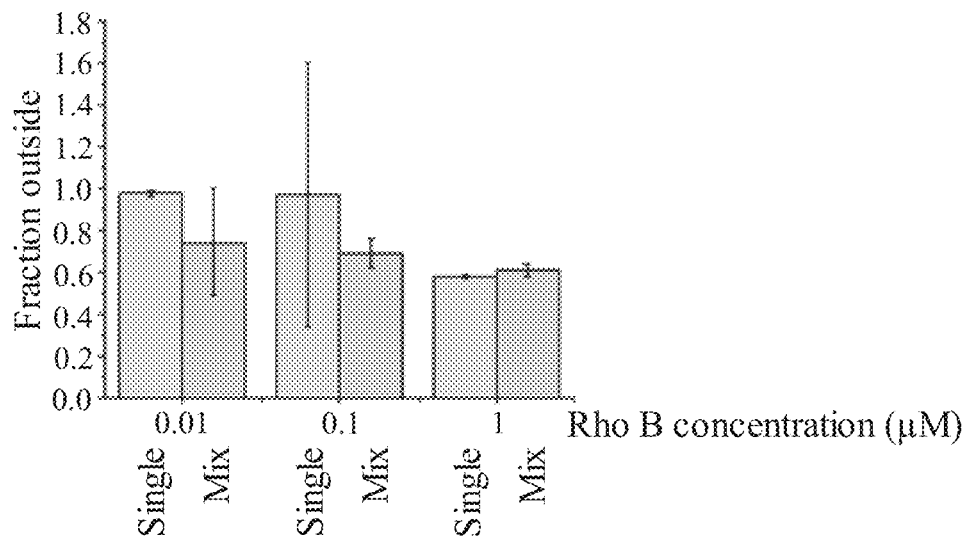

As shown in FIG. 9A, the measured fraction of Fluorescein outside of the FUS-SNAP condensates for single compound test reactions were in agreement with the measured fraction of Fluorescein outside of the FUS-SNAP condensates in the presence of the mixture of four compounds. As shown in FIG. 9B, the measured fraction of Rhodamine B (Rho B) outside of the FUS-SNAP condensates for single compound test reactions were in agreement with the measured fraction of Rhodamine B outside of the FUS-SNAP condensates in the presence of the mixture of four compounds. This demonstrates that the mass spectrometry-based technique can be used for multiplexed assays, which, e.g., enables higher throughput and/or the study of more complex systems.

Example 7

Multiplexing Using the Mass Spectrometry-Based Assay

This example further demonstrates the use of the mass spectrometry-based assay disclosed in Example 4 for studying systems comprising a plurality of test compounds.

Methods

FUS-SNAP protein reactions and reference reactions were prepared as described in Example 4. For test reactions, Fluorescein and Rhodamine 101 were assayed individually, and three sets of pooled compounds were also assayed. The first pool had 10 compounds (and included Fluorescein), the second pool had 15 compounds (and included Fluorescein and Rhodamine 101), and the third pool had 20 compounds (and included Fluorescein and Rhodamine 101). All samples were prepared and assayed in triplicate. All samples were analyzed using the mass spectrometry-based assay described in Example 4.

Results

Figure 10:
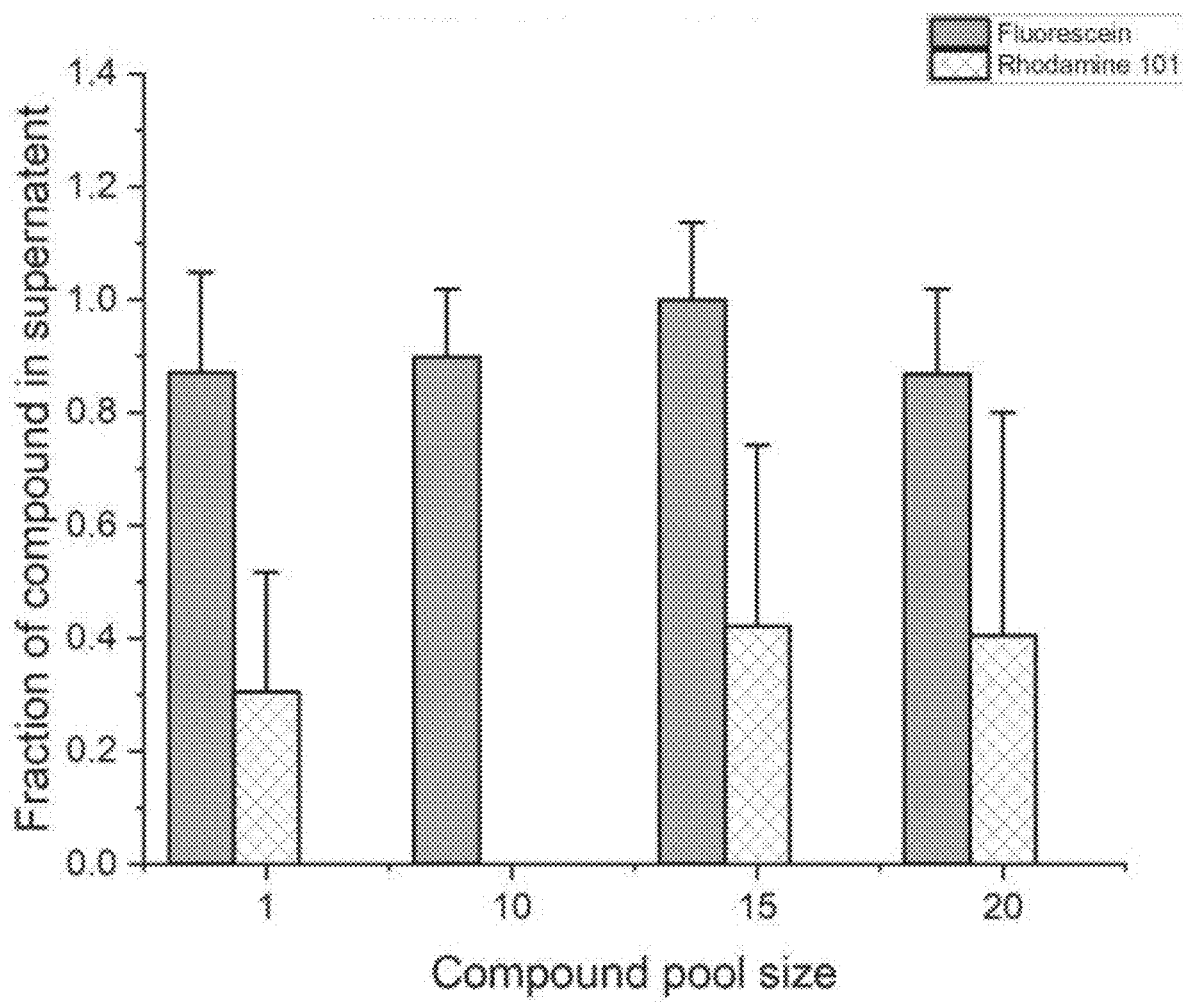
FIG. 10 shows a histogram of the fraction of compound in the supernatant for certain compounds in several multiplexed systems.

As shown in FIG. 10, the described assay, which, e.g., measures the depletion of the test compound in the supernatant due to the presence of the condensate, is capable of measuring the partition characteristic of an individual compound independent of compound pool size. These results demonstrate that compounds can be mixed in large pool sizes and still allow for measurements comparable to individually assessed single compound partition characteristic measurements. The mass spectrometry-based assay described herein thus enable high-throughput screening.

What is claimed is:

1. A method of determining a partition characteristic of a small molecule test compound in a target condensate, the method comprising:
   (a) obtaining a composition comprising the small molecule test compound, the target condensate, and an extra-condensate solution;
   (b) determining the amount of the small molecule test compound in the target condensate by mass spectrometry,
thereby determining the partition characteristic of the small molecule test compound in the target condensate.

2. The method of claim 1, further comprising causing the formation of the target condensate prior to step (a).

3. The method of claim 2, wherein the target condensate is formed in the presence of the small molecule test compound.

4. The method of claim 3, further comprising combining the small molecule test compound and a precursor composition comprising precursor molecules prior to or with formation of the target condensate.

5. The method of claim 2, wherein the target condensate is formed in the absence of the small molecule test compound.

6. The method of claim 5, further comprising combining the small molecule test compound and a composition comprising the target condensate and an extra-condensate solution.

7. The method of claim 1, wherein the determining the amount of the small molecule test compound in the target condensate is based on the amount of the small molecule test compound in the extra-condensate solution.

8. The method of claim 7, further comprising determining the amount of the small molecule test compound in the extra-condensate solution.

9. The method of claim 7, further comprising determining the fraction of the small molecule test compound in the extra-condensate solution.

10. The method of claim 8, further comprising separating the target condensate from the extra-condensate solution.

11. The method of claim 1, further comprising characterizing the target condensate by identifying one or more macromolecules comprised therein.

12. The method of claim 11, further comprising determining the amount of the one or more macromolecules in the target condensate.

13. The method of claim 1, wherein the target condensate is labeled with a radioactive label, a colorimetric label, or a fluorescent label.

14. The method of claim 1, wherein the method is a cell-based assay, and the composition comprises a cell.

15. The method of claim 14, wherein the target condensate is a cellular condensate that is determined to be dysregulated.

16. The method of claim 14, wherein the cell has one or more features of a neurodegenerative or proliferative disease.

17. The method of claim 15, wherein the cellular condensate is a cleavage body, a P-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

18. The method of claim 1, wherein the method is a cell-free assay.

19. The method of claim 1, wherein the small molecule test compound comprises a test compound label.

20. The method of claim 19, wherein the small molecule test compound label is a fluorescent label.

21. The method of claim 8, wherein the amount of the small molecule test compound is determined by mass spectrometry.

22. The method of claim 1, further comprising determining a relative partition characteristic of the small molecule test compound, wherein the relative partition characteristic of the small molecule test compound is determined by comparing the partition characteristic of the small molecule test compound in the target condensate and a partition characteristic of a reference compound in the target condensate.

23. The method of claim 1, further comprising determining a condensate preference profile of the small molecule test compound, wherein the condensate preference profile is determined by comparing the partition characteristic of the small molecule test compound in the target condensate and a partition characteristic of the small molecule test compound in a reference condensate.

24. The method of claim 1, further comprising determining the partition characteristic of each a plurality of small molecule test compounds in the target condensate, the method comprising performing the method of claim 1 for each of the plurality of small molecule test compounds.

25. The method of claim 24, further comprising identifying a subset of the plurality of small molecule test compounds having a desired partition characteristic.

26. The method of claim 25, further comprising identifying a common structural feature of the subset of the plurality of small molecule test compound.

27. The method of claim 1, wherein the target condensate comprises a precursor molecule, and the method further comprises determining an amount of the small molecule test compound that associates with the precursor molecule.

28. A method of identifying a compound characteristic associated with a desired partition characteristic of a subset of a plurality of small molecule test compounds into or out of a target condensate, the method comprising:
   (a) determining a partition characteristic of each of the plurality of small molecule test compounds in the target condensate by performing the method of claim 1;
   (b) identifying a group of the plurality of small molecule test compounds, each small molecule test compound of the group having the desired partition characteristic in the target condensate; and
   (c) identifying a compound characteristic that the subset of the plurality of small molecule test compounds in the group have in common.

29. The method of claim 28, further comprising selecting or designing a compound comprising the identified compound characteristic.

30. The method of claim 29, further comprising making the compound comprising the identified compound characteristic.

31. The method of claim 29, wherein the target condensate is associated with a disease and the compound is useful for treating the disease.

32. The method of claim 28, further comprising selecting or designing a compound that does not comprise the identified compound characteristic.

33. The method of claim 32, further comprising making the compound that does not comprise the identified compound characteristic.

34. The method of claim 32, wherein the target condensate is associated with a disease and the compound is useful for treating the disease.

35. A method of determining a partition characteristic of a small molecule test compound in a target condensate, the method comprising:

(a) combining the small molecule test compound and a composition comprising the target condensate and an extra-condensate solution;
(b) obtaining a reference control;
(c) measuring a MS signal of the small molecule test compound in the extra-condensate solution, or a portion thereof, using a mass spectrometry technique;
(d) measuring a MS signal of the small molecule test compound in the reference control, or a portion thereof, using a mass spectrometry technique; and
(e) comparing the MS signal of the small molecule test compound from the extra-condensate solution and the MS signal of the small molecule test compound from the reference control, thereby determining the partition characteristic of the small molecule test compound in the target condensate.

36. The method of claim 35, wherein the amount of the small molecule test compound combined with the composition is 100 nM or less, and the amount of a precursor molecule in the composition, including in the target condensate, is about 5 μM.

* * * * *